US008389736B2

(12) United States Patent
Kurth et al.

(10) Patent No.: US 8,389,736 B2
(45) Date of Patent: Mar. 5, 2013

(54) COMPOUNDS HAVING ACTIVITY IN CORRECTING MUTANT-CFTR PROCESSING AND USES THEREOF

(75) Inventors: Mark J. Kurth, Davis, CA (US); Alan S. Verkman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 150 days.

(21) Appl. No.: 12/682,428

(22) PCT Filed: Sep. 5, 2008

(86) PCT No.: PCT/US2008/075503
§ 371 (c)(1),
(2), (4) Date: Jul. 12, 2010

(87) PCT Pub. No.: WO2009/051909
PCT Pub. Date: Apr. 23, 2009

(65) Prior Publication Data
US 2010/0273839 A1 Oct. 28, 2010

Related U.S. Application Data

(60) Provisional application No. 60/980,389, filed on Oct. 16, 2007.

(51) Int. Cl.
*C07D 513/14* (2006.01)
*A61K 31/425* (2006.01)
(52) U.S. Cl. ....................................... 548/151; 514/366
(58) Field of Classification Search .................. None
See application file for complete search history.

(56) References Cited

U.S. PATENT DOCUMENTS 8,143,295 B2 * 3/2012 Verkman et al. .............. 514/366

FOREIGN PATENT DOCUMENTS

| WO | WO2005068444 | | 7/2005 |
| WO | WO 2006050351 A2 * | 5/2006 |
| WO | WO 2006101740 A2 * | 9/2006 |
| WO | WO 2006122011 A2 * | 11/2006 |
| WO | WO2007008541 | | 1/2007 |
| WO | WO 2007059195 A1 * | 5/2007 |

OTHER PUBLICATIONS

Pedemonte et al. Journal of Clinical Investigation (2005), 115(9), 2564-2571.*
Dayam, Journal of Medicinal Chemistry (2006), 49 (15), 4526-4534.*
Galam et al., Bioorganic & Medicinal Chemistry 15 (2007) 1939-1946.*
Wang et al Biochem. J. (2007) 406: 257-263.*
Wang et al. Journal of Biological Chemistry (2007) 282(46): 33247-33251.*
Borrok et al.JACS (2007) 129: 12780-12785.*

* cited by examiner

*Primary Examiner* — Kamal Saeed
*Assistant Examiner* — Nyeemah A Grazier
(74) *Attorney, Agent, or Firm* — Rudy J. Ng; Carol L. Francis; Bozicevic, Field & Francis LLP

(57) ABSTRACT

The invention provides compositions, pharmaceutical preparations and methods for increasing activity of a mutant cystic fibrosis transmembrane conductance regulator protein (mutant-CFTR). The compositions pharmaceutical preparations and methods are useful for the study and treatment of disorders associated with mutant-CFTR, such as cystic fibrosis. The compositions and pharmaceutical preparations of the invention may comprise one or more bithiazole-containing compounds of the invention, or an analog or derivative thereof.

14 Claims, 19 Drawing Sheets

[a]

[b]

US 8,389,736 B2

COMPOUNDS HAVING ACTIVITY IN CORRECTING MUTANT-CFTR PROCESSING AND USES THEREOF

CROSS-REFERENCE TO RELATED APPLICATIONS

This application claims priority under 35 U.S.C. §119(e) of U.S. Provisional Patent Application No. 60/980,389, filed Oct. 16, 2007, which is herein incorporated by reference in its entirety.

STATEMENT REGARDING FEDERALLY SPONSORED RESEARCH

This invention was made with government support under grant nos. HL73856, EB004 15, HL59198, EY 13574, and DK35 124 awarded by the National Institutes of Health. The government has certain rights in this invention.

Work on this invention was also supported by grants from the Cystic Fibrosis Foundation and/or from Cystic Fibrosis Foundation Therapeutics.

FIELD OF THE INVENTION

The present invention relates to corrector compounds and methods for correcting cellular processing of mutant cystic fibrosis transmembrane conductance regulator protein.

BACKGROUND OF THE INVENTION

The cystic fibrosis transmembrane conductance regulator protein (CFTR) is a cAMP activated chloride ion (Cr) channel responsible for Cl⁻ transport. CFTR is expressed in epithelial cells in mammalian airways, intestine, pancreas and testis. It is there where CFTR provides a pathway for the movement of Cl⁻ ions across the apical membrane and a key point at which to regulate the rate of transepithelial salt and water transport. Hormones, such as a β-adrenergic agonist, or toxins, such as cholera toxin, lead to an increase in cAMP, activation of cAMP-dependent protein kinase, and phosphorylation of the CFTR Cl⁻ channel, which causes the channel to open. An increase in the concentration of $Ca^{2+}$ in a cell can also activate different apical membrane channels. Phosphorylation by protein kinase C can either open or shut Cl⁻ channels in the apical membrane.

Dysfunction of CFTR is associated with a wide spectrum of disease, including cystic fibrosis (CF) and with some forms of male infertility, polycystic kidney disease and secretory diarrhea. CF is a hereditary disease that mainly affects the lungs and digestive system, causing progressive disability and early death. With an average life expectancy of around 31 years, CF is one of the most common life-shortening, childhood-onset inherited diseases. This disease is caused by mutation of the gene encoding CFTR, and is autosomal recessive. The most common CFTR mutation, deletion of phenylalanine-508 (ΔF508-CFTR), is present in at least one allele in about 90% of CF patients (Egan et al., (2004) *Science* 304:600-602). ΔF508-CFTR causes Cl⁻ impermeability because it is not processed correctly, causing it to be retained at the endoplasmic reticulum (rather than the plasma membrane). ΔF508-CFTR also has reduced intrinsic Cl⁻ conductance relative to wild type CFTR.

Strategies have been investigated to correct the defects in ΔF508-CFTR cellular processing and intrinsic function in cells. Cell growth at low temperature (<30° C.) (Denning et al., (1992) *Nature* 358, 761-764) or with high concentrations of chemical chaperones such as glycerol (Sato et al., (1996) *J. Biol. Chem.* 271, 635-638; Brown, et al., (1996) *Cell Stress & Chaperones* 1, 1 17-125) corrects partially defective ΔF508-CFTR cellular processing by a mechanism that may involve improved protein folding and stability (Sharma et al., (2001) *J. Biol. Chem.* 276, 8942-8950). A sustained increase in intracellular calcium concentration by thapsigargin also corrects defective ΔF508-CFTR processing (Egan et al., (2002) *Nature Med.* 8, 485-492), possibly by interfering with interactions with molecular chaperones. Compounds like phenylbutyrate facilitate ΔF508-CFTR cellular processing by altering chaperone function and/or transcriptional enhancement (Rubenstein et al., (2000) *Am. J. Physiol.* 278, C259-C267; Kang et al., (2002) *Proc. Natl. Acad. Sci. U.S.A.* 99, 838-843). Although these approaches provide insight into mechanisms of ΔF508-CFTR retention at the endoplasmic reticulum, they probably do not offer clinically-useful therapies.

ΔF508-CFTR has significantly impaired channel activity even when present at the cell plasma membrane (Dalemans et al., (1991) *Nature* 354, 526-528). Cell-attached patchclamp measurements showed reduced ΔF508-CFTR open channel probability and prolonged closed times even with maximal cAMP stimulation (Haws et al., (1996) *Am. J. Physiol.* 270, C1544-C1555; Hwang et al., (1997) *Am. J. Physiol.* 273, C988-C998). Patch-clamp measurements in excised membranes indicated 7-fold reduced ΔF508-CFTR activation after phosphorylation compared to wildtype CFTR. Relatively high concentrations of the flavone genistein (>50 pM, Hwang, et al., (1997) *Am. J. Physiol.* 273, C988-C998; Wang et al., (2000) *J. Physiol.* 524, 637-638) or the xanthine isobutylmethylxanthine (>1 mM, Drurnrn et al., (1991) *Science* 254, 1797-1799) in combination with cAMP agonists increase ΔF508-CFTR channel activity. Again, these studies have not offered any clinically useful therapies.

Recent identification of small molecule bithiazole derivatives as correctors of mutant CFTR cellular processing or folding have been reported (WO 2006/101740). The derivatives were effective in the high nanomolar (nM) range. However, one of the most potent compounds reported in WO 2006/101740 has features that may impact optimal drug activity.

There is accordingly still a need for compounds that can correct cellular processing or folding of mutant CFTR, e.g., ΔF508-CTFR, and methods of using such compounds for the study and treatment of CF and the treatment and control of other secretory disorders. The present invention addresses these needs, as well as others.

Literature

Bithiazole derivatives as correctors of mutant CFTR cellular processing are reported in International Patent Application Publication (PCT) No. WO 2006/101470. Other PCT publications related to CFTR are represented by WO 01/55106 and WO 2005/120497.

Compounds, formulations and methods of diagnosing and treating mutant-CFTR associated disorders, and related literature of interest are reported in the following U.S. Pat. Nos. 3,953,428; 5,240,846; 5,366,977; 5,407,796; 5,434,086; 5,543,399; 5,582,825; 5,602,110; 5,621,007; 5,635,160; 5,639,661; 5,670,488; 5,674,898; 5,750,571; 5,776,677; 5,834,214; 5,840,702; 5,855,918; 5,863,770; 5,877,179; 5,908,611; 5,939,255; 5,939,536; 5,948,814; 5,958,893; 5,958,907; 5,972,995; 5,976,499; 5,981,178; 5,981,714; 5,989,521; 6,001,588; 6,015,828; 6,030,961; 6,033,688; 6,043,389; 6,063,913; 6,083,954; 6,093,567; 6,110,955; 6,130,248; 6,159,968; 6,201,107; 6,245,735; 6,251,930; 6,281,240; 6,323,187; 6,323,191; 6,329,422; 6,465,494; 6,573,073; 6,599,907; 6,630,482; 6,635,627; 6,723,703;

6,730,777; 6,770,739; 6,780,839; 6,902,907; 6,936,618; 6,984,487; 7,118,911; 7,160,729; 7,235,573; 7,238,474; 7,256,210; 7,258,854; 7,259,184; 7,259,250; 7,259,266; 7,261,102; 7,262,200; 7,264,926; 7,264,948; 7,265,088; 7,265,110; 7,265,114; 7,265,148; 7,265,153; 7,267,120; 7,267,652; 7,267,994; 7,268,134; 7,268,155; and 7,268,159.

Reports on the study and correction of defects in CFTR are found in the following references: Denning et al., (1992) *Nature* 358, 761-764; Sato et al., (1996) *J. Biol. Chem.* 271, 635-638; Brown, et al., (1996) *Cell Stress & Chaperones* 1, 1 17-125; Sharma et al., (2001) *J. Biol. Chem.* 276, 8942-8950; Egan et al., (2002) *Nature Med.* 8, 485-492; Rubenstein et al., (2000) *Am. J. Physiol.* 278, C259-C267; Kang et al., (2002) *Proc. Natl. Acad. Sci. U.S.A.* 99, 838-843; Dalemans et al., (1991) *Nature* 354, 526-528; Haws et al., (1996) *Am. J. Physiol.* 270, C1544-C1555; Hwang, et al., (1997) *Am. J. Physiol.* 273, C988-C998; Wang et al., (2000) *J. Physiol.* 524, 637-638; and Drurnrn et al., (1991) *Science* 254, 1797-1799.

SUMMARY OF THE INVENTION

The invention provides compositions, pharmaceutical preparations and methods for increasing activity (e.g., ion transport) of a mutant-cystic fibrosis transmembrane conductance regulator protein ("mutant-CFTR") that are useful for the study and treatment of cystic fibrosis ("CF"). The compositions and pharmaceutical preparations may comprise one or more compounds of the invention, or an analog or derivative thereof.

The compositions of the invention comprise a compound of formula (I):

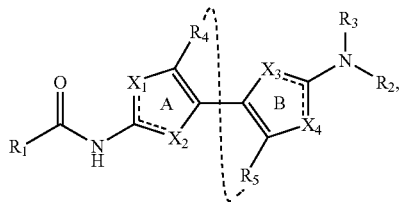

(I)

or the salts, solvates, hydrates, and prodrug forms thereof, and stereoisomers thereof, wherein:

A and B are aromatic rings each independently selected from thiazole and oxazole, with $X_1$, $X_2$, $X_3$ and $X_4$ being heteroatoms selected from N, O and S, with each dotted line connecting $X_1$ to $X_2$ within ring A and $X_3$ to $X_4$ within ring B being a single or double bond provided that when one bond is a double bond then the other bond is a single bond, and with the dotted line connecting $R_4$ and $R_5$ indicating rotational isomers around the solid line bond connecting rings A and B;

$R_1$ is a substituted or unsubstituted group selected from aliphatic and aryl, with the proviso that when $R_1$ is an unsubstituted phenyl then $R_3$ or $R_5$ is other than hydrogen;

$R_2$ is a substituted or unsubstituted aryl;

$R_3$ is hydrogen or substituted or unsubstituted aliphatic; and $R_4$ and $R_5$ are each independently hydrogen, a substituted or unsubstituted lower aliphatic, or form a bridge comprising a heteroatom or a substituted or unsubstituted lower aliphatic chain, with the dotted line connecting $R_4$ and $R_5$ further indicating either no bridge for unbridged $R_4$ and $R_5$ or said bridge for bridged $R_4$ and $R_5$.

The pharmaceutical preparations of the invention include an effective amount of a CFTR corrector compound of the invention. The pharmaceutical compositions can include at least one of a pharmaceutically acceptable carrier, a pharmaceutically acceptable diluent, a pharmaceutically acceptable excipient, and a pharmaceutically acceptable adjuvant.

The methods of the invention include treating a subject having a condition associated with mutant-CFTR, which involves administering to the subject a therapeutically effective amount of a pharmaceutical composition of the invention. The invention also includes a method of increasing ion permeability of a cell producing a mutant-CFTR protein, which involves contacting the cell with an effective amount of a composition of the invention so as to increase CFTR-mediated ion permeability of the cell.

The invention also provides kits containing one or more compositions of the invention, as well as methods of preparing the compositions.

Advantages of the compounds and compositions of the invention include improved drug like properties such as increased potency and solubility, as well as expanded diversity for generating additional corrector compounds. The compounds also are useful in the study of mutant-CFTR related disorders. Thus the invention addresses many unmet needs in the development and use of mutant-CFTR corrector compounds. These and other objects and advantages of the invention will be apparent from the detailed description below.

DETAILED DESCRIPTION OF SPECIFIC EMBODIMENTS

Figure 1:
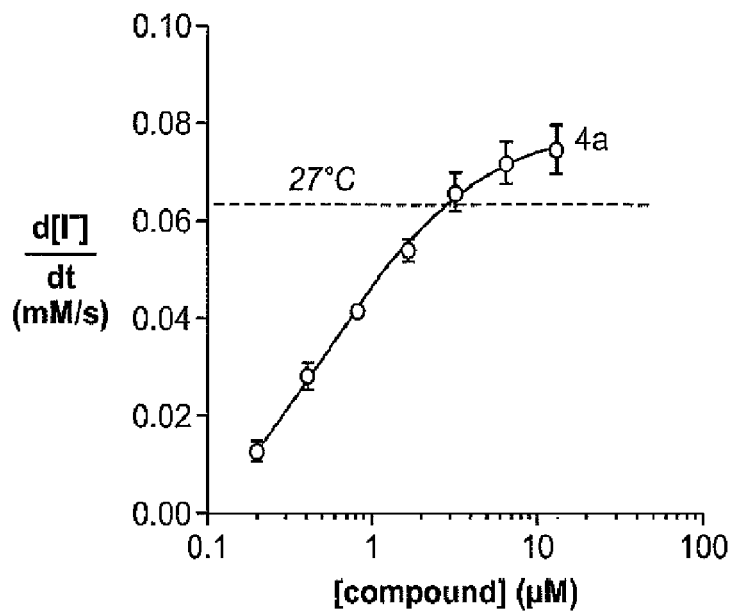
FIG. 1: Dose-response curve of corrector 4 (mean±S.E., n=4) in correcting Δ508-CFTR.

The present invention is based on the discovery of new bithiazole and related compounds that correct cellular processing or folding of mutant cystic fibrosis transmembrane conductance regulator protein ("mutant-CFTR") with high nanomolar potency, and that exhibit a broad range of one or more other properties that find use in the study and treatment of disorders related to mutant-CFTR, such as cystic fibrosis ("CF").

The compounds of the invention share a bithiazole, oxazole or mixed thiazole-oxazole core that includes several structural and functional diversity points that differ from previously reported bithiazole-based corrector compounds, such as the Corr4 (also called "Corr4a" or "4a") mutant-CFTR corrector reported in WO 2006/101740. These differences include, for example, identification of new diversity elements that replace or tune the phenyl substituents of Corr 4, and modification of the bithiazole core itself. The compounds of the invention represent a fundamental advance in that potency as well as other properties are modified or improved relative to Corr 4. Accordingly, the subject compounds differ both chemically and structurally to previously known mutant-CFTR corrector compounds.

By exploiting these different chemical and structural aspects in the design, synthesis and screening of new compound libraries of the invention, key features necessary for optimization of compounds containing a bithiazole core structural motif have been identified. The compounds of the invention include one or more of such features so as to impart a pharmacological or biological property that benefits the compound's manufacture, handling, potency, selectivity, and/or pharmacokinetic parameters. The invention also includes compounds with features useful in the study of mutant-CFTR.

As such, the invention provides novel compounds, compositions and pharmaceutical preparations that correct cellular processing or folding of mutant-CFTR (e.g., ΔF508-CFTR). The invention also features methods of use of such compositions in the treatment of a subject for CF, as well as increasing activity of mutant CFTR in a cell, e.g., by correcting cellular processing or folding of mutant CFTR, as well as kits and compound libraries useful for the study and treatment of CF.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "and", and "the" include plural referents unless the context clearly dictates otherwise. Thus, for example, reference to a "compound" includes a plurality of such compounds and equivalents thereof known to those skilled in the art, and so forth.

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, $C_{2-6}$ alkenyl, $C_{3-6}$ alkynyl, $C_{1-6}$ alkoxy, aryl and di-$C_{1-6}$ alkylamino.

"Acyl" refers to a radical —C(O)R, where R is hydrogen, alkyl, cycloalkyl, cycloheteroalkyl, aryl, arylalkyl, heteroalkyl, heteroaryl or heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)-cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to 6 or 12 carbon atoms. The simplest aliphatic compound is methane and its chemically bonded form methyl (e.g., $CH_4$, $CH_3$—, —$CH_2$—, —$CH(R_i)(R_{ii})$—, Aliphatics include saturated and unsaturated compounds. Lower aliphatics typically refer to shorter aliphatic compounds having from 1 to 6 carbon atoms.

"Alkanoyl" or "acyl" as used herein refers to the group —C(O)H or —C(O)-alkyl.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxyamino" refers to a radical —N(H)O-alkyl or —N(H)O-cycloalkyl as defined herein.

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Alkylamino" refers to a radical alkyl-NRR', wherein each of R and R' are independently selected from hydrogen and alkyl.

"Alkylarylamino" refers to a radical —NRR' where R represents an alkyl or cycloalkyl group and R' is an aryl as defined herein.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkylthio" refers to a radical —S-alkyl or —S-cycloalkyl group as defined herein that may be optionally substituted as defined herein. Representative examples include, but are not limited to, methylthio, ethylthio, propylthio, butylthio, and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amide" refers to the radical —NHC(O)— or —C(O)NH$_2$.

"Amino" refers to the radical —NH$_2$.

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Aminohydroxyphosphoryl" refers to the radical —PO(OH)NH$_2$.

"Aralkyl" or "arylalkyl" refers to an alkyl group, as defined above, substituted with one or more aryl groups, as defined above.

"Aromatic" refers to a mono- or polycyclic aromatic hydrocarbon group, and may include one or more heteroatoms in the aromatic ring or ring system termed a heteroaromatic. Also referred to as "aromatic ring" or "aromatic ring system." Simple aromatics comprise from 3-14 carbons, examples of which include arsindole, benzene, benzothiophene, benzo[c]thiophene, benzimidazole, benzoxazole, benzisoxazole, benzothiazole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, purine quinazoline, quinoline, quinolizine, quinoxaline, tetrazole, thiadiazole, thiazole, thiophene, triazole, [2,4,6]triazine and xanthene, as well as fused ring systems such as acridine, anthracene, cinnoline, naphthalene, naphthyridine, quinoline, isoquinoline, quinoxaline and quinazoline.

"Aryl" refers to any functional group or substituent derived from a simple aromatic ring by removal of a hydrogen atom from a carbon atom of a parent aromatic ring system. Typical aryl groups comprises from 6 to 14 carbon atoms. Examples include the radicals of arsindole, benzene, benzothiophene, benzo[c]thiophene, benzimidazole, benzoxazole, benzisoxazole, benzothiazole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, purine quinazoline, quinoline, quinolizine, quinoxaline, tetrazole, thiadiazole, thiazole, thiophene, triazole, [2,4,6]triazine and xanthene, as well as fused ring systems such as acridine, anthracene, cinnoline, naphthalene, naphthyridine, quinoline, isoquinoline, quinoxaline and quinazoline. Examples of radicals denoted by the term "aryl" that are of particular interest include: phenyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

"Arylalkyloxy" refers to an —O-arylalkyl radical where arylalkyl is as defined herein.

"Arylamino" refers to the group aryl-NRR', wherein each of R and R' are independently selected from hydrogen, aryl and heteroaryl.

"Aryloxy" refers to —O-aryl groups wherein "aryl" is as defined herein.

"Arylsulfonyl" refers to a radical —S(O)$_2$R where R is an aryl or heteroaryl group as defined herein.

"Azide" refers to N$_3$ or its radical —N$_3$ (also referred to as "azido").

"Carbamoyl" refers to the radical —C(O)N(R)$_2$ where each R group is independently hydrogen, alkyl, cycloalkyl or aryl, as defined herein, which may be optionally substituted as defined herein.

"Carbonyl" refers to the radical —C(O)—.

"Carboxy" refers to the radical —C(O)OH (also referred to as "carboxyl").

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, which can be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is CR$^7$, NR$^3$, O, or S; Q is O, NR$^3$ or S.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Halo" or "halogen" refers to fluoro, chloro, bromo and iodo. Halo groups can be either fluoro or chloro.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heterocycle" refers to a closed ring hydrocarbon in which one or more of the atoms in the ring are an element other than carbon (e.g., nitrogen, oxygen, sulfur, etc.). Includes aromatic (aryls and heteroaryls) and non-aromatic (cycloheteroalkyl) rings and systems.

"Heteroaryl" refers to a monovalent heteroaromatic group derived by the removal of a hydrogen atom from an atom of a parent heteroaromatic ring system. Typical heteroaryl groups include, but are not limited to, groups derived from arsindole, benzene, benzothiophene, benzo[c]thiophene, benzimidazole, benzoxazole, benzisoxazole, benzothiazole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, oxadiazole, oxazole, perimidine, phenanthridine, phenanthroline, phenazine, phthalazine, pteridine, purine, pyran, pyrazine, pyrazole, pyrazine, pyridazine, pyridine, pyrimidine, pyrrole, pyrrolizine, purine quinazoline, quinoline, quinolizine, quinoxaline, tetrazole, thiadiazole, thiazole, thiophene, triazole, [2,4,6]triazine and xanthene, as well as fused ring systems such as acridine, anthracene, cinnoline, naphthalene, naphthyridine, quinoline, isoquinoline, quinoxaline and quinazoline, and the like. In some embodiments, the heteroaryl groups are those derived from thiazole, thiophen, pyrrole, benzothiophene, benzofuran, indole, pyridine, quinoline, imidazole, oxazole and pyrazine.

"Hydroxyl" refers to the radical —OH.

"Nitro" refers to the radical —NO$_2$.

"Phenyl" (often abbreviated as -Ph) is the aryl form of benzene with the functional group, and has the formula —$C_6H_5$, where the six carbon atoms are arranged in an aromatic ring structure.

"Substituted" refers to a group in which one or more hydrogen atoms are each independently replaced with the same or different substituent(s). Typical substituents include, but are not limited to, —X, —$R^{14}$, —O—, =O, —$OR^{14}$, —$SR^{14}$, —$S^-$, =S, —$NR^{14}R^{15}$, =$NR^{14}$, —$CX_3$, —$CF_3$, —OCN, —SCN, —NO, —$NO_2$, =$N_2$, —$N_3$, —$S(O)_2O^-$, —$S(O)_2$OH, —$S(O)_2R^{14}$, —$OS(O_2)O^-$, —$OS(O)_2R^{14}$, —$P(O)(O—)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^{16}$, —$C(S)OR^{14}$, —$NR^{16}C(O)NR^{14}R^{15}$, —$NR^{16}C(S)NR^{14}R^{15}$, —$NR^{17}C(NR^{16})NR^{14}R^{15}$ and —$C(NR^{16})NR^{14}R^{15}$, where each X is independently a halogen, and where "$R^{14}$", "$R^{15}$", "$R^{16}$" and "$R^{17}$" are independently hydrogen, alkyl, substituted alkyl, aryl, arylalkyl, cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{18}R^{19}$, —$C(O)R^{18}$ or —$S(O)_2R^{18}$ or optionally $R^{18}$ and $R^{19}$ together with the atom to which they are both attached form a cycloheteroalkyl or substituted cycloheteroalkyl ring, and where "$R^{18}$", "$R^{19}$", and "$R^{22}$" are each independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

"Substituted aliphatic" includes those groups recited in the definition of "substituted" herein, and particularly refers to aliphatic group having 1 or more substituents, for instance from 1 to 5 substituents, and particularly from 1 to 3 substituents, selected from the group consisting of selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-$S(O)_2$—, and aryl-$S(O)_2$—.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Substituted amino" includes those groups recited in the definition of "substituted" herein, and particularly refers to the group —$N(R)_2$ where each R is independently selected from the group consisting of hydrogen, aliphatic, substituted aliphatic, alkyl, substituted alkyl, alkenyl, substituted alkenyl, alkynyl, substituted alkynyl, aryl, cycloalkyl, substituted cycloalkyl, and where both R groups are joined to form an alkylene group.

"Substituted aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, aliphatic, substituted aliphatic, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-$S(O)_2$— and aryl-$S(O)_2$—. May include heteroaryls and substituted heteroaryls in which one or more carbon atoms of the aromatic ring system is replaced by a group selected from N, O and S. Examples of substituents of particular interest are from one to three halo, trihalomethyl, amino, protected amino, amino salts, monosubstituted amino, disubstituted amino, carboxy, protected carboxy, carboxylate salts, hydroxy, protected hydroxy, salts of a hydroxy group, lower alkoxy, lower allylthio, alkyl, substituted alkyl, cycloallyl, substituted cycloalkyl, (cycloallyl)alkyl, substituted (cycloalkyl)allyl, phenyl, substituted phenyl, phenylalkyl, and (substituted phenyl)allyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted phenyl" includes those groups recited in the definition of "substituted" herein, and particularly refers to a phenyl group that may optionally be substituted with 1 or more substituents, for instance from 1 to 5 substituents, particularly 1 to 3 substituents. Substituents of the phenyl group include those selected from the group consisting of acyl, acylamino, acyloxy, alkenyl, substituted alkenyl, aliphatic, substituted aliphatic, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—. Substituents of the phenyl group include those that form a fused phenyl ring system in which a heterocycle ring is fused to the phenyl ring, and the heterocycle contains one or more heteroatoms independently selected from N, O and S. Substituents of the phenyl group of particular interest are selected from the group consisting of halogen, hydroxy, protected hydroxy, amino, protected amino, amide, protected amide, thiol, protected thiol, cyano, nitro, azido, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(pl~enylsulfonyl) amino or phenyl, substituted or unsubstituted, such that, for example, a biphenyl or naphthyl group results. Examples of substituted phenyls include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2,3, or 4-hydroxyphenyl, 2,4-dihydroxyphenyl, the protected-hydroxy derivatives thereof and the like; a nitrophenyl group such as 2,3, or 4-nitrophenyl; a cyanophenyl group, for example, 2, 3 or 4-cyanophenyl; a mono- or di(alkyl)phenyl group such as 2,3, or 4-methylphenyl, 2,4-dimethylphenyl, 2, 3 or 4-(iso-propyl)phenyl, 2,3, or 4-ethylphenyl, 2, 3 or 4-(n-propyl)phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-dibrotected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or dim-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like "Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$.

"Sulfanyl" refers to the radical —SH. "Substituted sulfanyl" refers to a radical such as —SR wherein R is any substituent described herein.

"Sulfone" refers to the group —SO$_2$R. In particular embodiments, R is selected from H, lower alkyl, alkyl, aryl and heteroaryl.

"Sulfonyl" refers to the divalent radical —S(O$_2$)—. "Substituted sulfonyl" refers to a radical such as R—(O$_2$)S— wherein R is any substituent described herein. "Aminosulfonyl" refers to the radical H$_2$N(O$_2$)S—, and "substituted aminosulfonyl" refers to a radical such as R$_2$N(O$_2$)S— wherein each R is independently any substituent described herein.

"Thioalkoxy" refers to the group —S-alkyl.

"Thioaryloxy" refers to the group —S-aryl.

"Thioketo" refers to the group =S.

"Thiol" refers to the group —SH.

One having ordinary skill in the art will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

A "mutant cystic fibrosis transmembrane conductance regulator protein" or "mutant-CFTR" is the protein that results from a mutation, e.g., deletion mutation, insertion mutation, or point (substitution) mutation of the CFTR gene product relative to wildtype. A "mutant cystic fibrosis transmembrane conductance regulator protein", or "mutant-CFTR" refers to a dysfunctional CFTR as compared to a functional (e.g., wildtype) CFTR, where the dysfunction can encompass one or more of the following: (i) aberrant CFTR production (e.g., at the level of transcription or translation); (ii) aberrant folding and/or trafficking; (iii) abnormal regulation of conductance; (iv) decreases in chloride conductance; (v) reduction in synthesis; and the like. A "mutant-CFTR gene" is a gene, or coding sequence, which encodes a mutant-CFTR. For the purposes of this application, the terms "genome" and "gene" are used interchangeably, e.g. "genome that encodes mutant-CFTR" and "gene that encodes mutant-CFTR".

A "gating defective mutant cystic fibrosis transmembrane conductance regulator protein" or "gating defective mutant-CFTR" is a mutant-CFTR that is present on the cell surface and is defective in gating of ions through the channel (e.g., regulation of ion transport). Thus, as used herein a "gating defective mutant-CFTR" encompasses dysfunctions associated with (i) abnormal regulation of conductance; and or (ii) decreases in chloride conductance.

A "mutant-CFTR protein-mediated condition" means any condition, disorder or disease, or symptom of such condition, disorder, or disease that results from or is correlated to the presence of a mutant-CFTR, e.g., ΔF508-CFTR, e.g., chloride ion impermeability caused by reduced activity of ΔF508-CFTR in ion transport relative to a wild-type CFTR. A "mutant-CFTR protein-mediated condition" encompasses conditions in an affected subject which are associated with the presence of a ΔF508-CFTR mutation on at least one allele, thus including subjects that carry a ΔF508-CFTR mutation on both alleles as well as compound heterozygous subjects having two different mutant forms of CFTR, e.g., a subject with one copy of ΔF508-CFTR and a copy of different mutant form of CFTR. Such conditions, disorders, diseases, or symptoms thereof are treatable by specific activation of mutant-CFTR activity, e.g., activation of mutant-CFTR ion transport. ΔF508-CFTR is correlated to the presence of cystic fibrosis (CF), and a description of this disease, including its symptoms, is found in Accession No. 602421 (entitled cystic fibrosis transmembrane conductance regulator; CFTR), and Accession No. 2 19700 (entitled Cystic fibrosis; CF) of the Online Mendelian Inheritance of Man database, as found at the world wide website of the National Institute of Health at ncbi.nlm.nih.gov. Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma. Many subjects that have a mutant-CFTR protein-mediated condition are homozygous for a gene encoding a ΔF508-CFTR protein.

A "ΔF508-cystic fibrosis transmembrane conductance regulator protein" or "ΔF508-CFTR" is the protein that results from the deletion of a phenylalanine residue at amino acid position 508 of the CFTR gene product. A "ΔF508-CFTR gene" is a gene, or coding sequence, which encodes ΔF508-CFTR. A ΔF508-CFTR gene usually results from deletion of three nucleotides corresponding to the phenylalanine residue at amino acid position 508 of the encoded CFTR gene product. For the purposes of this application, the terms "genome" and "gene" are used interchangeably, e.g. "genome that encodes ΔF508-CFTR and "gene that encodes ΔF508-CFTR". For an example of a gene that encodes ΔF508-CFTR, see, e.g. WO 91102796.

A "mutant-CFTR activator" as used herein is a compound that increases the level of ion transport by a mutant-CFTR relative to ion transport in the absence of the compound, and particularly with respect to transport of chloride ions. CFTR activators of the invention of particular interest are those that are specific mutant-CFTR activators, e.g., compounds that activate mutant-CFTR activity rather than affecting CFTR cellular misprocessing. Mutant-CFTR activators are usually high-affinity mutant-CFTR activators, e.g., have an affinity for mutant-CFTR of at least about one micromolar, about one to five micromolar, about 200 nanomolar to one micromolar, about 50 nanomolar to 200 nanomolar, or below 50 nanomolar.

A "gating defective mutant-CFTR activator" as used herein is a compound that increases the level of ion transport by a gating defective mutant-CFTR relative to ion transport in the absence of the compound, and particularly with respect to transport of chloride ions. CFTR activators of the invention of particular interest are those that are specific gating defective mutant-CFTR activators, e.g., compounds that activate gating defective mutant-CFTR activity rather than affecting, for example, CFTR cellular misprocessing. Gating defective mutant-CFTR activators are usually high-affinity activators of gating defective mutant-CFTRs, e.g., have an affinity for a gating defective mutant-CFTR (e.g., ΔF508-CFTR, G551D-CFTR, G1349D-CFTR, or D1152H-CFTR) of at least about one micromolar, about one to five micromolar, about 200 nanomolar to one micromolar, about 50 nanomolar to 200 nanomolar, or below 50 nanomolar.

A "ΔF508-CFTR activator" as used herein is a compound that increases the level of ion transport by ΔF508-CFTR relative to ion transport in the absence of the compound, and particularly with respect to transport of chloride ions. CFTR activators of the invention of particular interest are those that are specific ΔF508-CFTR activators, e.g., compounds that activate ΔF508-CFTR activity rather than affecting CFTR cellular misprocessing. ΔF508-CFTR activators are usually high-affinity ΔF508-CFTR activators, e.g., have an affinity for ΔF508-CFTR of at least about one micromolar, about one to five micromolar, about 200 nanomolar to one micromolar, about 50 nanomolar to 200 nanomolar, or below 50 nanomolar.

As used herein and in the cystic fibrosis field a "potentiator" refers to a compound that increases a basal level of ion transport by a mutant-CFTR (e.g., ΔF508-CFTR, G551D-CFTR, G1349D-CFTR, or D1152H-CFTR), where the mutant CFTR (in the absence of the compound) exhibits aberrantly low levels of ion transport relative to wildtype CFTR. As such, a "mutant-CFTR potentiator" refers to a potentiator compound that provides for increased level of ion transport by a mutant-CFTR relative to ion transport capability of the mutant-CFTR in the absence of the compounds.

As used herein and in the cystic fibrosis field a "mutant-CFTR corrector" is a compound that increases the level of ion transport by a mutant-CFTR relative to ion transport in the absence of the compound by correcting the underlying defect of the CFTR polypeptide, e.g., a defect that results from post-translational mis-processing (e.g., misfolding). CFTR correctors of the invention of particular interest are those that facilitate correction of specific mutant-CFTRs. Mutant- CFTR correctors are usually exhibit high affinity for one or more mutant-CFTRs, e.g., have an affinity for mutant-CFTR of at least about one micromolar, about one to five micromolar, about 200 nanomolar to one micromolar, about 50 nanomolar to 200 nanomolar, or below 50 nanomolar.

As used herein, a "mutant-CFTR corrector-potentiator" is a compound that exhibits both mutant-CFTR corrector and potentiator activity, and usually exhibit high affinity for one or more mutant-CFTRs, e.g., have an affinity for mutant-CFTR of at least about one micromolar, about one to five micromolar, about 200 nanomolar to one micromolar, about 50 nanomolar to 200 nanomolar, or below 50 nanomolar.

The term "analog" or "analogue" refers to without limitation any compound which has structural similarity to the compounds of the invention and would be expected, by one skilled in the art, to exhibit the same or similar utility as the claimed and/or referenced compounds.

The term "derivative" refers to without limitation any compound which has a structure derived from the structure of the compounds of the present invention and whose structure is sufficiently similar to those disclosed herein and based upon that similarity, would be expected, by one skilled in the art, to exhibit the same or similar activities and utilities as the claimed and/or referenced compounds.

The term "effective amount" of a compound as provided herein is intended to mean a sufficient amount of the compound to provide the desired utility. The term "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated. Thus, as will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

"Functional group" refers to atoms or small groups of atoms (two to four) that exhibit a characteristic reactivity when treated with certain reagents, and are attached to the carbon backbone of organic molecules. The same functional group will undergo the same or similar chemical reaction(s) regardless of the size of the molecule it is a part of. Examples of functional groups include halogen, hydroxy, carboxy, ester, thioester, amino, oxime, hydrazone, thiol, azide, nitro, nitroso, aldehyde and ketone. The functional groups can be protected or unprotected, activated or unactivated.

The term "in combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated" means that a compound which has been substantially separated from, or enriched relative to, other compounds with which it occurs in nature. "Isolated" also refers to the state of a compound separated from all or some of the components that accompany it during manufacture (e.g., chemical synthesis, recombinant expression, culture medium, and the like). Isolated compounds may be present as stereoisomers, and in particular, diastereomers as well as their racemic and resolved, enantiomerically pure forms and salts thereof. Typically, an isolated compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a particular isomer of a compound of interest. Purity can be measured by any appropriate method, e.g., chromatography, mass spectroscopy, HPLC analysis, etc.

The term "optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the allyl may, but need not, be present, and the description includes situations where the heterocyclo group is mono- or disubstituted with an allyl group and situations where the heterocyclo group is not substituted with the alkyl group.

The term "organic group" and "organic radical" means any carbon containing group, including hydrocarbon groups that are classified as an aliphatic group, cyclic group, aromatic group, functionalized derivatives thereof and/or various combination thereof.

The terms "monosubstituted" refers to group with one substituent, "disubstituted" refers to group with two substituents, "trisubstituted" refers a group with three substituents, and so forth. For example, a (monosubstituted)amino refers to an amino group with one substituent, whereas a (disubstituted)amino refers to an amino group with two substituents, and whereas a (trisubstituted)amino refers to an amino group with three substitutents. When two or more substituents are present, they can be the same or different.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers. For example, a "pharmaceutically acceptable excipient," "pharmaceutically acceptable diluent," "pharmaceutically acceptable carrier," and "pharmaceutically acceptable adjuvant" includes excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use, and may include both one and more than one such excipient, diluent, carrier, and adjuvant.

The term "physiological conditions" is meant to encompass those conditions compatible with living cells, e.g., predominantly aqueous conditions of a temperature, pH, salinity, etc. that are compatible with living cells.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than DMSO. In other embodiments, the pharmaceutical compositions are suitable for administration by a route other than transdermal administration.

The term "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

The term "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, pbosphinic acids, sulfonic acids, sulfinic acids and boronic acids.

The term "pharmaceutically acceptable enol ether" of a compound of the invention means an enol ether that is pharmaceutically acceptable and that possesses the desired pharmacological activity of the parent compound, and includes, but is not limited to, derivatives of formula $C=C(OR)$ where R is hydrogen, alkyl, alkenyl, alkynyl, aryl, heteroaryl, aralkyl, heteroaralkyl, cycloalkyl or heterocyclyl.

The term "pharmaceutically acceptable enol ester" of a compound of the invention means an enol ester that is pharmaceutically acceptable and that possesses the desired pharmacological activity of the parent compound, and includes, but is not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl.

The term "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

The term "protecting group" means a chemical group introduced into a molecule by chemical modification of a functional group in order to protect or shield the functional group from its normal chemical reactivity. Protecting groups, their addition and removal are well known (W. Green, P. G. M. Wuts, Protective Groups in Organic Synthesis, Wiley-Interscience, New York, 2005). Removal of the protecting group generates the original functional group, which may be referred to as an "unprotected group".

The term "prodrugs" means any compound that releases an active parent drug according to formula (I) in vivo when such prodrug is administered to a mammalian subject. Prodrugs of a compound of formula (I) are prepared by modifying hctional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

The term "racemic" means a mixture containing approximately equal proportions of enantiomers.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on. Non-human animal models, particularly mammals, e.g. primate, murine, lagomorpha, etc. may be used for experimental investigations.

As used herein, the terms "determining," "measuring," and "assessing," and "assaying" are used interchangeably and include both quantitative and qualitative determinations.

The term "stereoisomer" means a compound with the same chemical formula and bond structure as a reference compound, but the geometrical positioning of atoms and functional groups in space differs. This class of isomers includes "enantiomers" in which different isomers are non-superimposable mirror-images of each other, and diastereomers when they are not. Enantiomers can be designated by "(+)-" versus "(−)-" when based on optical properties, or "(R)-" versus "(S)-" and or "D-" versus "L-" when based on geometric properties. For example, "D-enantiomer" and "L-enantiomer" refer to the enantiomers of a chiral system, based on the actual geometry of each enantiomer. In the context of amino acids, the enantiomer with geometry based on a naturally occurring amino acid is the L-enantiomer, whereas and the enantiomer based on a non-naturally occurring amino acid is the D-enantiomer. The term "diastereomer" refers to rotational or conformational steroisomers ("rotational isomers" or "rotomers"; and "conformational isomers" or "conformers") when the isomers can interconvert by chemical bond rotations, or cis-trans isomerism ("cis-trans isomers") when this is not possible. Stereoisomers also include "tautomers" which are structural isomers of the same chemical substance that spontaneously interconvert with each other, even when pure. Thus unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

The term "treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

The term "unit dosage form" refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

In describing the invention, the structure of the compounds of the invention will be described first. Then, pharmaceutical formulations containing the compounds will be discussed, followed by a description of their methods of use, and kits.

Compounds

The invention provides compounds and compositions containing them that correct cellular processing or folding of mutant-CFTR, such as ΔF508-CFTR, and methods of their use in treatment of mutant-CFTR-mediated diseases and conditions, e.g., cystic fibrosis. Such compounds also find use in the study of CFTR ion transport, particularly that of ΔF508-CFTR.

In one embodiment, the invention provides high-affinity small-molecule compounds that increase chloride ion (Cl⁻) conductance in cellular processing and folding defective mutant-CFTRs, such as ΔF508-CFTR. The compounds comprise a bithiazole core, an oxazole core, or a mixed thiazole-oxazole core, and multiple diversity points of substituents.

The subject compounds of the invention are generally described by formula (I) below.

(I)

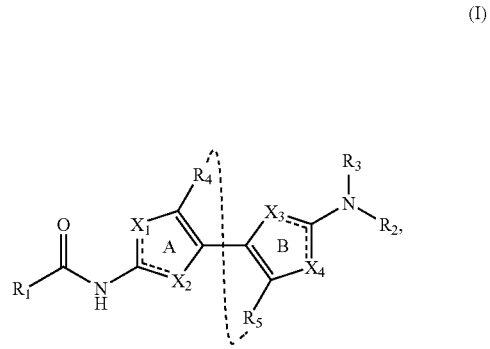

In formula (I), A and B are aromatic rings each independently selected from thiazole and oxazole, with $X_1$, $X_2$, $X_3$ and $X_4$ being heteroatoms selected from N, O and S, with each dotted line connecting $X_1$ to $X_2$ within ring A and $X_3$ to $X_4$ within ring B being a single or double bond provided that when one bond is a double bond then the other bond is a single bond, and with the dotted line connecting $R_4$ and $R_5$ indicating rotational isomers around the solid line bond connecting rings A and B. $R_1$ is a substituted or unsubstituted group selected from aliphatic and aryl, with the proviso that when $R_1$ is an unsubstituted phenyl then $R_3$ or $R_5$ is other than hydrogen. $R_2$ is a substituted or unsubstituted aryl. $R_3$ is hydrogen or substituted or unsubstituted aliphatic. $R_4$ and $R_5$ are each independently hydrogen, a substituted or unsubstituted lower aliphatic, or form a bridge comprising a heteroatom or a substituted or unsubstituted lower aliphatic chain, with the dotted line connecting $R_4$ and $R_5$ further indicating either no bridge for unbridged $R_4$ and $R_5$ or the bridge for bridged $R_4$ and $R_5$. The compounds of formula (I) may include the salts, solvates, hydrates, and prodrug forms thereof, and stereoisomers thereof.

In one embodiment, the compound of formula (I) is in a composition that contains the isolated compound. In another embodiment, the composition containing the compound is comprised as a pharmaceutical composition. The compositions generally include an effective amount of a CFTR corrector compound for correcting cellular processing or folding of a mutant-CFTR, such as ΔF508-CFTR. In particular, the pharmaceutical compositions generally include a compound that is therapeutically effective in increasing the CFTR-mediated ion permeability of a cell producing a mutant-CFTR, and the composition comprises a therapeutically effective amount of the compound for increasing the CFTR-mediated ion permeability of the cell. When provided as a pharmaceutical composition, the composition may further comprise at least one of a pharmaceutically acceptable carrier, a pharmaceutically acceptable diluent, a pharmaceutically acceptable excipient and a pharmaceutically acceptable adjuvant. The pharmaceutical preparations of the invention are described in further detail herein.

Phenyl Rings A and B, and X Substituents

In formula (I), A and B are aromatic rings each independently selected from thiazole and oxazole. Thus $X_1$, $X_2$, $X_3$ and $X_4$ are heteroatoms selected from N, O and S. For example, in ring A when $X_1$ is N, then $X_2$ must be S so as to form a thiazole. Conversely, when $X_1$ is S, then $X_2$ can be N (thiazole) or O (oxazole). The same holds true for ring B. Accordingly, each dotted line connecting $X_1$ to $X_2$ within ring A, and each dotted line connecting $X_3$ to $X_4$ within ring B represents a single or double bond, with the proviso that when one bond is a double bond then the other bond is a single bond, so as to specify the appropriate aromatic configuration of a thiazole or oxazole. Thus, a compound of formula (I) may comprise a bithiazole, a bioxazole or a mixed thiazole-oxazole core, depending on the selection of $X_1$, $X_2$, $X_3$ and $X_4$. In a specific embodiment of particular interest, aromatic rings A and B comprise a bithiazole.

Compounds of formula (I) include rotational isomers of the bithiazole, a bioxazole or a mixed thiazole-oxazole core. This is represented in formula (I) by the dotted line connecting $R_4$ and $R_5$, which indicates rotational isomers around the solid line bond connecting rings A and B. For example, the torsion angle (or dihedral angle) around the solid line bond connecting rings A and B indicates two isomeric configurations of aromatic rings A and B, as shown below.

In one embodiment, $R_1$ is an aryl group. The aryl group can be substituted or unsubstituted, and may optionally further include a spacer for attachment to the $R_1$ carbonyl of formula (I), such as a heteroatom (e.g., oxygen, nitrogen, sulfur) or other small spacer (e.g., methyl, ethyl, propyl group), and is considered as part of a substituted aryl in this context. In a specific embodiment, $R_1$ is an aryl group comprising a phenyl. The phenyl moiety can be an unsubstituted or substituted phenyl. Examples of substituted phenyls of particular interest include, but are note limited to, o-chloro-phenyl, m-chloro-phenyl, p-chloro-phenyl, p-nitro-phenyl, and p-amino-phenyl.

In certain other embodiments, $R_1$ is an aryl group comprising a substituted or unsubstituted heteroaryl, and may optionally further include a spacer for attachment to the $R_1$ carbonyl of formula (I), such as a heteroatom (e.g., oxygen, nitrogen, sulfur) or other small spacer (e.g., methyl, ethyl, propyl group), and is considered as part of a substituted heteroaryl in this context. Examples of $R_1$ heteroaryl groups of particular interest include, but are not limited to, a substituted or unsubstituted furanyl, or a substituted or unsubstituted [2,4,6]triazine, such as 3,5-Dichloro-[2,4,6]triazine-1-yl.

In another embodiment, $R_1$ is a substituted or unsubstituted aliphatic. The $R_1$ aliphatic may optionally further include a spacer for attachment to the $R_1$ carbonyl of formula (I), such as a heteroatom (e.g., oxygen, nitrogen, sulfur) or other small spacer, and is considered as part of a substituted aliphatic in this context. $R_1$ aliphatics of particular interest are selected from a substituted or unsubstituted alkyl and a substituted or unsubstituted alkenyl. Specific examples of $R_1$ include, but are not limited to, ethyl, propyl, 3-butenyl, 1-methyl-propyl, t-butyl, isobutyl, pentyl, 1-methyl-butyl, hexyl, and bromo-methyl.

A featured aspect of the invention are compounds of formula (I) where $R_1$ is selected from ethyl, propyl, 3-butenyl, 1-methyl-propyl, t-butyl, isobutyl, pentyl, 1-methyl-butyl, hexyl, bromo-methyl, phenyl, o-chloro-phenyl, m-chloro-phenyl, p-chloro-phenyl, p-nitro-phenyl, p-amino-phenyl, furanyl, and 3,5-Dichloro-[2,4,6]triazine-1-yl.

In some embodiments, the $R_1$ may further comprise a linker. The linker may serve one or more purposes, such as forming a prodrug version of the compound, altering the solubility of the compound in water or other solvent, modifying one or more pharmacokinetic parameters of the compound, attaching the compound to a surface, conjugation to a second compound, and the like. Thus the linker is typically chosen for a given end use. For example, the linker may be

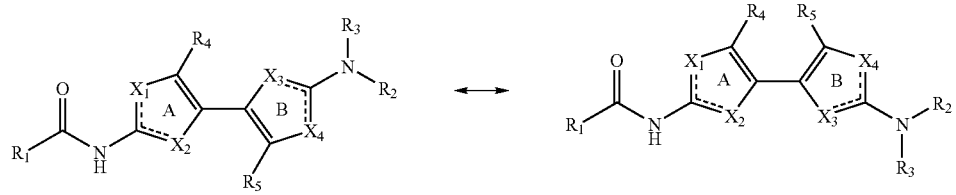

where A, B, $X_1$, $X_2$, $X_3$, $X_4$, $R_1$, $R_2$, $R_3$, $R_4$ and $R_5$ are as defined in formula (I). Rotational isomers of particular interest are described in more detail herein.

$R_1$ Substituents

As noted above, $R_1$ is a substituted or unsubstituted group selected from aliphatic and aryl, with the proviso that when the $R_1$ aryl group is an unsubstituted phenyl then $R_3$ or $R_5$ is other than hydrogen.

exploited to conjugate a compound of formula (I) to a second molecule so as to incorporate the properties of the second molecule.

Thus in certain embodiments, the linker of the $R_1$ substituent is conjugated to a second molecule. Of particular interest is second molecule comprising a CFTR potentiator compound. Examples of CFTR potentiator compounds of interest are the phenylglycine containing and sulfonamide containing compounds described in WO 2005/120497, and the potentiators described in co-pending U.S. provisional patent application Ser. No. 60/980,387, filed Oct. 16, 2007, entitled "Compounds Having Activity In Increasing Ion Transport By Mutant-CFTR And Uses Thereof", each of which are incorporated here by reference in its entirety, and further herein in the Examples. A specific example is the potentiator compound PG01.

In a specific embodiment, $R_1$ comprises a substituted phenyl, where the phenyl is the linker and comprises a portion of a component of a second molecule, such as with the compound YMX described herein. In other embodiments, the compound of formula (I) is conjugated to a portion of second molecule either directly or through reaction with a functional group, such as an amino, hydroxyl or carboxyl group. The linker may also be conjugated to the second molecule by or biodegradable bond, such as an ester bond. In some embodiments, when $R_1$ comprises a linker conjugated to a second molecule through a biodegradable bond, then the subject compound can be a prodrug. For instance, exposure of a compound with such biodegradable bond can result in the degradation and thus cleavage of the bond in a chemical or biological system, particularly in vivo, via chemical hydrolysis and/or enzymatic hydrolysis. Removal of the linker in part or in whole can then release the core drug as appropriate.

Other linkers can be employed as well for a given end use. For example, linkers of particular interest comprise a straight or branched aliphatic chain, and may optionally include one or more heteroatoms in the main chain, or contain one or more substituents in place of a hydrogen on a carbon of the linker. Of specific interest are short chain linkers, such as alkyl and ethylene oxide containing chains that comprise 1 to 20 carbons, 1-15 carbons, 1-10 carbons, and particularly 1-8 carbons or less.

Featured short chain linkers comprise the ethylene oxide radical —(O—$CH_2$—$CH_2$)$_n$—, where n is 1-10, 1-9, 1-8, 1-7, 1-6, 1-6, 1-4, 1-3, or 1-2, which can terminate with a variety of groups, such as functional group, protecting group, methoxy, ethoxy and the like, or be conjugated directly or through a residue of a functional group to a second molecule. Examples include "PEG" based linkers, which are well known in the art. A specific example is [2-(2-hydroxy-ethoxy)-ethoxy]-acetic acid, in protected or unprotected form, which is conjugated to an $R_1$ phenyl though an ether linkage (e.g., phenyl-O—($CH_2$)$_2$—O—$CH_2$—$CH_2$—O—$CH_2$—C(O)OH or phenyl-O—($CH_2$)$_2$—O—$CH_2$—$CH_2$—$CH_2$—C(O)O—C($CH_3$)$_3$, where the phenyl is bonded directly to the $R_1$ amide of formula (I)). As such, a particular example in this embodiment is where $R_2$ is ({2-[2-(phenoxy)-ethoxy]-ethoxy}-acetic acid)-4-yl or ({2-[2-(phenoxy)-ethoxy]-ethoxy}-acetic acid ter-butyl ester)-4-yl.

$R_2$ Substituents $R_2$ is a substituted or unsubstituted aryl group. The $R_2$ aryl group can be substituted or unsubstituted, and may optionally further include a spacer for attachment to the $R_2$/$R_3$ nitrogen of formula (I), such as a heteroatom (e.g., oxygen, nitrogen) or other small spacer (e.g., methyl or carbonyl group), and considered as part of a substituted aryl in this context. In a specific embodiment, $R_2$ is an aryl group comprising a phenyl, which can be unsubstituted or substituted. Examples of $R_2$ groups of particular interest include, but are note limited to, a substituted phenyl selected from p-methyl phenyl; m-fluoro phenyl; m-methoxy phenyl; 5-chloro-2-methyl phenyl; o-methyl phenyl; p-fluoro phenyl; 2,5-dichloro phenyl; p-methoxy phenyl; o-methoxy phenyl; 2,4-dichloro phenyl; 2-methoxy-3-chloro phenyl; 2-methoxy-5-chloro phenyl; 2,5-dimethoxy phenyl; o-ethoxy phenyl; o-ethoxy nitrophenyl; o-ethoxy aminophenyl; o-ethoxy azidophenyl; and 2-hydroxy-4-chloro phenyl.

In other embodiments, $R_2$ is an aryl comprising a substituted or unsubstituted heteroaryl. Examples of $R_2$ heteroaryl of specific interest include, but are not limited to, a substituted or unsubstituted [2,4,6]triazine, such as 3,5-Dichloro-[2,4,6]triazine-1-yl.

A featured aspect of the invention are compounds of formula (I) where $R_2$ is selected from the group consisting of p-methyl phenyl; m-fluoro phenyl; m-methoxy phenyl; 5-chloro-2-methyl phenyl; o-methyl phenyl; p-fluoro phenyl; p-chloro phenyl; 2,5-dichloro phenyl; p-methoxy phenyl; o-methoxy phenyl; 2,4-dichloro phenyl; 2-methoxy-3-chloro phenyl; 2-methoxy-5-chloro phenyl; 2,5-dimethoxy phenyl; o-ethoxy phenyl; o-ethoxy nitrophenyl; o-ethoxy aminophenyl; o-ethoxy azidophenyl; 2-hydroxy-4-chloro phenyl; 3,5-Dichloro-[2,4,6]triazine-1-yl; ({2-[2-(4-chlorophenoxy)-ethoxy]-ethoxy}-acetic acid)-6yl; and ({2-[2-(4-chlorophenoxy)-ethoxy]-ethoxy}-acetic acid tert-butyl ester)-6yl.

As with $R_1$, the $R_2$ substituent may comprise a linker. Again, the linker may serve one or more purposes, such as forming a prodrug version of the compound, altering the solubility of the compound in water or other solvent, modifying one or more pharmacokinetic parameters of the compound, attaching the compound to a surface, conjugation to a second compound, and the like. A specific example is where $R_2$ comprises a phenyl substituted with a [2-(2-hydroxy-ethoxy)-ethoxy]-acetic acid linker, which linker many be in protected or unprotected form, and which is conjugated to this phenyl though an ether linkage (e.g., phenyl-O—($CH_2$)$_2$—O—$CH_2$—$CH_2$—O—$CH_2$—C(O)OH or phenyl-O—($CH_2$)$_2$—O—$CH_2$—$CH_2$—O—$CH_2$—C(O)O—C($CH_3$)$_3$, where the phenyl is bonded directly to the $R_2$/$R_3$ amine in formula (I)). As such, a particular example in this embodiment is where $R_2$ is ({2-[2-(4-chlorophenoxy)-ethoxy]-ethoxy}-acetic acid)-6yl; and ([2-[2-(4-chlorophenoxy)-ethoxy]-ethoxy]-acetic acid tert-butyl ester)-6yl.

Thus in a related embodiment, $R_2$ comprises a linker conjugated to a second molecule, such as a CFTR potentiator compound as described above for $R_1$. In a specific embodiment, $R_2$ comprises a substituted phenyl that comprises a linker, where the linker is conjugated to the second molecule by a biodegradable bond, such as an ester bond, as exemplified by the compound YM1.4 described further herein below. In some embodiments, when $R_2$ comprises a linker conjugated to a second molecule through a biodegradable bond, then the subject compound can be a prodrug.

$R_3$ Substituents

The $R_3$ substituent of a formula (I) compound of the invention can be hydrogen or substituted or unsubstituted aliphatic. Compounds of particular interest are those where $R_3$ is hydrogen. In certain embodiments, $R_3$ comprises a substituted or unsubstituted aliphatic, such as a linker. As with $R_1$ and $R_2$, the linker may serve one or more purposes, such as forming a prodrug version of the compound, altering the solubility of the compound in water or other solvent, modifying one or more pharmacokinetic parameters of the compound, attaching the compound to a surface, conjugation to a second compound, and the like. In a specific embodiment, $R_3$ comprises a linker and is a radical selected from —($CH_2$)$_2$—O—$CH_2$—$CH_2$—O—$CH_2$—C(O)OH and —($CH_2$)$_2$—O—$CH_2$—$CH_2$—O—$CH_2$—C(O)O—C($CH_3$)$_3$. A specific example is where $R_2$ is substituted with a [2-(2-hydroxy-ethoxy)-ethoxy]-acetic acid linker, which linker many be in protected or unprotected form, and which when conjugated is bonded to the $R_3$ nitrogen as an amine linkage (e.g., N—($CH_2$)$_2$—O—

CH₂—CH₂—O—CH₂—C(O)OH or N—(CH₂)₂—O—CH₂—CH₂—O—CH₂—C(O)O—C(CH₃)₃, where N is the R₂/R₃ nitrogen of formula (I). As such, a particular example in this embodiment is where R₃ is (2-ethoxy-ethoxy)-acetic acid or (2-ethoxy-ethoxy)-acetic acid tert-butyl ester.

R₄ and R₅ Substituents—Bridged and Unbridged Compounds of Formula (I)

As represented in formula (I), R₄ and R₅ are each independently hydrogen, a substituted or unsubstituted lower aliphatic, or form a bridge comprising a heteroatom or a substituted or unsubstituted lower aliphatic chain, with the dotted line connecting R₄ and R₅ further indicating either no bridge for unbridged R₄ and R₅ or the bridge for bridged R₄ and R₅.

Unbridged Compounds of Formula (II)

In one embodiment, R₄ and R₅ are unbridged, and the compound of formula (I) comprises formula (II):

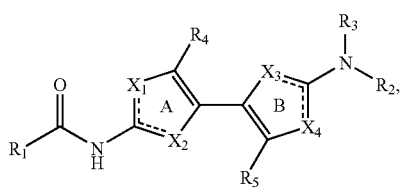

(II)

or the salts, solvates, hydrates, and prodrug forms thereof, and stereoisomers thereof, wherein X₁, X₂, X₃, X₄, R₁, R₂ and R₃ are as defined in formula (I), and wherein R₄ and R₅ are each independently hydrogen or a substituted or unsubstituted lower aliphatic. Thus compounds of formula (II) do not contain a bridge connecting R₄ and R₅, and include compounds representing each rotational isomer around the solid line bond connecting rings A and B.

In one embodiment, R₄ and R₅ are each independently hydrogen or a lower aliphatic, such as methyl and ethyl. In another embodiment, R₄ and R₅ are selected from hydrogen and methyl. An additional embodiment is where R₄ is methyl and R₅ is hydrogen. Yet another embodiment is where both R₄ and R₅ are hydrogen.

A compound of formula (II) may also be provided as a pharmaceutical preparation in which the salts, solvates, hydrates, and prodrug forms thereof, and stereoisomers thereof, comprise the pharmaceutically acceptable salts, solvates, hydrates, and prodrug forms thereof, and stereoisomers thereof.

As noted above, a compound according to formula (II) is non-bridged, i.e., R₄ and R₅ are unbridged, and each independently chosen from hydrogen or a substituted or unsubstituted lower aliphatic. Exemplary compounds of formula (II) are those where aromatic rings A and B comprise a bithiazole, and where R₁ is a substituted or unsubstituted aliphatic, or a substituted or unsubstituted phenyl, R₂ is a substituted phenyl, and R₃ is hydrogen.

In one embodiment, the compound is of formula (II), where aromatic rings A and B comprise a bithiazole, and wherein: R₁ is selected from t-butyl, bromo-methyl, hexyl, phenyl, p-chloro-penyl, p-nitro-phenyl and p-amino-phenyl; R₂ is selected from p-methyl-phenyl, p-chloro-phenyl, 2,5-dimethoxy-phenyl, 2-methoxy-5-chloro phenyl, 2-methoxy-phenyl, 2-ethoxy-phenyl, ({2-[2-(4-chlorophenoxy)-ethoxy]-ethoxy}-acetic acid)-6yl; and ({2-[2-(4-chlorophenoxy)-ethoxy]-ethoxy}-acetic acid tert-butyl ester)-6yl; R₃ is hydrogen; R₄ is selected from hydrogen and methyl; and R₅ is hydrogen.

In certain specific embodiments, the compound is of formula (II), where aromatic rings A and B comprise a bithiazole, and wherein R₁ is t-butyl, R₂ is a substituted phenyl, R₄ is hydrogen or methyl, and R₃ and R₅ are hydrogen. In other specific embodiments, the compound is of formula (II), wherein aromatic rings A and B comprise a bithiazole, and wherein R₁ is t-butyl, R₂ is 2-methoxy-3-chloro phenyl, R₄ is hydrogen or methyl, and R₃ and R₅ are hydrogen. In additional specific embodiments, the compound is of formula (II), wherein aromatic rings A and B comprise a bithiazole, and wherein R₁ is t-butyl, R₂ is 2-methoxy-3-chloro phenyl, R₄ is methyl, and R₃ and R₅ are hydrogen.

Featured compounds of formula (II) include those wherein aromatic rings A and B comprise a bithiazole in which X₁ is N, X₂ is S, X₃ is N, and X₄ is S, R₁ is t-butyl, bromo-methyl, hexyl, phenyl, p-chloro-penyl, p-nitro-phenyl p-amino-phenyl, or p-amidolinker-phenyl conjugated to a second compound R (such as a potentiator compound), R₂ is selected from p-methyl-phenyl, p-chloro-phenyl, O-methyl, O-ethoxy, hydroxyl, 2,5-dimethoxy-phenyl, 2-methoxy-5-chloro phenyl, 5-chloro-2-linker-phenyl, R₃ is hydrogen or linker, and, R₄ is methyl, and R₅ is hydrogen, such as a compound selected from:

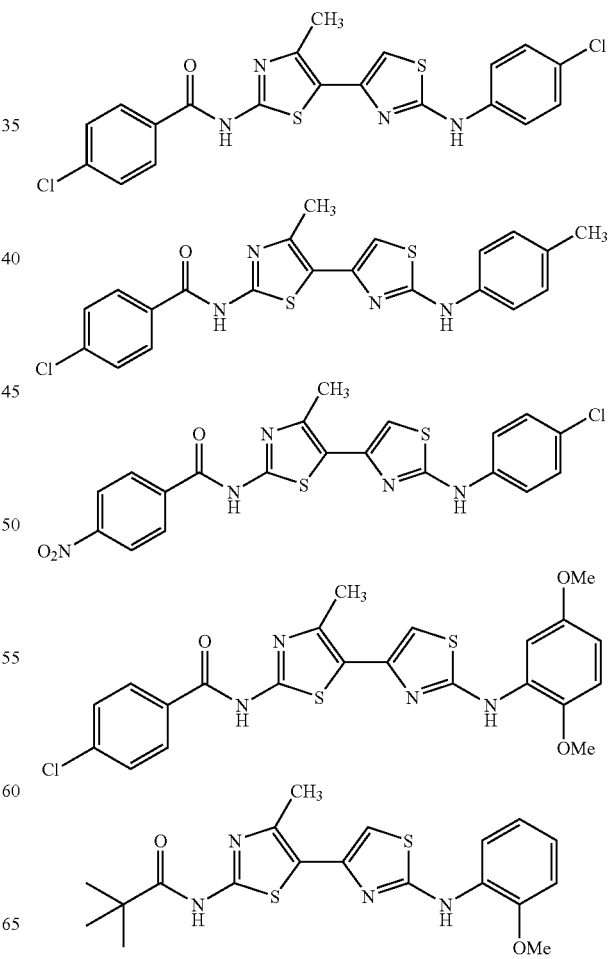

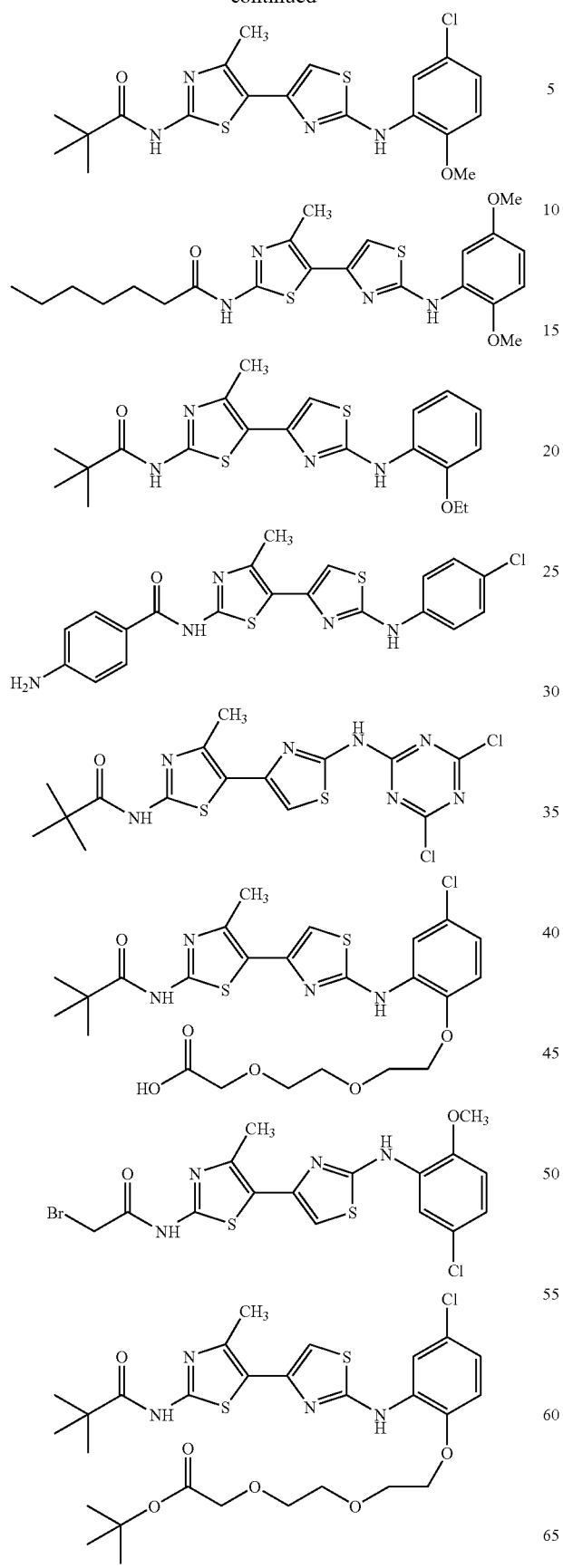

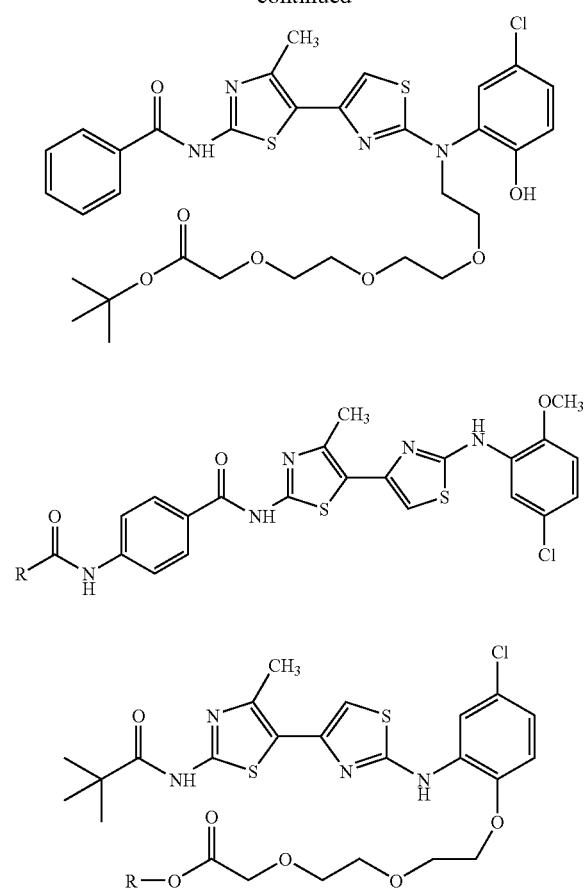

or a derivative thereof, the salts, solvates, hydrates, and prodrug forms thereof, and stereoisomers thereof. In one embodiment, R is a mutant-CFTR potentiator compound or fragment thereof.

Other featured compounds of formula (II) include those where aromatic rings A and B comprise a bithiazole in which $X_1$ is N, $X_2$ is S, $X_3$ is N, and $X_4$ is S, $R_1$ ethyl, $R_2$ is an amino-, nitro- or azido-substituted 2-ethoxyphenyl, $R_3$ and $R_5$ are hydrogen, $R_4$ is methyl, and wherein the compound comprises a detectably labeled version or an intermediate thereof, such as a compound selected from:

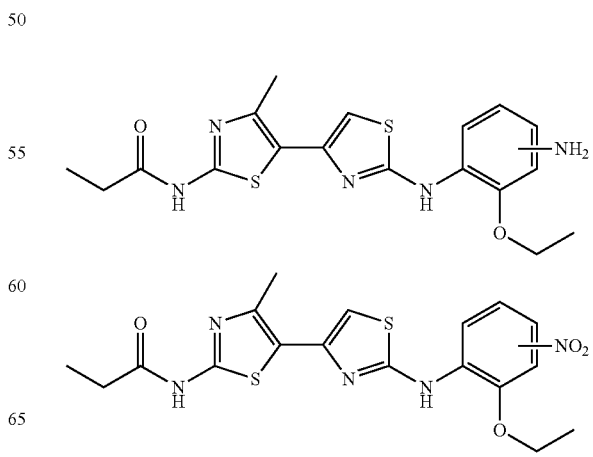

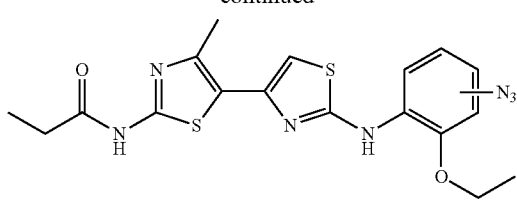

or a derivative thereof, the salts, solvates, hydrates, and prodrug forms thereof, and stereoisomers thereof.

Additional embodiments exemplifying a compound of formula (II), include those where aromatic rings A and B comprise a bithiazole in which $X_1$ is N or S, $X_2$ is N or S, $X_3$ is N or S, and $X_4$ is N or S, wherein $R_1$ is t-butyl, $R_2$ is 2-methoxy-5-chlorophenyl, $R_3$ is hydrogen, $R_4$ is hydrogen, methyl or ethyl, and $R_5$ is hydrogen or methyl, such as a compound selected from:

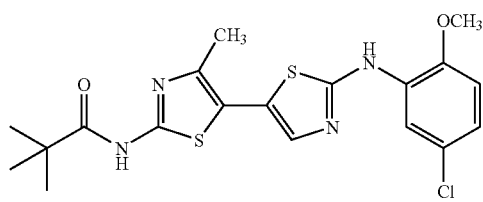

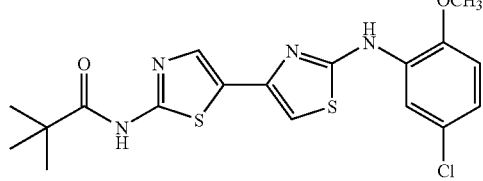

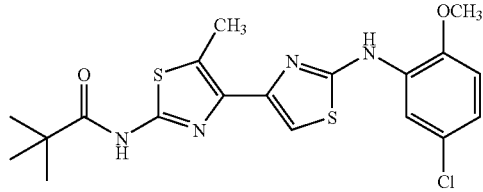

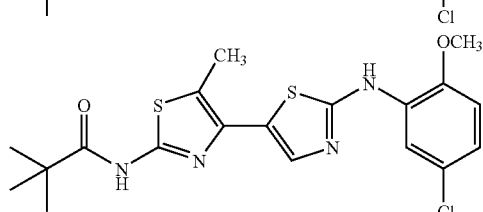

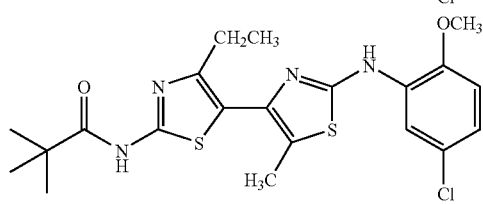

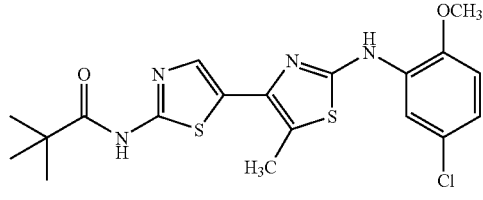

or a derivative thereof, the salts, solvates, hydrates, and prodrug forms thereof, and stereoisomers thereof.

Bridged Compounds of Formula (III)

In one embodiment, $R_4$ and $R_5$ are bridged, and the compound of formula (I) comprises formula (III):

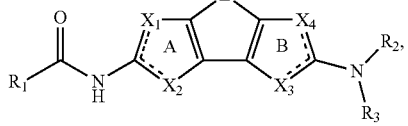

(III)

or the salts, solvates, hydrates, and prodrug forms thereof, and stereoisomers thereof, wherein $X_1$, $X_2$, $X_3$, $X_4$, $R_1$, $R_2$ and $R_3$ are as defined in formula (I), and wherein Z is the bridge comprising a heteroatom or a substituted or unsubstituted lower aliphatic chain.

As noted above, a compound according to formula (III) is bridged, i.e., $R_4$ and $R_5$ form a bridge comprising a heteroatom or a substituted or unsubstituted lower aliphatic chain. In this context, "bridged" is intended to mean a single substituted or unsubstituted atom, or two or more substituted or unsubstituted atoms that form a chemically bonded system.

As also noted above, a compound of formula (III) may also be provided as a pharmaceutical preparation in which the salts, solvates, hydrates, and prodrug forms thereof, and stereoisomers thereof, comprise the pharmaceutically acceptable salts, solvates, hydrates, and prodrug forms thereof, and stereoisomers thereof.

In one embodiment, Z is a straight or branched lower aliphatic chain, and may optionally include one or more heteroatoms in the main chain, or contain one or more substituents in place of a hydrogen on a carbon of the chain. Of specific interest are short chains, such as a chain containing 1-5 carbons, 1-4 carbons, 1-3 carbons, 1-2 carbons or a single carbon. In another embodiment, the compound is of formula (III), and Z is comprises a heteroatom selected from N, O and S. In a specific embodiment, Z is O. Thus, a bridged compound according to formula (III) include those where Z is a substituted or unsubstituted lower aliphatic chain, such as when Z is methyl, ethyl, propyl, isopropyl, butyl or isobutyl, or such as when Z is oxygen, methoxy, ethoxy, propoxy, butoxy and the like.

Exemplary compounds of formula (III) also include those where aromatic rings A and B comprise a bithiazole, and wherein $R_1$ is a substituted or unsubstituted aliphatic, or a substituted or unsubstituted phenyl, $R_2$ is a substituted phenyl, and $R_3$ is hydrogen.

In one embodiment, the compound is of formula (III), where $R_1$ is selected from t-butyl, bromo-methyl, hexyl, phenyl, p-chloro-penyl, p-nitro-phenyl and p-amino-phenyl; $R_2$ is selected from p-methyl-phenyl, p-chloro-phenyl, 2,5-dimethoxy-phenyl, 2-methoxy-5-chloro phenyl, 2-methoxy-phenyl, 2-ethoxy-phenyl, ({2-[2-(4-chlorophenoxy)-ethoxy]-ethoxy}-acetic acid)-6yl; and ({2-[2-(4-chlorophenoxy)-ethoxy]-ethoxy}-acetic acid tert-butyl ester)-6yl; $R_3$ is hydrogen; and Z is selected from methyl, ethyl, propyl, isopropyl, butyl and isobutyl.

In certain specific embodiments, the compound is of formula (III), where aromatic rings A and B comprise a bithiazole, and wherein $R_1$ is phenyl, $R_2$ is 2-methoxy-3-chloro phenyl, and $R_3$ is hydrogen. In other specific embodiments, the compound is of formula (III), where aromatic rings A and B comprise a bithiazole, and wherein $R_1$ is t-butyl, $R_2$ is a substituted phenyl, and $R_3$ is hydrogen. In additional specific embodiments, the compound is of formula (III), where aromatic rings A and B comprise a bithiazole, and wherein $R_1$ is t-butyl, $R_2$ is 2-methoxy-3-chloro phenyl, and $R_3$ is hydrogen. Another specific embodiment is where the compound is of formula (III), and where aromatic rings A and B comprise a bithiazole, and wherein $R_1$ is t-butyl, $R_2$ is 2-methoxy-3-chloro phenyl, $R_4$ is methyl, and $R_3$ and $R_5$ are hydrogen.

Featured compounds of formula (III) include those wherein aromatic rings A and B comprise a bithiazole in which $X_1$ is N or S, $X_2$ is S or N, $X_3$ is N or S, and $X_4$ is S or N, $R_1$ is t-butyl, $R_2$ is 2-methoxy-5-chlorophenyl, $R_3$ is hydrogen, and Z is methyl, ethyl, propyl, butyl, or isobutyl, and such as a compound selected from:

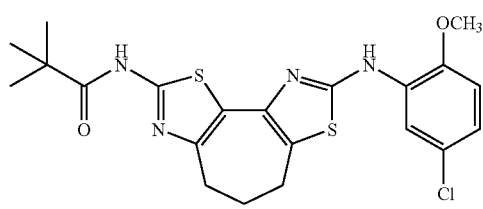

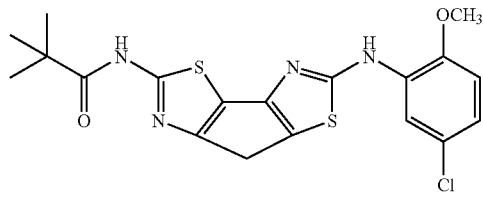

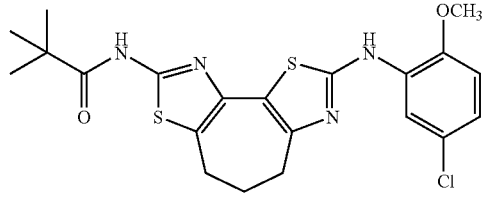

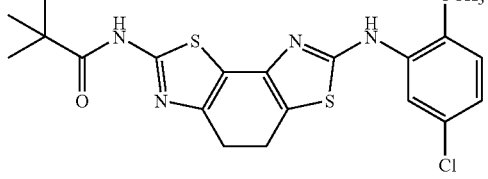

-continued

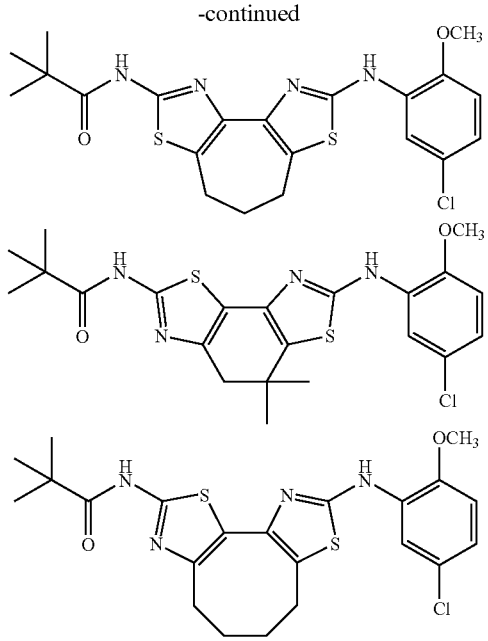

or a derivative thereof, the salts, solvates, hydrates, and prodrug forms thereof, and stereoisomers thereof.

s-Cis Bithiazoles

One embodiment provides composition comprising a compound of the formula:

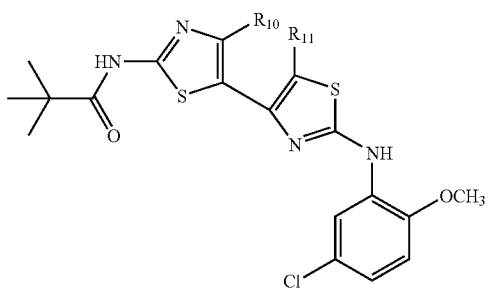

S wherein $R_{10}$ and $R_{11}$ are independently selected from hydrogen and $C_1$-$C_4$ alkyl; or $R_{10}$ and $R_{11}$ are combined to form a ring of six to eight carbons;

or salt, solvate, hydrate, or prodrug form thereof, or stereoisomers thereof.

A featured composition comprises a compound of the formula:

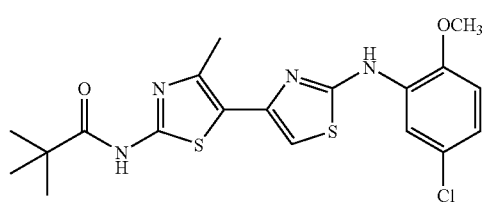 [SMILES: COc1ccc(Cl)cc1Nc1nc(-c2sc(NC(=O)C(C)(C)C)nc2C)cs1]

or salt, solvate, hydrate, or prodrug form thereof, or stereoisomers thereof.

Another featured composition comprises a compound of the formula:

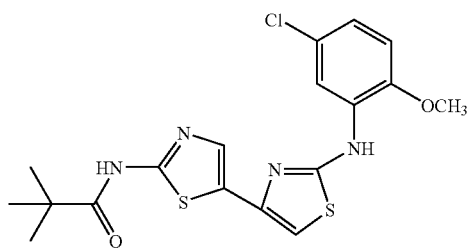 [SMILES: COc1ccc(Cl)cc1Nc1nc(-c2cnc(NC(=O)C(C)(C)C)s2)cs1]

or salt, solvate, hydrate, or prodrug form thereof, or stereoisomers thereof.

Another featured composition comprises a compound of the formula:

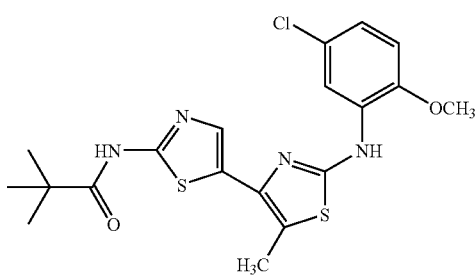 [SMILES: COc1ccc(Cl)cc1Nc1nc(-c2cnc(NC(=O)C(C)(C)C)s2)c(C)s1]

or salt, solvate, hydrate, or prodrug form thereof, or stereoisomers thereof.

Another featured composition comprises a compound of the formula:

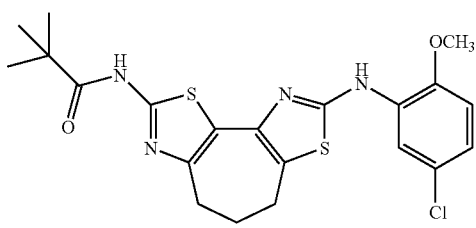 [SMILES: COc1ccc(Cl)cc1Nc1nc2c(s1)CCCc1nc(NC(=O)C(C)(C)C)sc1-2]

or salt, solvate, hydrate, or prodrug form thereof, or stereoisomers thereof.

Hybrid Corrector-Potentiator Compounds

As noted above, compounds of formula (I) include some embodiments in which $R_1$ or $R_2$ comprise a linker conjugated to a second molecule. As also noted above, a particular second molecule of interest is a potentiator compound that increases ion transport mediated by a gating defective mutant-CFTR such as ΔF508-CFTR, G551 D-CFTR, G1349D-CFTR, and D1152H-CFTR.

In this context, hybrid compounds according to formula (I) comprise a single chemical entity containing both corrector and potentiator structural motifs so as to provide an expanded range of pharmaceutical activity for treating both gating and processing/folding mutants of CFTR. Potentiator compounds of particular interest are described in WO 2005/120497 and co-pending U.S. provisional patent application Ser. No. 60/980,387, filed Oct. 16, 2007, entitled "Compounds Having Activity In Increasing Ion Transport By Mutant-CFTR And Uses Thereof", each of which are incorporated herein by reference in its entirety.

In one embodiment, a hybrid compound of the invention comprises a hybrid corrector-potentiator compound of formula (IV):

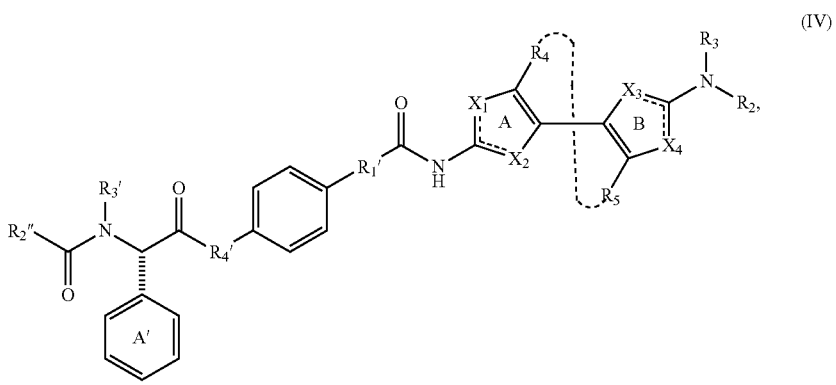

(IV)

or the salts, solvates, hydrates, and prodrug forms thereof, and stereoisomers thereof, wherein: A, B, $X_1$, $X_2$, $X_3$, $X_4$, $R_2$, $R_3$, $R_4$ and $R_5$ are as defined in formula (I), wherein $R_1'$ is a present or absent, and when present is a linker, and wherein A' is a racemic phenyl comprising L- and D-enantiomers as indicated by the hashed bond; $R_2''$ is an alkoxy, a substituted or unsubstituted phenyl, or a substituted or unsubstituted heterocycle, and is bonded to the $R_2''$ carbonyl either directly or by a spacer comprising 1 to 5 carbons; $R_3'$ is hydrogen or methyl; and $R_4'$ is O or NH.

In another embodiment, a hybrid compound of the invention comprises a hybrid corrector-potentiator compound of formula (V):

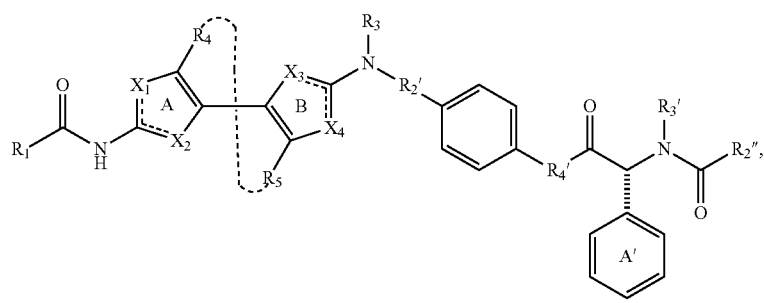

(V)

or the salts, solvates, hydrates, and prodrug forms thereof, and stereoisomers thereof, wherein: A, B, $X_1$, $X_2$, $X_3$, $X_4$, $R_1$, $R_3$, $R_4$ and $R_5$ are as defined in formula (I), wherein $R_2'$ is a present or absent, and when present is a linker, and wherein A' is a racemic phenyl comprising L- and D-enantiomers as indicated by the hashed bond; $R_2''$ is an alkoxy, a substituted or unsubstituted phenyl, or a substituted or unsubstituted heterocycle, and is bonded to the $R_2''$ carbonyl either directly or by a spacer comprising 1 to 5 carbons; $R_3'$ is hydrogen or methyl; and $R_4'$ is O or NH.

In one embodiment, the compound of formula (I) is in a composition that contains the isolated compound. In another embodiment, the composition containing the compound is comprised as a pharmaceutical composition. The compositions generally include an effective amount of a CFTR potentiator-corrector compound for correcting cellular processing or folding and potentiating a gating defective mutant-CFTR, such as ΔF508-CFTR, G551D-CFTR, G1349D-CFTR, or D1152H-CFTR. In particular, the pharmaceutical compositions generally include a compound that is therapeutically effective in increasing the CFTR-mediated ion permeability of a cell producing a mutant-CFTR, and the composition comprises a therapeutically effective amount of the compound for increasing the CFTR-mediated ion permeability of the cell. When provided as a pharmaceutical composition, the composition may further comprise at least one of a pharmaceutically acceptable carrier, a pharmaceutically acceptable diluent, a pharmaceutically acceptable excipient and a pharmaceutically acceptable adjuvant. The pharmaceutical preparations of the invention are described in further detail herein.

As noted in formulas (IV) and (V), the $R_2''$ group is a substituted or unsubstituted alkoxy, a substituted or unsubstituted phenyl, or a substituted or unsubstituted heterocycle, and is bonded to the $R_2''$ carbonyl either directly or by a spacer comprising 1 to 5 carbons. The spacer can be straight or branched carbon chains, and may optionally include one or more heteroatoms in the main chain, or contain one or more substituents in place of a hydrogen on a carbon of the spacer. Of particular interest are simple alkyl-based carbon chains that comprise 1 to 5 carbons, 1-4 carbons, and particularly 1-3 carbons or less. The featured spacers comprise a radical selected from —$CH_2$—, —$CH_2$—$CH_2$—, and —$CH_2$—$CH_2$—$CH_2$—.

In one embodiment, $R_2''$ is a substituted or unsubstituted alkoxy group. In a specific embodiment, the alkoxy group is selected from methoxy, ethoxy, n-propoxy, isopropoxy, n-butoxy, tert-butoxy, sec-butoxy, n-pentoxy, n-hexoxy, and 1,2-dimethylbutoxy. A particular alkoxy $R_2''$ group of interest is tert-butoxy, which comprises a t-butyl carbamate ("Boc") group in the context of the $R_2''$ carbonyl. In other embodiments, $R_2''$ is a substituted alkoxy group, such as an alkoxyamino, alkoxycarbonyl, or alkoxycarbonylamino. Examples of substituted alkoxy include the radicals —N(H)O-alkyl, —N(H)O-cycloalkyl, —C(O)-alkoxy, and —NRC(O)OR' where in this context R is hydrogen, alkyl, aryl or cycloalkyl, and R' is alkyl or cycloalkyl.

In another embodiment, $R_2''$ comprises a phenyl group, which can be an unsubstituted phenyl such as benzyl, or a substituted phenyl, such as phenol (e.g., phenol-2-yl or phenol-4-yl) or aniline (e.g., aniline-3-yl or (benzoimidazol-2-yl)-aniline-3-yl)). In this embodiment, the unsubstituted or substituted phenyl is bonded to the $R_2''$ carbonyl of formula (I) either directly or by a spacer comprising 1 to 5 carbons. For example, in a specific embodiment, $R_2''$ is an unsubstituted phenyl that comprises a one carbon spacer, such as benzyl. In another specific embodiment, the substituted phenyl is a phenol comprising a one carbon spacer, such as (phenol-4-yl)-methyl, or a two carbon spacer such as (phenol-2-yl)-ethyl or (phenol-4-yl)-ethyl. Alternatively, $R_2''$ can be directly attached to the $R_2''$ carbonyl of formula (I), for instance, as with a substituted phenyl comprising the aniline derivative (benzoimidazol-2-yl)-aniline-3-yl.

In a specific embodiment, $R_2''$ is a substituted or unsubstituted heterocycle selected from indole, pyrrole, pyrazine, indazole and pyrrolidone, that is connected directly or by a spacer to the $R_2''$ carbonyl of formula (I). Examples of $R_2''$ heterocycle groups without a spacer include, but are not limited to, pyrrole-1-yl, pyrazine-2-yl, indazole-6-yl, pyrrolidone-5-yl, 5-methyl-pyrazine-2-yl, 3-methoxy-2-methyl-2H-indazole-6-yl, and pyrrolidin-2-one-5-yl. Examples of $R_2''$ heterocycle groups that include a spacer and are substituted with a water soluble group include, but are not limited to, (5-azidoindole-3-yl)-methyl, (indole-3-yl)-methyl, (5-carboxymethylindole-3-yl)-methyl, (5-carboxymethoxy-indole-3-yl)-methyl, and (5-hydroxyindole-3-yl)-methyl.

In formulas (IV) and (V), $R_1'$ and $R_2'$ are absent or comprise a linker. Examples of linkers of particular interest comprise a heteroatom, or a straight or branched aliphatic chain, and may optionally include one or more heteroatoms in the main chain, or contain one or more substituents in place of a hydrogen on a carbon of the linker, such as described herein. Of specific interest are short chain linkers, such as alkyl and ethylene oxide containing chains that comprise 1 to 20 carbons, 1-15 carbons, 1-10 carbons, and particularly 1-8 carbons or less.

A featured compound of formula (IV) include those wherein aromatic rings A and B comprise a bithiazole in which $X_1$ is N or S, $X_2$ is S or N, $X_3$ is N or S, and $X_4$ is S or N, $R_1$ is phenyl, $R_1'$ is absent, $R_3$ is methyl, $R_4$ is methyl, and wherein A' is the D-enantiomer, $R_2''$ is (indole-3-yl)-methyl, and $R_4'$ is NH, such as a hybrid compound YMX depicted below:

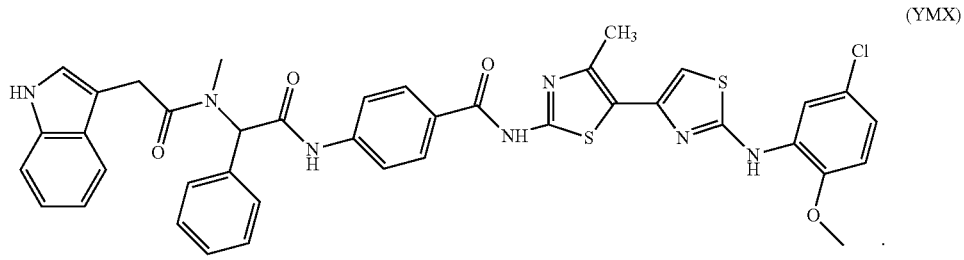 [SMILES: COc1ccc(Cl)cc1Nc1nc(-c2sc(NC(=O)c3ccc(NC(=O)C(c4ccccc4)N(C)C(=O)Cc4c[nH]c5ccccc45)cc3)nc2C)cs1]

(YMX)

A featured compound of formula (V) include those wherein aromatic rings A and B comprise a bithiazole in which $X_1$ is N or S, $X_2$ is S or N, $X_3$ is N or S, and $X_4$ is S or N, $R_1$ is phenyl, $R_2'$ is a linker comprising an ethoxy radical —O—CH$_2$—CH$_2$—, $R_3$ is methyl, $R_4$ is methyl, and wherein A' is the D-enantiomer, $R_2''$ is (indole-3-yl)-methyl, and $R_4'$ is NH, such as a hybrid compound YM1.4 depicted below:

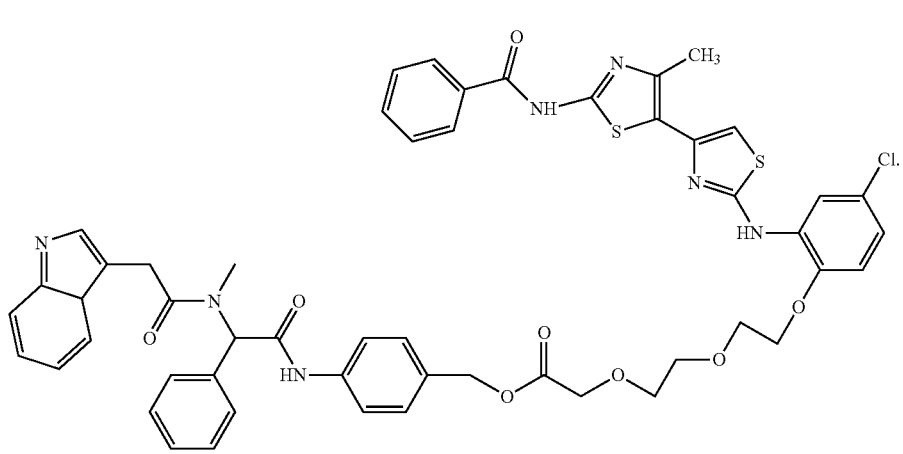

(YM1.4)

Compound YM1.4 is of particular interest as a prodrug, as it incorporates a biodegradable ester linkage. While minimally active in the conjugated form, the individual components equivalent to the hydrolyzed forms exhibit their respective potentiator and corrector activity (See Examples).

Analog and Derivative Compounds

Also provided by the invention are analogs and derivatives of the subject compounds described above. The terms "analog" and "derivative" refers to a molecule which is structurally similar or has the same function or activity as the subject bithiazole, bioxazole or thiazole-oxazole containing compounds of the invention. Such analogs and derivatives of the subject compounds can be screened for efficiency in binding to and modulating the activity of a mutant CFTR, such as ΔF508-CFTR.

In some embodiments, in silico modeling can be used to screen libraries of analog or derivative compounds. For example, protein-ligand docking can be used to predict the position and orientation of a ligand (a small molecule) when it is bound to a protein such as a mutant-CFTR. Docking techniques can be for a variety of purposes, most notably in the virtual screening of large databases of available chemicals in order to select likely drug candidates. An exemplary in silico modeling program suitable for use with the subject method is the PREDICT™ 3D Modeling Technology (Predix Pharmaceuticals, Woburn Mass.), described in greater detail in Becker et al., PNAS 101(3 1): 11304-1 1309 (2004).

Pharmaceutical Preparations

Also provided by the invention are pharmaceutical preparations of the subject compounds described above.

For example, a pharmaceutical preparation of specific interest is a pharmaceutical composition comprising an effective amount of a mutant-CFTR corrector compound having the formula:

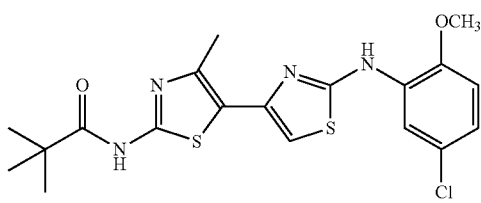 [SMILES: COc1ccc(Cl)cc1Nc1nc(-c2sc(NC(=O)C(C)(C)C)nc2C)cs1]

or a pharmaceutically acceptable derivative thereof, or pharmaceutically acceptable salts, solvates, hydrates, and prodrug forms thereof, and stereoisomers thereof.

Another pharmaceutical preparation of specific interest is a pharmaceutical composition comprising an effective amount of a mutant-CFTR corrector compound having the formula:

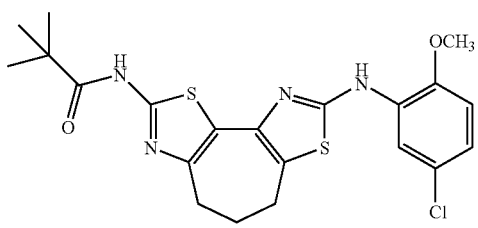 [SMILES: COc1ccc(Cl)cc1Nc1nc2c(s1)CCCc1nc(NC(=O)C(C)(C)C)sc1-2]

or pharmaceutically acceptable derivatives thereof, or pharmaceutically acceptable salts, solvates, hydrates, and prodrug forms thereof, and stereoisomers thereof.

Another pharmaceutical preparation of specific interest is a pharmaceutical composition comprising an effective amount of a mutant-CFTR corrector-potentiator compound having the formula:

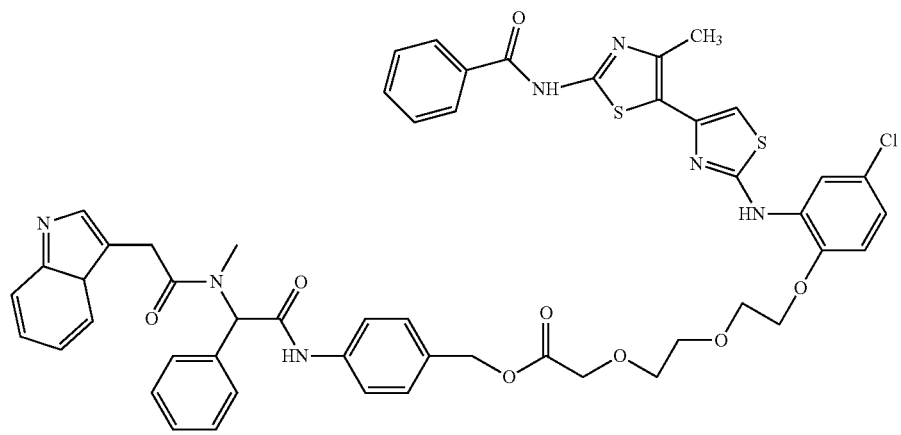 [SMILES: Cc1nc(NC(=O)c2ccccc2)sc1-c1csc(Nc2cc(Cl)ccc2OCCOCCOCC(=O)OCc2ccc(NC(=O)C(c3ccccc3)N(C)C(=O)CC3=CN=C4C=CC=CC34)cc2)n1]

or pharmaceutically acceptable derivatives thereof, or pharmaceutically acceptable salts, solvates, hydrates, and prodrug forms thereof, and stereoisomers thereof.

Pharmaceutically acceptable derivatives include those that retain the essential characteristic of the parent compound, namely, the ability to activate a mutant-CFTR, such as ΔF508-CFTR. The pharmaceutically acceptable derivatives may further include one or more of additional features that impart a pharmacological or biological property that benefits the compound's manufacture, handling, potency, selectivity, and/or pharmacokinetic parameters.

The subject compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols. In most embodiments, the formulations are free of detectable DMSO (dimethyl sulfoxide), which is not a pharmaceutically acceptable carrier, diluent, excipient, or adjuvant, particularly in the context of routes of administration other than transdermal routes. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc., administration.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms

In pharmaceutical dosage forms, the subject compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration.

Routes of administration may be combined, if desired, or adjusted depending upon the agent and/or the desired effect. The composition can be administered in a single dose or in multiple doses.

In one embodiment of particular interest, the compounds of the invention are administered in aerosol formulation via intrapulmonary inhalation. The compounds of the present invention can be formulated into pressurized acceptable propellants such as dichlorodifluoromethane, propane, nitrogen and the like.

Mechanical devices designed for intrapulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo.; the Acorn I1 nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkennes, Cambridge, Mass.; and the AERx pulmonary drug delivery system manufactured by Aradigm Corporation, Hayward, Calif. Of particular interest are the PARI LC PLUS®, the PARI LC STAR®, and the PARI BABY™ nebulizers by PARI Respiratory Equipment, Inc., Monterey, Calif.

Formulations for use with a metered dose inhaler device may generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations may then lyophilized and milled to the desired particle size.

The properly sized particles may then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants may include sorbitan trioleate and soya lecithin. Oleic acid may also be useful as a surfactant. This mixture may then loaded into the delivery device. An example of a commercially available metered dose inhaler suitable for use in the present invention is the Ventolin metered dose inhaler, manufactured by Glaxo Inc., Research Triangle Park, N.C.

Formulations for powder inhalers may comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder may have aerodynamic properties in the lung corresponding to particles with a density of about 1 glcm.sup.2 having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass. The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049 and U.S. Pat. No. 5,654,007.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages

Depending on the subject and condition being treated and on the administration route, the subject compounds may be administered in dosages of, for example, 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition of the to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy

For use in the subject methods, the subject compounds may be formulated with or otherwise administered in combination with other pharmaceutically active agents, including other CFTR-activating agents. The subject compounds may be used to provide an increase in the effectiveness of another chemical, such as a pharmaceutical (e.g., other CFTR-activating agents, or agents potentiate gating defective mutant-CFTR), or a decrease in the amount of another chemical, such as a pharmaceutical (e.g., other CFTR-activating agents), that is necessary to produce the desired biological effect.

Examples of other CFTR activating agents include, but are not limited to, enhancers of intracellular cAMP levels, such as for example, but not limited to, forskolin, rolipram, 8-bromo-cAMP, theophylline, papaverine, cAMP and salts, analogs, or derivatives thereof. Other examples include beta agonists, tobramycin (TOBI®, Chiron Inc., Emeryville, Calif.) and curcumin (Egan et al., (2004) *Science* 304:600-603). The compounds of the invention may also be used in combination with specific mutant CFTR activators, such as correctors and/or potentiators. Examples of mutant-CFTR potentiating agents include, but are not limited to, phenylglycine containing compounds and sulfonamide containing compounds described in WO 2005/120497 and co-pending US provisional patent application serial no. 60/980,387, filed Oct. 16, 2007, entitled "Compounds Having Activity In Increasing Ion Transport By Mutant-CFTR And Uses Thereof", each of which are incorporated herein by reference in its entirety.

The compounds described above may also be combined with other therapies for CF, including oral corticosteroids, ibuprofen, ribovarin or antibiotics such as dicloxacillin, cephalosporin, cephalexin, erythromycin, amoxicillin-clavulanate, ampicillin, tetracycline, trimethoprim-sulfamethoxazole, chloramphenicol ciprofloxacin, tobramycin, gentamicin, cephalosporins, monobactams and the like.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Methods

Methods for Increasing Chloride Ion Permeability of a Mutant-CFTR Cell

The invention provides methods for increasing ion permeability of a cell that produces mutant-CFTR protein, with cells having a folding or processing defective mutant-CFTR being of interest, with cells having a ΔF508-CFTR being of particular interest. In general, the method involves contacting the cell with a compound in an amount effective to correct the folding or processing defect of a mutant-CFTR protein and increase ion permeability of the cell. In some embodiments, the cell contains a recombinant expression cassette that encodes said mutant-CFTR protein. In other embodiments, the cell contains a genome that encodes said mutant-CFTR protein. In yet other embodiments, the mutant-CFTR is a ΔF508-CFTR. In another embodiment of interest, a compound of the invention is used in the method in combination with a second mutant-CFTR activator or potentiator. In another embodiment, the compound of the invention is a hybrid corrector-potentiator compound capable of activating a mutant-CFTR, and the method involves contacting the cell with a compound in an amount effective to potentiate a gating defect or correct the folding or processing defect of a mutant-CFTR protein and increase ion permeability of the cell.

The methods of the invention include treating a subject having a condition associated with mutant-CFTR, which involves administering to the subject a therapeutically effective amount of a pharmaceutical composition of the invention. The invention also includes a method of increasing ion permeability of a cell producing a mutant-CFTR protein, which involves contacting the cell with an effective amount of the pharmaceutical composition of the invention so as to increase CFTR-mediated ion permeability of the cell. In some embodiments, the condition is cystic fibrosis. In some embodiments, the subject, after treatment, has a decrease in mucous or bacterial titer in their lungs, a decrease in coughing or wheezing, a decrease in pancreatic insufficiency, or a decrease in electrolyte levels in their sweat. In some embodiments, the subject is a non-human animal. In embodiments of particular interest, the animal is a mammal. In some embodiments, the mutant-CFTR is a ΔF508-CFTR.

In many embodiments, the mutant-CFTR protein is present on the plasma membrane of the cell. Methods of detecting mutant-CFTR protein presence on the plasma membrane are well known in the art and can include but are not limited to, for example, labeling a molecule that binds to CFTR protein with a fluorescent, chemical or biological tag. Examples of molecules that bind to CFTR protein include, without limitation, antibodies (monoclonal and polyclonal), FAB fragments, humanized antibodies and chimeric antibodies. For an example of an antibody that binds to CFTR protein, see, e.g. U.S. Pat. No. 6,201,107.

In many embodiments, the cell has increased permeability to chloride ions, and the contacting of the cell with a compound of the invention, particularly when provided in combination with another mutant-CFTR activator or potentiator, increases the rate of chloride ion transport across the plasma membrane of the cell. Contacting the cell with a compound of the invention usually increases the activity of mutant-CFTR protein to increase ion transport.

In most embodiments, the ion transport activity of mutant-CFTR, or the permeability of a cell to ions, is increased by up to about 10%, by up to about 20%, by up to about 50%, by up to about 100%, by up to about 150%, by up to about 200%, by up to about 300%, by up to about 400%, by up to about 500%, by up to about 800%, or up to about 1000% or more. In certain embodiments, where there is no detectable ion transport activity of mutant-CFTR or permeability of a cell to ions, contacting of the cell with a compound of the invention causes detectable activity of mutant-CFTR or permeability of a cell to ions.

Activation of mutant-CFTR and or ion permeability may be measured using any convenient methods that may use molecular markers, e.g., a halide sensitive GFP or another molecular marker (e.g., Galietta et al., (2001) *FEBS Lett.* 499, 220-224), patch clamp assays, and short circuit assays.

Suitable cells include those cells that have an endogenous or introduced mutant-CFTR gene. Suitable cells include mammalian cell systems (e.g., COS, CHO, BHK, 293, 3T3 cells etc.) harboring constructs that have an expression cassette for expression of mutant-CFTR. The cell used in the subject methods may be a cell present in vivo, ex vivo, or in vitro. As used herein, the term "expression cassette" is meant to denote a genetic sequence, e.g. DNA or RNA, that codes for mutant-CFTR protein, e.g., ΔF508-CFTR. Methods of introducing an expression cassette into a cell are well known in the art. See for example, Sambrook et al., *Molecular Cloning: A Laboratory Manual*. Cold Spring Harbor Laboratory Press, NY, Vols. 1-3 (1989).

Methods of Treating Cystic Fibrosis

The invention also provides methods of treating a subject having a condition associated with mutant-CFTR, e.g., cystic fibrosis. In general, the method involves administering to the subject a compound of the invention in an amount effective to activate a mutant-CFTR protein to increase ion transport and thereby treat the condition. In an embodiment of particular interest, a compound of the invention is administered in combination with a second mutant-CFTR activator or potentiator, e.g., a compound that enhances intracellular cAMP, e.g., forskolin or a potentiator compound, such as the phenylglycine and sulfonamide containing potentiator compound described in WO 2005/120497 and co-pending US provisional patent application serial no. 60/980,387, filed Oct. 16, 2007, entitled "Compounds Having Activity In Increasing Ion Transport By Mutant-CFTR And Uses Thereof", each of which are incorporated herein by reference in its entirety.

The compounds disclosed herein are useful in the treatment of a mutant-CFTR mediated condition, e.g., any condition, disorder or disease, or symptom of such condition, disorder, or disease, that results from the presence and/or activity of mutant-CFTR as compared to wild-type CFTR, e.g., activity of mutant-CFTR in ion transport. Such conditions, disorders, diseases, or symptoms thereof are amenable to treatment by correction of cellular processing or folding of a mutant-CFTR, e.g., activation of mutant-CFTR chloride transport. Cystic fibrosis, a hereditary condition associated with a mutant-CFTR, e.g., ΔF508-CFTR, is an example of a condition that is treatable using the compounds of the invention. Use of the compounds of the invention in combination with a second mutant CFTR activator or potentiator is of particular interest, including a hybrid corrector-potentiator compound of the invention.

Cystic fibrosis is predominantly a disorder of infants, children and young adults, in which there is widespread dysfunction of the exocrine glands, characterized by signs of chronic pulmonary disease (due to excess mucus production in the respiratory tract), pancreatic deficiency, abnormally high levels of electrolytes in the sweat and occasionally by biliary cirrhosis. Also associated with the disorder is an ineffective immunologic defense against bacteria in the lungs.

Pathologically, the pancreas shows obstruction of the pancreatic ducts by amorphous eosinophilic concretions, with consequent deficiency of pancreatic enzymes, resulting in steatorrhoea and azotorrhoea and intestinal malabsorption. The degree of involvement of organs and glandular systems may vary greatly, with consequent variations in the clinical picture.

Nearly all exocrine glands are affected in cystic fibroses in varying distribution and degree of severity. Involved glands are of three types: those that become obstructed by viscid or solid eosinophilic material in the lumen (pancreas, intestinal glands, intrahepatic bile ducts, gallbladder, submaxillary glands); those that are histologically abnormal and produce an excess of secretions (tracheobronchial and Brunner's glands); and those that are histologically normal but secrete excessive sodium and chloride (sweat, parotid, and small salivary glands). Duodenal secretions are viscid and contain an abnormal mucopolysaccharide. Infertility occurs in 98% of adult men secondary to maldevelopment of the vas deferens or to other forms of obstructive azoospermia. In women, fertility is decreased secondary to viscid cervical secretions, but many women with CF have carried pregnancies to term. However, the incidence of maternal complications increases.

Fifty percent of cystic fibrosis patients with pulmonary manifestations usually chronic cough and wheezing associated with recurrent or chronic pulmonary infections. Cough is the most troublesome complaint, often accompanied by sputum, gagging, vomiting, and disturbed sleep. Intercostal retractions, use of accessory muscles of respiration, a barrelchest deformity, digital clubbing, and cyanosis occur with disease progression. Upper respiratory tract involvement includes nasal polyposis and chronic or recurrent sinusitis. Adolescents may have retarded growth, delayed onset of puberty, and a declining tolerance for exercise. Pulmonary complications in adolescents and adults include pneumothorax, hemoptysis, and right heart failure secondary to pulmonary hypertension.

Pancreatic insufficiency is clinically apparent in 85 to 90% of CF patients, usually presents early in life, and may be progressive. Manifestations include the frequent passage of bulky, foul-smelling, oily stools; abdominal protuberance; and poor growth pattern with decreased subcutaneous tissue and muscle mass despite a normal or voracious appetite. Rectal prolapse occurs in 20% of untreated infants and toddlers. Clinical manifestations may be related to deficiency of fat-soluble vitamins.

Excessive sweating in hot weather or with fever may lead to episodes of hypotonic dehydration and circulatory failure. In arid climates, infants may present with chronic metabolic alkalosis. Salt crystal formation and a salty taste on the skin are highly suggestive of CF.

Insulin-dependent diabetes develops in 10% of adult patients having CF, and multilobular biliary cirrhosis with varices and portal hypertension develops in 4 to 5% of adolescents and adults. Chronic and/or recurrent abdominal pain may be related to intussusception, peptic ulcer disease, periappendiceal abscess, pancreatitis, gastroesophageal reflux, esophagitis, gallbladder disease, or episodes of partial intestinal obstruction secondary to abnormally viscid fecal contents. Inflammatory complications may include vasculitis and arthritis.

Any of above symptoms of CF may be treated using the compounds of the invention, with use of such compounds in combination with a second mutant-CFTR activator or potentiator being of particular interest.

The above methods may be used to treat CF and its symptoms in humans or in animals. Several animal models for CF are known in the art. For example, Engelhardt et al. (*J. Clin. Invest.* 90: 2598-2607, 1992) developed an animal model of the human airway, using bronchial xenografts engrafted on rat tracheas and implanted into nude mice. More recently transgenic models of cystic fibrosis have been produced (e.g., Clarke et al., Science 257: 1125-1128, 1992; Dorin et al., Nature 359: 21 1-215, 1992). With the recent advances of nuclear transfer and stem cell transformation technologies, the alteration of a wild type CFTR gene in an animal to make it into a mutant-CFTR gene is possible for a wide variety of animals.

Many of these animals show human CF symptoms. In particular, many of these animals showed measurable defects in ion permeability of airway and intestinal epithelia, similar to those demonstrable in human CF tissues, and a susceptibility to bacterial infection. Furthermore, most of the deficient mice had intestinal pathology similar to that of meconium ileus. Also, there appeared to be no prenatal loss from litters produced from crosses between heterozygotes.

Animals suitable for treatment using the subject methods include any animal with a mutant-CFTR related condition, particularly a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest. Transgenic mammals may also be used, e.g. mammals that have a chimeric gene sequence. Methods of making transgenic animals are well known in the art, see, for example, U.S. Pat. No. 5,614,396. For an example of a transgenic mouse with a CFTR defect, see e.g. WO 94104669.

Such animals may be tested in order to assay the activity and efficacy of the subject compounds. Improvement in lung function can be assessed by, for example, monitoring prior to and during therapy the subjects forced vital capacity (FVC), carbon monoxide diffusing capacity (DLco), and/or room air $pO_2>55$ mmHg at rest. Significant improvements in one or more of these parameters are indicative of efficacy. It is well within the skill of the ordinary healthcare worker (e.g., clinician) provide adjust dosage regimen and dose amounts to provide for optimal benefit to the patient according to a variety of factors (e.g., patient dependent factors such as the severity of the disease and the like), the compound administered, and the like).

Subjects Suitable for Treatment

Subjects suitable for treatment with a method of the present invention include individuals having mutant-CFTR protein-mediated condition disorder or disease, or symptom of such condition, disorder, or disease that results from or is correlated to the presence of a mutant-CFTR, usually two alleles of the mutant CFTR. Moreover, subjects suitable for treatment with a method of the present invention include individuals with CF. Of particular interest in many embodiments is the treatment of humans with CF.

Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma.

The compounds of the present invention affect the ion transport capability of the mutant-CFTR by increasing the reduced level of ion transport mediated by a mutant-CFTR, such as the ΔF508-CFTR. As such, the corrector and hybrid corrector-potentiator compounds of the present invention have particular clinical utility in treating a subset of CF patients that have mutations in the CFTR gene that results a mutant-CFTR that is expressed in the plasma membrane and has reduced chloride conductance capability due to folding or cellular processing (i.e., the mutant-CFTR is folding or cellular processing defective). As such, the corrector compounds of the present invention have clinical utility in treating CF patients having a folding or cellular processing mutant-CFTR, such as ΔF508-CFTR. In addition, the hybrid CFTR-mutant corrector-potentiator compounds of the invention have clinical utility in the treating CF patients having a gating defective mutant CFTR, such as ΔF508-CFTR, G551D-CFTR, G1349D-CFTR, or D1152H-CFTR, or a folding or cellular processing mutant-CFTR. In addition, the corrector compounds of the present invention also have clinical utility in treating CF patients when used in conjunction with compounds that activate or potentiate a gating mutant-CFTR, such as ΔF508-CFTR, G551D-CFTR, G1349D-CFTR, or D1152H-CFTR.

CFTR mutations associated with CF are well known in the art. These mutations can be classified in five general categories with respect to the CFTR protein. These classes of CFTR dysfunction include limitations in CFTR production (e.g., transcription and/or translation) (Class I), aberrant folding and/or trafficking (Class II), abnormal regulation of conduction (Class III), decreases in chloride conduction (Class IV), and reductions in synthesis (Class V). Due to the lack of functional CFTR, Class I, II, and III mutations are typically associated with a more severe phenotype in CF (i.e. pancreatic insufficiency) than the Class IV or V mutations, which may have very low levels of functional CFTR expression. A listing of the different mutations that have been identified in the CFTR gene is as found at the world-wide website of the Cystic Fibrosis Mutation Database at genet.sickkids.on.ca/cgi-bin/WebObjects/MUTATION, specifically incorporated by reference herein in its entirety.

A subject suitable for treatment with a method of the present invention may be homozygous for a specific mutant-CFTR, i.e. homozygous subjects with two copies of a specific mutant-CFTR, e.g., ΔF508-CFTR. In addition, subjects suitable for treatment with a method of the present invention may also be compound heterozygous for two different CFTR mutants, i.e., wherein the genome of the subjects includes two different mutant forms of CFTR, e.g., a subject with one copy of ΔF508-CFTR and a copy of different mutant form of CFTR.

In some embodiments of the invention, the mutant-CFTR polypeptide is ΔF508-CFTR. In other embodiments of the invention, the mutant-CFTR polypeptide is G551D-CFTR. In yet other embodiments of the invention, the mutant-CFTR polypeptide is G1349D-CFTR. In still other embodiments of the invention, the mutant-CFTR polypeptide is D152H-CFTR. The invention, however, should not be construed to be limited solely to the treatment of CF patients having this mutant form of CFTR. Rather, the invention should be construed to include the treatment of CF patients having other mutant forms of CFTR with similar characteristics, that result in expression of the mutant-CFTR in the plasma membrane and has reduced chloride conductance capability or has abnormal regulation of conductance.

Kits & Systems

Also provided are kits and systems that find use in practicing the subject methods, as described above. The kits typically contain unit doses of the subject compounds, usually in oral or injectable doses. For example, kits and systems for practicing the subject methods may include one or more pharmaceutical formulations that include corrector compound of the invention, and optionally one or more additional components. As such, in certain embodiments the kits may include a single pharmaceutical composition present as one or more unit dosages. In yet other embodiments, the kits may include two or more separate pharmaceutical compositions, as well as be part of a system. The term "system" as employed herein refers to a collection of components or agents present in single or disparate compositions that are brought together for the purpose of practicing the subject methods. This includes systems libraries of the compounds of the invention as well as individual compounds of the invention.

Thus the kits can include one or more of, depending upon the intended use of the kit, the compositions described herein, such as: a corrector compound of the invention, a hybrid-corrector-potentiator compound of the invention, and the like. Other optional components of the kit include: buffers, delivery vehicles, delivery systems etc., for administering a corrector compound, and/or for performing a diagnostic assay. The various components of the kit may be present in separate containers or certain compatible components may be pre-combined into a single container, as desired. The kits also may include one or more additional pharmaceuticals or agents for treating a mutant-CFTR.

In addition to the above components, the subject kits may further include instructions for practicing the subject methods, such as an informational package insert describing the use and attendant benefits of the drugs in treating pathological condition of interest. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In a specific embodiment, a kit is provided for use in treating a subject suffering from cystic fibrosis. This kit includes a pharmaceutical composition comprising corrector compound of the invention, and/or a hybrid corrector-potentiator compound of the invention, and instructions for the effective use of the pharmaceutical composition in a method of treating a subject suffering from cystic fibrosis. Such instructions may include not only the appropriate handling properties, dosing regiment and method of administration, and the like, but further include instructions to optionally screen and type the subject for mutant-CFTR (e.g., ΔF508-CFTR, G551D-CFTR, G1349D-CFTR, or D1152H-CFTR). This aspect of the invention assists the practitioner of the kit in tracking or gauging the potential responsiveness of the subject to treatment with a composition of the invention. Thus in another embodiment, the kit may further include a system for characterizing mutant-CFTRs, such as described in WO 2005/120497. In another embodiment, the kit includes one or more corrector compositions that are detectably labeled.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Centigrade, and pressure is at or near atmospheric. Thus it is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes Example 1

General Materials and Methods

Biological Assays The compounds are tested for biological activity by various methods. Dose-response assays measuring I$^-$ influx are performed on ΔF508-CFTR transfected Fischer rat thyroid (FRT) epithelial cells. Other cell lines are the "class III" gating defective CFTR mutants G551D-CFTR and G1349D-CFTR, which are potentiator specific variants (Gregory et al., MCB 11: 3886-3893 (1991). These mutations affect the glycine residues in NBDI and NBD2 that are highly conserved in ATP-binding cassette proteins (Hyde et al., 1990; Logan et al., 1994). The gating defective mutant G551D-CFTR represents the most common gating defect causing cystic fibrosis. Other assays include patch-clamp analysis to assess electrophysiological mechanism of ΔF508-CFTR activation, and transepithelial current measurements to confirm activation of ΔF508-CFTR CF currents. Primary cultures are used to assess activity of the compounds in a native lung airway system, such as nasal epithelial cells from a ΔF508 homozygous subject, and nasal polyp epithelial cells from a CF patient with the G551D-CFTR mutation. Direct interaction between the test compounds with ΔF508-CFTR is performed by measuring cellular cAMP concentrations to confirm that synergy of the test compounds with forskolin is not due to cAMP elevation.

Cell lines Clonal populations of Fischer rat thyroid (FRT) epithelial cells stably co-expressing human ΔF508-CFTR and the high-sensitivity halide-sensing green fluorescent analog YFP-H148QI152L (Galietta et al., A. S. (2001) FEBS Lett. 499, 220-224) are generated by liposome transfection and limiting dilution with ZeocidG418 selection. Clones are evaluated for high fluorescence and ΔF508-CFTR plasma membrane targeting after growth at 27° C. for 24 hours. For screening, cells are cultured on plastic in Coon's modified F12 medium supplemented with 10% fetal bovine serum, 2 mM L-glutamine, 100 U/ml penicillin, and 100 pglml streptomycin, and plated on black 96-well microplates (Corning-Costar 3904) at 30,000 cells/well. For short-circuit measurements cells are cultured on Snapwell permeable supports (Corning-Costar) at 500,000 cells/insert. Human nasal epithelium cells from CF patients are cultured on Snapwell inserts and allowed to differentiate in a hormone-supplemented medium (Galietta et al., Am. J. Physiol., 275: 19723-19728 (1998)). Other measurements are done using stably transfected FRT cells expressing YFP-H148Q and wildtype- or G5511D-CFTR (Galietta et al., (2001) J. Biol. Chem. 276, 19723-19728). Patch clamp experiments are done on ΔF508-CFTR-expressing FRT cells plated in 35-mm Petri dishes.

Iodine Influx Rate Compounds are tested for CFTR corrector or potentiator activity using a Beckman integrated system containing a 3-meter robotic arm, $CO_2$ incubator containing microplate carousel, plate-washer, liquid handling workstation, bar code reader, delidding station, plate sealer, and two FluoStar fluorescence plate readers (Galaxy, BMG Lab Technologies), each equipped with dual syringe pumps and HQ500/20X (500±10 nm) excitation and HQ535130M (535±15 nm) emission filters (Chroma). Software written in VBA (Visual Basic for Applications) is used to compute baseline-subtracted fluorescence slopes (giving halide influx rates).

For assay of ΔF508-CFTR corrector or potentiator activity, the incubator (27° C., 90% humidity, 5% $CO_2$/95% air) is loaded with forty-to-sixty 96-well plates containing FRT cells. After an 18-24 hour incubation plates are washed 3 times with PBS (300 μl/wash) leaving 50 μl PBS. 10 μl of PBS containing 120 μM forskolin is added, and after 5 min test compounds (0.6 μl of 0.25 nM DMSO solution) are added to each well to give 2.5 μM final compound concentrations. After 15 min, 96-well plates are transferred to a plate reader for fluorescence assay. Each well is assayed individually for iodine ion (I⁻) influx by recording fluorescence continuously (200 ms per point) for 2 seconds (baseline) and then for 12 seconds after rapid (4 s) addition of 160 μL of isosmolar PBS in which 137 mM Cl⁻ is replaced by I⁻. I⁻ influx rates are computed from initial fluorescence versus time-curve slopes (determined by 3rd order polynomial regression) after normalization for total fluorescence (background subtracted initial fluorescence). All compound plates contain negative control (e.g., DMSO vehicle alone) and positive controls (e.g., genistein, 5 μM and 50 μM). Assay analysis typically indicate a Z'-factor of >0.7 (Zhang et al., J. Biomol. Screen 4:67-73 (1999)).

For example, FRT epithelial cells stably coexpressing human ΔF508-CFTR and the high-sensitivity halide-sensing green fluorescent protein YFP-H148Q/I152L (Galietta et al., FEBS Lett. (2001) 499:220-224) were carried out as described previously (Pedemonte et al., J. Clinical Investigation (2005) 115:2564-2571). Cells were grown at 37° C. (90% humidity; 5% CO2) for 24 hours and then incubated for 20 hours with 50 μl of medium containing test compounds. At the time of the assay, cells were washed with PBS and then incubated with PBS containing forskolin (20 μM) and genistein (50 μM) for 20 min. Measurement was carried out using FLUOstar fluorescence plate readers (Optima; BMG LABTECH Gmbh), each equipped with 500±10 nm excitation and 535±15 nm emission filters (Chroma Technology Corp.). Each well was assayed individually for I⁻ influx by recording fluorescence continuously (200 ms per point) for 2 seconds (baseline) and then for 12 seconds after rapid (<1 second) addition of 165 μl PBS in which 137 mM Cl⁻ was replaced by I⁻. The I⁻ influx rate was computed by fitting the final 11.5 seconds of the data to an exponential for extrapolation of initial slope and normalizing for background-subtracted initial fluorescence. All experiments contained negative controls (DMSO vehicle) and positive controls (CLY-corr-F6).

Whole-cell patch-clamp The cell-attached configuration of the patch-clamp technique is performed on FRT cells expressing ΔF508-CFTR as follows. Cells are seeded at a density of $10^4$ cells/well and grown at 37° C. for 24-48 hours and then incubated for 24-48 hours at 27° C. to allow trafficking of the ΔF508 protein to the plasma membrane. Borosilicate glass pipettes are fire polished to obtain tip resistances of 2-4 MΩ. Currents are sampled at 500 Hz using a patch-clamp amplifier (EPC-7, List, Darmstadt) and low-pass filtered using a 4-pole Bessel filter set at a cutoff frequency of 250 Hz and digitized at 500 Hz using an ITC-16 data translation interface (Instrutech). The extracellular (bath) solution is prepared to contain (in mM): 150 NaCl, 1 $CaCl_2$, 1 $MgCl_2$, 10 glucose, 10 mannitol, and 10 TES (pH 7.4). The pipette solution is prepared to contain (in mM): 120 CsCl, 1 $MgCl_2$, 10 TEA-Cl, 0.5 EGTA, 1 Mg-ATP, and 10 Hepes (pH 7.3). Membrane conductances are monitored by alternating the membrane potential between +80 and −100 mV. Current-voltage relationships are generated by applying voltage pulses between −100 and +100 mV in 20 mV steps. Analysis of open channel probability ($P_o$), mean channel open time ($T_o$), and mean channel closed time ($T_c$) are done using recordings of at least three minute intervals (Taddei et al., FEBS Lett. 55852-56 (2004)).

Transepithelial current measurements Chamber experiments for short-circuit transepithelial measurements are performed 7-9 days after plating ΔF508-CFTR expressing FRT cells on Snapwell inserts. The basolateral solution is prepared to contain (in mM): 130 NaCl, 2.7 KCl, 1.5 $KH_2PO_4$, 1 $CaCl_2$, 0.5 $MgCl_2$, 10 glucose, 10 Na-Hepes (pH 7.3). In the apical bathing solution 65 mM NaCl is replaced by Na gluconate, and $CaCl_2$ increased to 2 mM. Solutions are bubbled with air and maintained at 37° C. The basolateral membrane is permeabilized with 250 μg/ml amphotericin B. The hemichambers are connected to a DVC-1000 voltage clamp (World Precision Instruments) via Ag/AgCl electrodes and 1 M KCl agar bridges for recording short-circuit current.

Assay of cAMP cAMP activity is measured using the BIOTRAK enzymatic immunoassay (Arnersham) of FRT cell lysates after incubation with the compounds for 10 minutes in the presence of 0.5 pM forskolin.

Pharmacokinetics To increase compound solubility when necessary, the compounds are dissolved in a liposomal formulation containing 5 mg potentiator in 2 1.3 mg hydrogenated soy phosphatidylcholine, 5.2 mg cholesterol, 8.4 mg distearoylphosphatidylglycerol, and 90 mg sucrose in 5 ml PBS. A bolus of potentiator containing solution (5 mg/kg) is administered intravenously in rats over 1 min (male Sprague-Dawley rats, 360-420 grams) by a jugular vein catheter. Arterial blood samples (~1 ml) are obtained at predetermined times for LCMS analysis.

Liquid Chromatography/Mass Spectrometry (LCMS) For analysis of blood samples, collected plasma is chilled on ice, and ice-cold acetonitrile (2:1 v:v) added to precipitate proteins. Samples are centrifuged at 4° C. at 20,000 g for 10 min. Supernatants (supplemented with sulforhodamine 101 as internal standard) are analyzed for test compounds by extraction with C-18 reversed-phase cartridges (1 ml, Alltech Associates, Inc. Deerfield, Ill.) by standard procedures. The eluate is evaporated, and the residue reconstituted in 100 μl of mobile phase for HPLC analysis. Reversed-phase HPLC separations are carried out using a Supelco C18 column (2.1× 100 mm, 3 μm particle size) connected to a solvent delivery system (Waters model 2690, Milford, Mass.). The solvent system consists of a linear gradient from 20% $CH_3CN$/10 mM $KH_2PO_4$, pH 3 to 95% $CH_3CN$/10 mM $KH_2PO_4$, pH 3 over 10 min, followed by 6 min at 95% $CH_3CN$/20 mM $NH_4OAc$ (0.2 ml/min flow rate). Test compounds are detected at 256 nm, after establishing a linear standard calibration curve in the range of 20-5000 nM. The typical detection limit is 10 nM and recovery >90%. Mass spectra are acquired on a mass spectrometer (Alliance HT 2790+ZQ) using negative ion detection, scanning from 200 to 800 Da (Sonawane et al., J. Pharm. Sci. 94:134-143 (2004)).

Stability in hepatic microsomes To predict hepatic clearance of test compounds, in vitro incubations are done with rat hepatic microsomes in the absence (control) and presence of NADPH as follows. Test compounds (10 μM each) are incubated separately with a phosphate buffered (100 mM) solution of rat liver microsomes (2 mg proteinlml, Sigma) containing NADPH (0 or 1 mM) for 60 min at 37° C. After 60 min the mixture is chilled on ice, and 0.5 ml of ice-cold acetonitrile added to precipitate the proteins for LCMS analysis as described above.

Example 2

Synthesis of Corrector 4 (Control)

An efficient route for the synthesis bithiazole analogs was developed as follows. Efforts began with a synthesis of N-(2-(5-chloro-2-methoxyphenylamino)-4'-methyl-4,5'-bithiazol-2'-yl)benzamide—the putative structure of "Corr-4" corrector 4. This work commenced by treating 3-chloropentane-2,4-dione with thiourea under reflux in absolute ethanol. 5-Acetyl-2-amino-4-methylthiazole (5) was obtained in 90% yield. Surprisingly, attempts to aminoacylate the 2-amino moiety in 5 with benzoyl chloride under various base, solvent and temperature conditions failed to deliver the desired intermediate N-(5-acetyl-4-methyl-thiazol-2-yl)-benzamide (6).

It was determined that the poor yield of 5→6 was a consequence of the 5-acetyl moiety reducing the nucleophilicity of the 2-amino group of 5. Since the plan was to diversify with a spectrum of acid chlorides, this problematic reaction led to evaluation of the inverse of these two reactions—i.e., use bezoyl isothiocyanate as the starting material in place of thiourea (Scheme 1). Passing ammonia gas through a dichloromethane solution of benzoyl isothiocyanate delivered N-carbamothioylbenzamide (7) which then reacted with 3-chloropentane-2,4-dione to afford 6 in good yield. α-Bromination of the acetyl group of 6 proved to be quite challenging with the recovery of unreacted 6 being the principle issue [Br$_3$ on Amberlite A-26 resin, CHCl$_3$, rt, 24 h/no reaction; Br2 in AcOH, rt, 24 h/>50% recovered 6; NBS, CHCl$_3$, reflux, 24 h/>50% recovered 6]. Pyridinium tribromide in a 30% HBr in acetic acid solution resolved the problem, presumably by the strongly acidic medium promoting enolization. Finally, treating bromoacetyl thiazole 8 (obtained form 6) was subsequently treated with thiourea 9, in turn prepared by treating 5-chloro-2-methoxyaniline with ammonium thiocyanate, in refluxing ethanol to deliver corrector 4 in excellent yield. Importantly, no column chromatography purifications were required throughout the four-step process outlined in Scheme 1, where the reagents and conditions are as follows: (i) NH$_3$, DCM, 0° C. to r.t. (ii) 3-Chloropentane-2,4-dione, EtOH, reflux. (iii) Pyr.H$^+$Br$_3^-$, 30% HBr in HOAc, r.t. (iv) 1-(5-Chloro-2-methoxyphenyl)thiourea, EtOH, reflux.

Scheme 1: Synthesis of Corrector 4

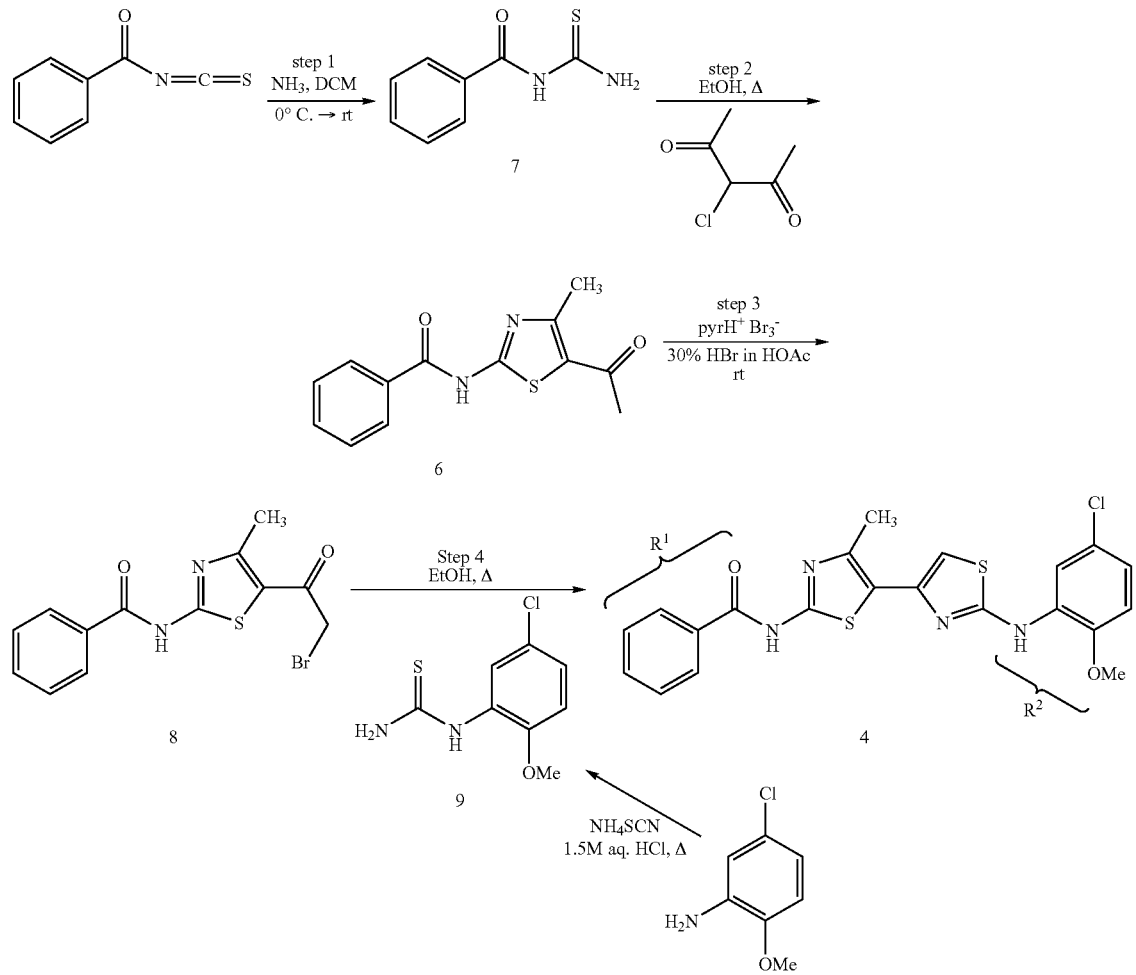

Example 3

Analysis of ΔF508-CFTR Corrector Activity for Corrector 4

Compound 4 from Example 2 was tested for ΔF508-CFTR corrector activity as follows. The dose-response data for corrector 4 is shown in FIG. 1 where the dashed line indicates the level of activity with low-temperature (27° C.) rescue which is used as a positive control. Activation of ΔF508-CFTR was confirmed for each of the compounds by showing no activity on nontransfected FRT cells and near-complete inhibition of the increased influx by the thiazolidinone CFTRinh-172 at 10 μM as previously described (Ma et al., J. Clin. Investig. (2002) 110:1651-1658) (data not shown).

Example 4

Design and Synthesis of Corrector 4 Analogs—Library I

Compounds were designed and prepared to examine the amide $R_1$ (benzamide on corrector 4), the amine $R_2$ (aniline on corrector 4), and the core bithiazole moiety (methylbithiazole on corrector 4), as well as combinations thereof, on activity. To systemize this effort, an initial collection of analogs were synthesized in which the N-(4'-methyl-4,5'-bithiazol-2'-yl)benzamide moiety was held constant while the aniline moiety was varied (Scheme 2). As outlined in Scheme 2, each of these derivatives was available in one step by condensation of the appropriate 1-arylthiourea with N-(5-(2-bromoacetyl)-4-methylthiazol-2-yl)benzamide (8).

Scheme 2: Synthesis and Library I analogs

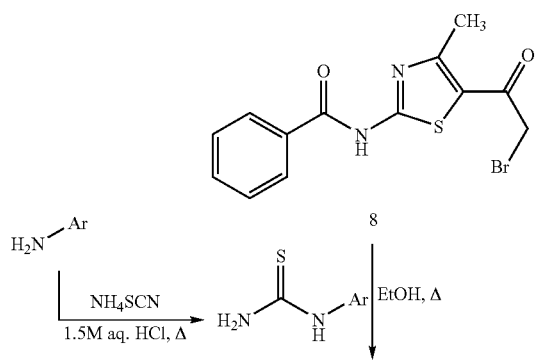

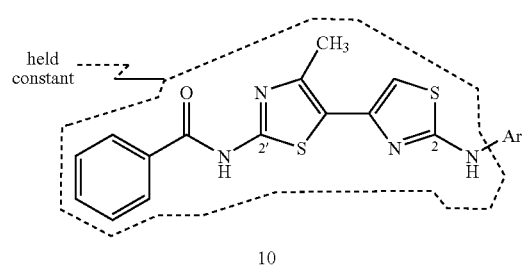

10 a: Ar = p-MeC$_6$H$_4$
b: Ar = p-MeOC$_6$H$_4$
c: Ar = p-FC$_6$H$_4$
d: Ar = m-FC$_6$H$_4$
e: Ar = m-MeOC$_6$H$_4$
f: Ar = p-ClC$_6$H$_4$
g: Ar = m-Cl(o-MeO)C$_6$H$_3$
h: Ar = o-Cl(m-Cl)C$_6$H$_3$

Example 5

Analysis of ΔF508-CFTR Corrector Activity for Library I Analogs

Figure 2:
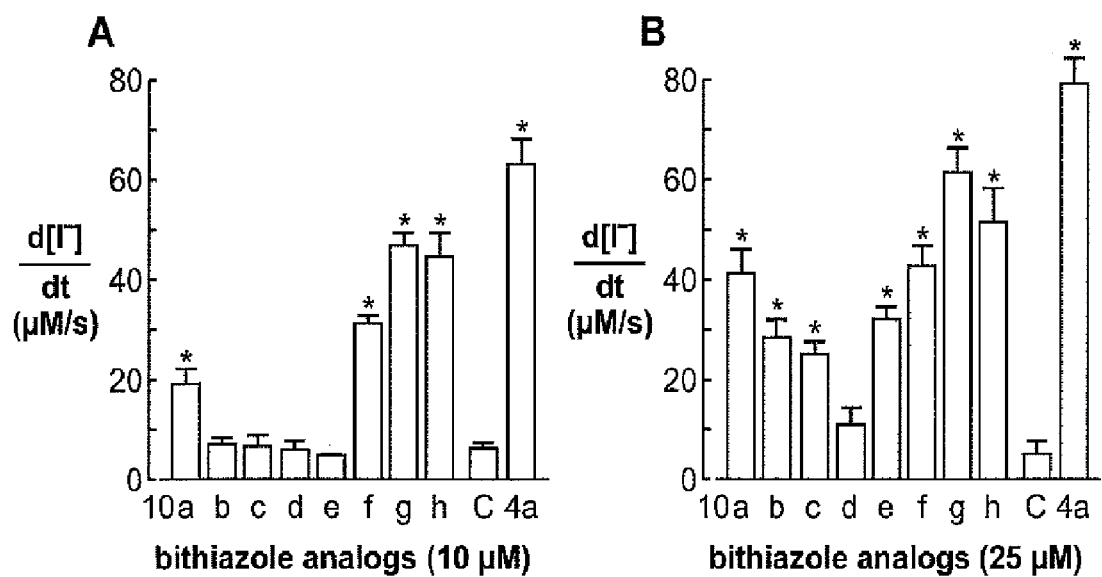
FIG. 2: ΔF508-CFTR sensitivity to forskolin after incubation with select corrector compounds from library set one (Library I) (C=negative control with dimethyl sulfoxide (DMSO)).

The corrector efficacy of methybithiazoles 10a-h are summarized in FIG. 2 which shows the increased sensitivity to forskolin (20 mM) in ΔF508-CFTR-expressing FRT cells kept at 37° C. Although all of these methylbithiazoles were less effective correctors of ΔF508-CFTR than compound 4, three (10f, 10g, and 10h) were moderately effective. Indeed, compounds 10g and 10h showed comparable corrector activity to 4 at both 10 and 25 μM concentrations. Also, this small set of compounds established that placing a fluoro group, which is a significant electron withdrawing group, on the aniline moiety (e.g., 1c and 1d) caused a significant decrease in activity and this decrease was independent of where the fluoride was located. All-in-all, this initial set of compounds established that peripheral modification of the methylbithiazole core modulates corrector activity.

Example 6

Synthesis of Library II Analogs

Further analoging of the amide and aniline moieties of corrector 4, based on data from bithiazoles 10a-h, yielded a second library set (11α-11δj) that was prepared by reagent-based modification of the protocol outlined in Scheme 1 (e.g., the isothiocyanate employed in step 1 incorporate aryl moieties α-β and the N-aryl thioureas used is step 4 incorporated aryl moieties a-j). Based on the results with 10c and 10d, fluorine was precluded from the $R_2$ aryls.

TABLE 1

Library II analogs

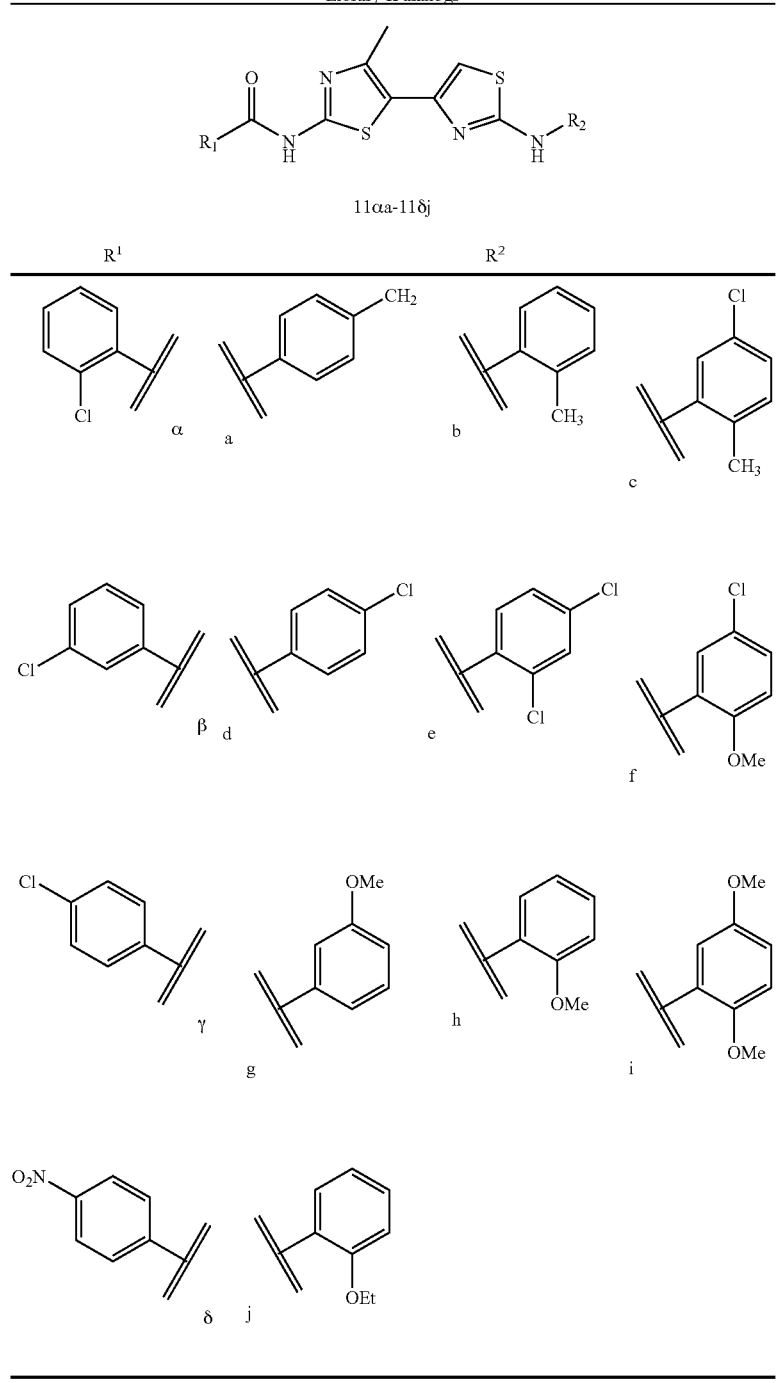

11αa–11δj

Example 7

Synthesis of Library III Analogs

While library set two was under preparation, background work for a third library set was undertaken. For this set, $R_1$ diversity (see 4 in Scheme 1) was expanded to include non-aryl substituents. Thus, although the Scheme 1 chemistry had several attractive features—namely, high yielding reactions and no chromatographic purifications, $R_1$ diversity in these bithiazoles was limited by the isothiocyanate commercial availability. Since previous attempts at benzoylation 5→6 were problematic, library set three was constructed by assembly of the bithiazole first with subsequent N-acylation (see Scheme 3). The 2'-amino group in the 4'-methyl-N2-aryl-4,5'-bithiazole-2,2'-diamine intermediate was found to be considerably more nucleophilic than the corresponding amine in aminothiazole 5 with its C5 acyl moiety. In addition, adding the $R_1$ diversity input in the last step was found to provide considerable time- and labor-saving benefits, particularly with regards to product purification.

Scheme 3: Synthesis of Library III analogs

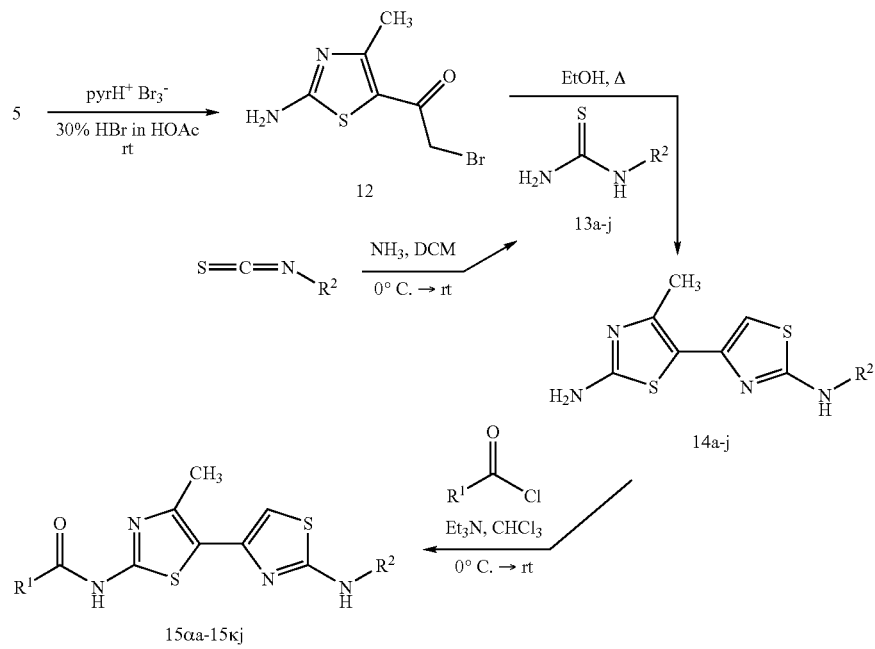

Bromination of 5 using pyridinium tribromide with 30% HBr in acetic acid afforded 12 in 50% yield. While the isolated product yield of this reaction was significantly lower than the nearly quantitative bromination 6→8, the cause of this modest yield was the water solubility of the ammonium salt of 12. Aromatic thioureas 13a-j were prepared by bubbling ammonia gas through the commercially available aromatic isothiocyantates in DCM. After simply evaporating the DCM, clean aromatic thioureas 13a-j were obtained in high yield. Bromothiazole 12 was subsequently refluxed in ethanol with thiourea 13a-j to afford 2'-aminobithiazole 14a-j in ~60-80% yields. These compounds had modest impurities which proved difficult to remove by flash column chromatography. Consequently, for ease of synthesis, the crude 2'-aminobithiazoles were used in the next step without purification.

TABLE 2

Library III analogs

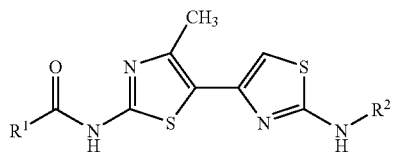

15αa-15xj
R¹ diversity*

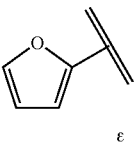
α

β

TABLE 2-continued

Library III analogs

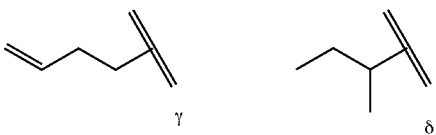

15αa-15xj
R¹ diversity*

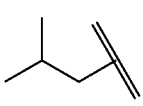
γ

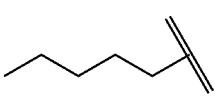
δ

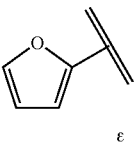

ε

ζ

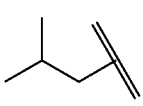
η

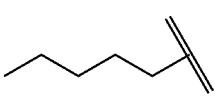
θ

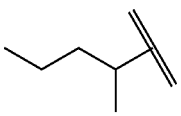
ι

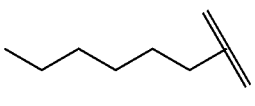
κ

*(see Table 1 for R₂ diversity)

Acylation of 2'-amino moiety of 14a-j with various acid chlorides in the presence of triethylamine in chloroform afforded the 100 library set three bithiazoles 15αa-15κj (Scheme 3). P LCMS analysis of this last reaction generally showed ~40-60% reaction completion. Additional reaction time or the addition of more acid chloride only made product purification more difficult. Upon work-up, the products were purified by prep-HPLC and again analyzed by LC-MS. All showed >90% or better purities and correct molecular ion peaks.

Figure 3:
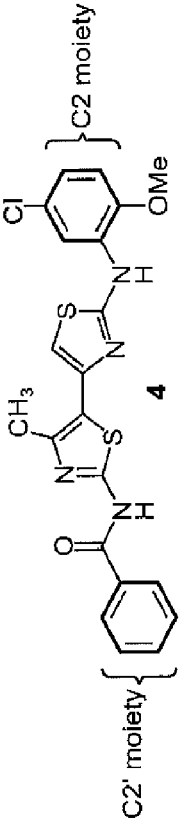
FIG. 3: IC50/Vmax data for select corrector compounds from library set two (Library II) in correcting Δ508-CFTR.
Figure 4:
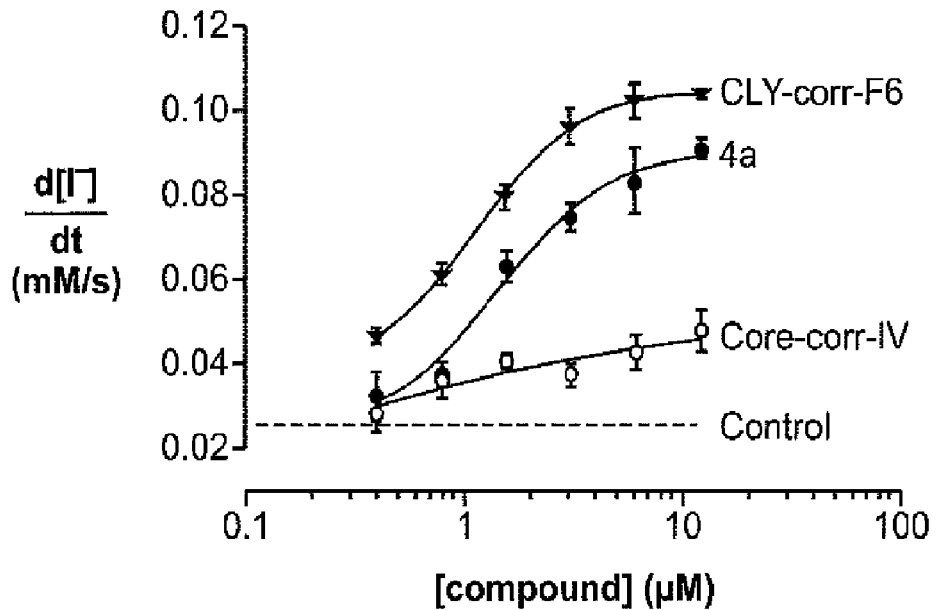
FIG. 4: Dose-response curves comparing select corrector compounds from library set three (Library III) in correcting ΔF508-CFTR.

The IC50/Vmax data for the eight most active methyl-bithiazoles from the 11αa-11δj and 15α-15κj series (40 and 100 compounds, respectively) are delineated in FIG. 3. It was noted that six out of the eight best methylbithiazole share either a 4-chlorobenzamide (11γa, 11γd, 11γi) or a pivalamide (15ζf, 15ζh, 15ζj) at the 2''-position and five out of these eight share either o-methoxy or o-ethoxy aromatic amines (11γi, 15ζf, 15ζh, 15ζj, 15κi) at the 2-position. When there is a para substituted aromatic amide at the 2'-position (11γa, 11γd, 11γi, 11δd), p-substituted aromatic amines at the 2-position have elevated activity (11γa, 11γd, 11δd). It was also found that bithiazole 15κi, which contains a relatively long alkyl amide, expressed comparable activity as a corrector. Among the bithiazoles screened in Libraries I-III, including the corrector 4, bithiazole 15ζf (also designated as "CLY-corr-F6") showed best activity in both Vmax and IC50 (see FIGS. 3 and 5).

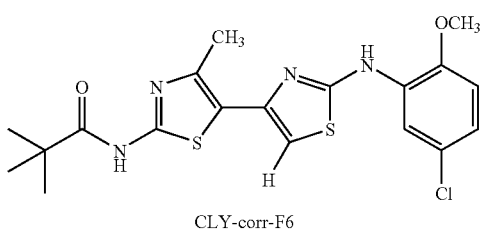 [SMILES: COc1ccc(Cl)cc1Nc1nc(-c2sc(NC(=O)C(C)(C)C)nc2C)cs1]

CLY-corr-F6

Example 8

Synthesis of Photo Affinity-Labeled Corrector Analogs

To understand how the corrector is binding to CFTR, a photoaffinity label can be installed on corrector analogs (an example is illustrated in Scheme 4 for corrector 4). Photoaffinity labeling aids in understanding molecular interactions with CFTR and provides invaluable binding information for designing more active compounds.

Scheme 4: Photoaffinity labeling of corrector analogs

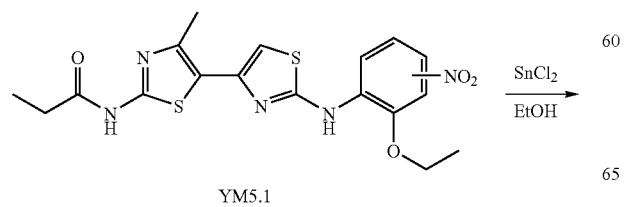

YM5.1

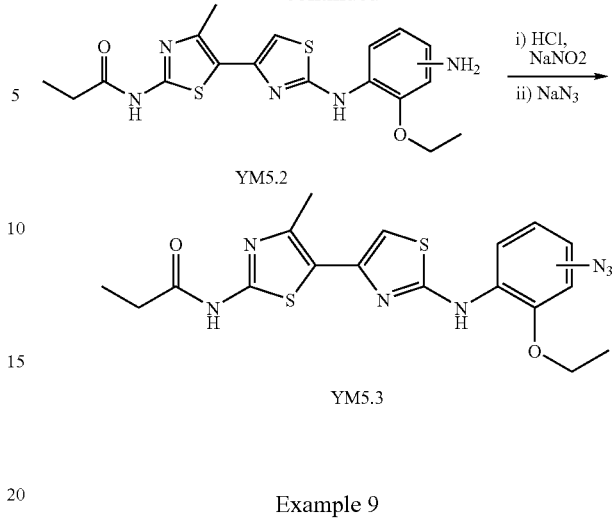

YM5.2

YM5.3

Example 9

Synthesis of Library IV Analogs

Having improved the efficacy of the methybithiazole-based corrector activity by modifying the amide and aniline moieties, attention was focused next on the bithiazole core. The torsional angle of the carbon-carbon bond connecting the thiazoles was examined to determine whether controlling rotation about the central C,C bond of the core would positively influence the activity of CLY-corr-F6 (e.g., the best compound to come from the study described in Example 7).

In work to this point, the core structure was constructed starting from 3-chloro-2,4-butanedione because the symmetry of this starting material allows the first thiazole cyclization to occur at either carbonyl. However, the consequence of this is that methyl and hydrogen substituents are unavoidable on the two thiazole rings, respectively. It was noted, however, that the Me and H placement could be effectively inverted by controlling the thiazole formation order. Accordingly, the relevant derivatives were prepared. An exemplary set of derivatives for this purpose are depicted in Table 3 below, where R in this context is a substituent for variation, and Ar is an unsubstituted or substituted aryl group for variation.

TABLE 3

Library IV analogs

TABLE 3-continued

Library IV analogs

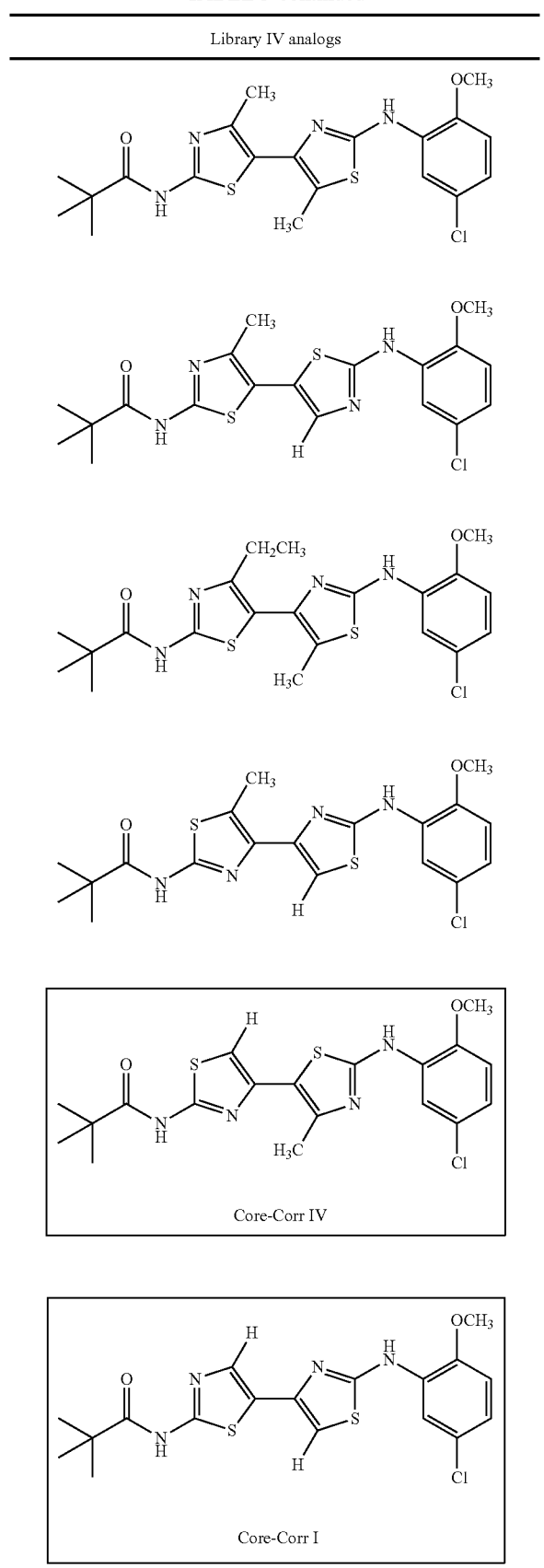

Core-Corr IV

Core-Corr I

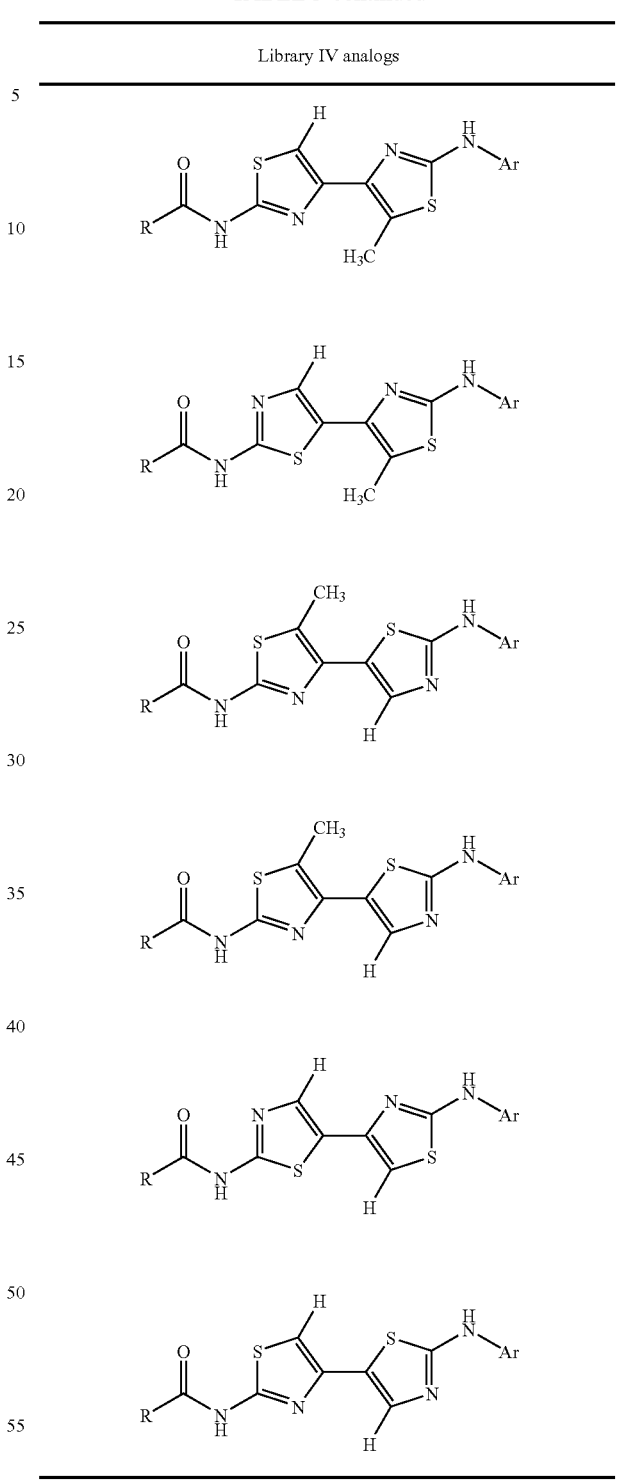

Synthesis of four exemplary bithiazole analogs of Table 3 is shown in the following scheme. Preliminary studies indicated that the H,H-analog (central scheme below) Core-Corr I was as active as corrector 4, while the others exhibit little activity (See FIG. 5). This demonstrated that the relative placement of the Me and H of the corrector 4 and its analogs is critical for optimal activity.

Scheme 5: Synthesis of Library IV analogs
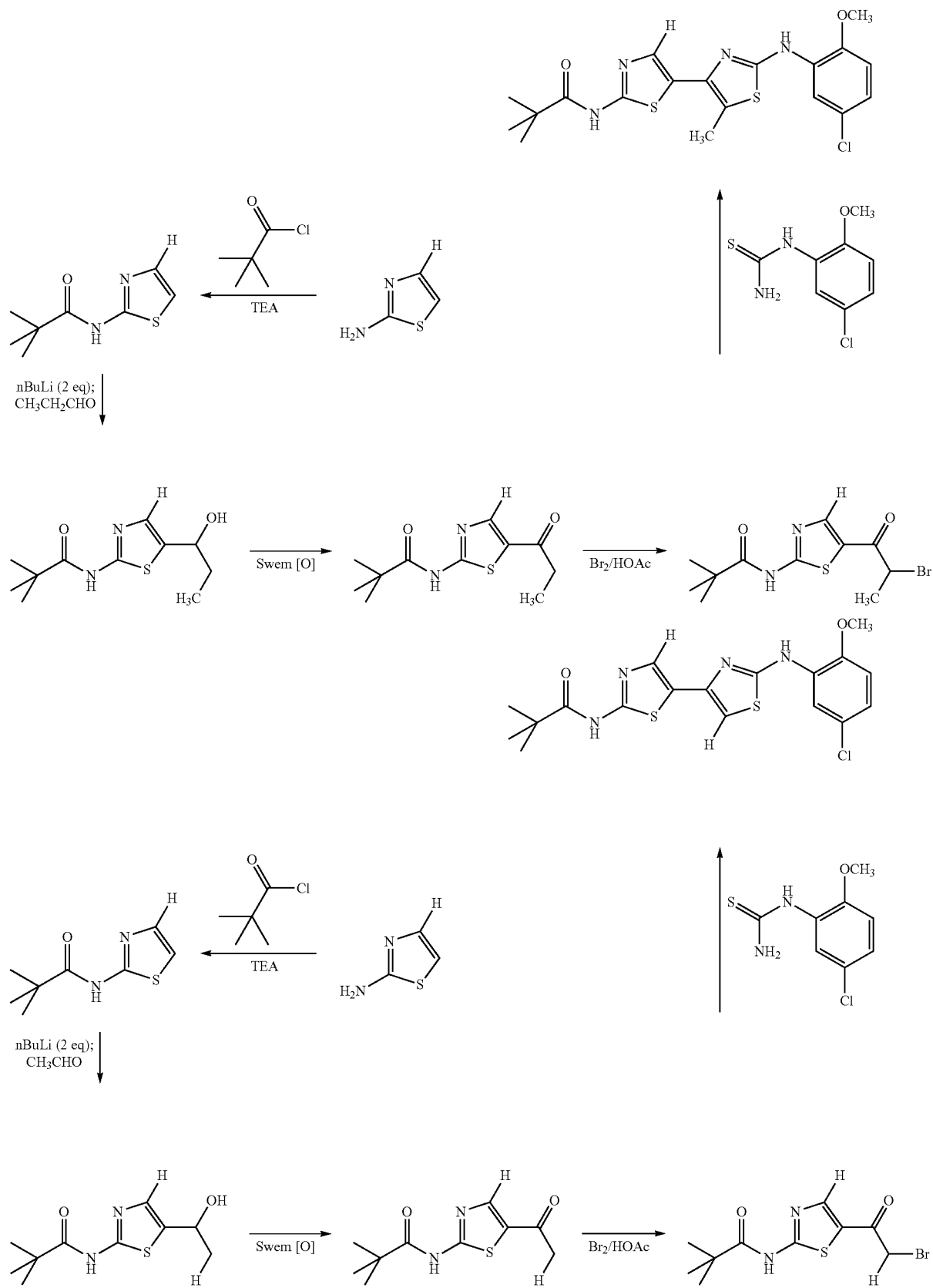

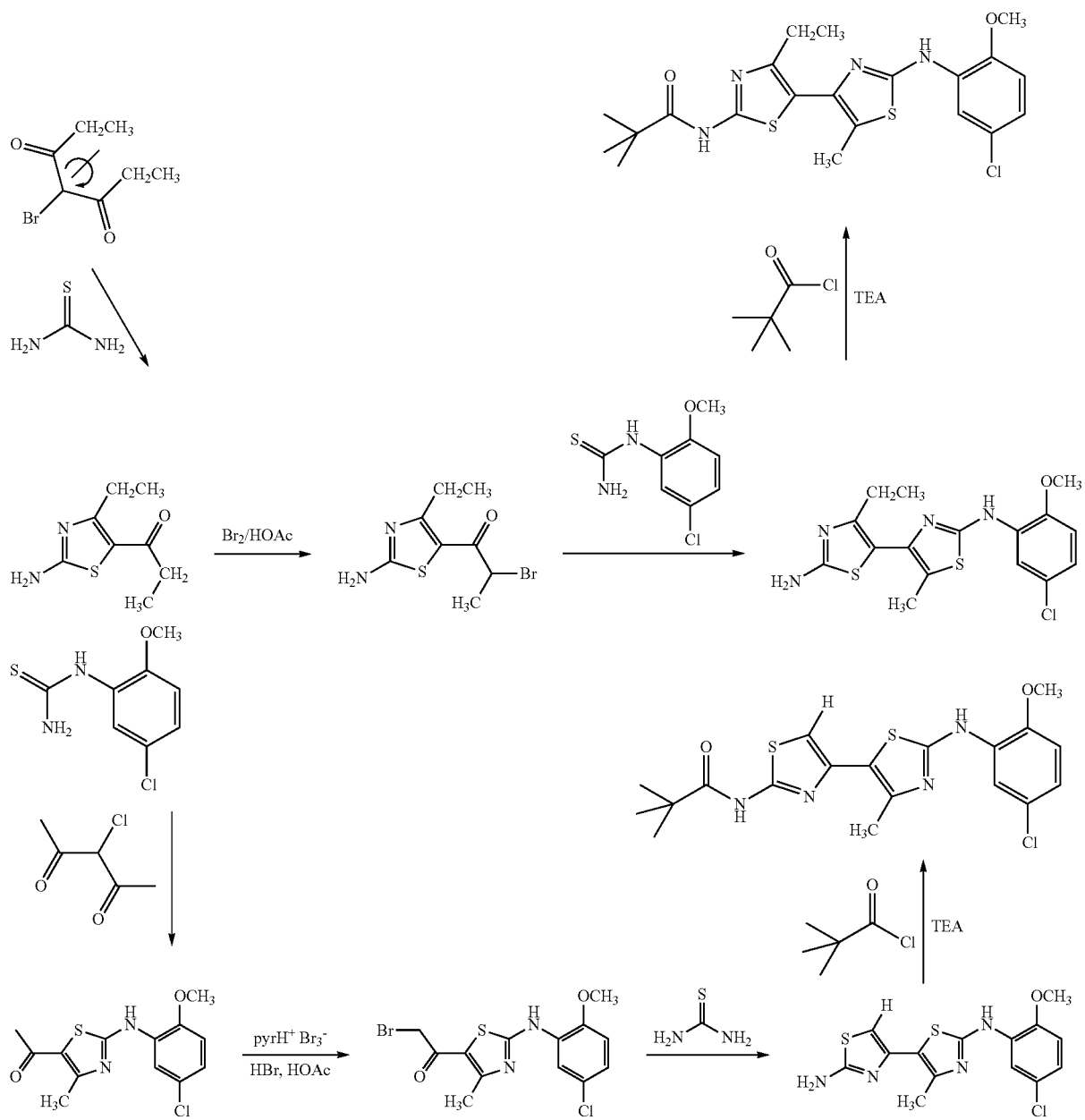

Example 10

Synthesis of Library V Analogs

Figure 5:
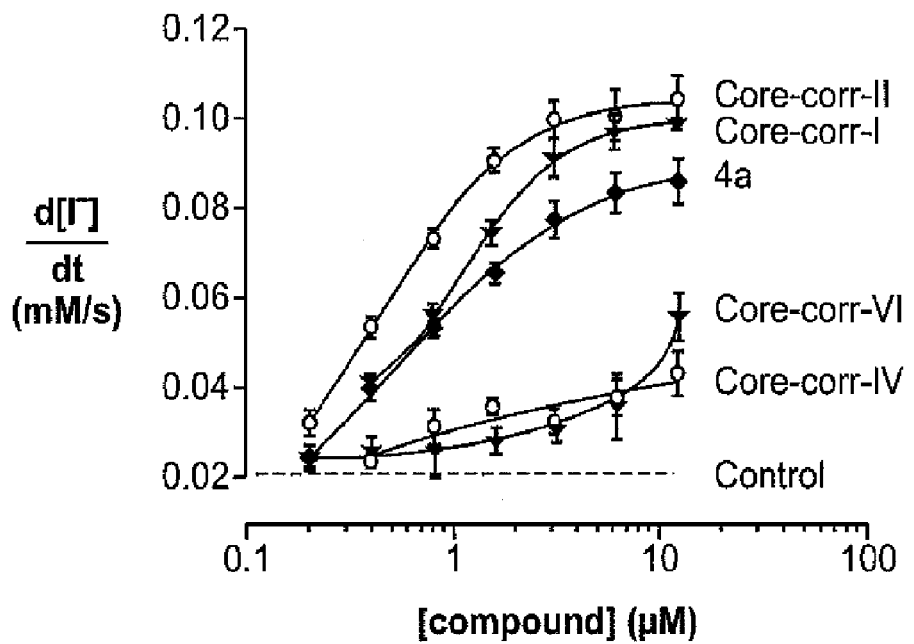
FIG. 5: Dose-response curves comparing select corrector compounds from library sets three, four and five (Libraries III, IV and V) in correcting Δ508-CFTR.

The bridged series of analogs focused on whether constraining bithiazole rotation would affect corrector activity, as well as whether both thiazole rings were necessary. An initial construct containing a "—CH$_2$CH$_2$CH$_2$—" propyl bridge was designed to address this question. The eight step chemistry used to prepare this target is exemplified in Scheme 6. The synthesis of a monothiazole analog is shown below in Scheme 7. As shown in FIG. 5, it was determined that compound Core-corr-II was better than corrector 4 by nearly a factor of two, and that the monothiazole compound was essentially inactive at similar concentrations. Also, compound Core-Corr III is designed and synthesized for a mixed oxazole-thiazole core, and compared against the bithiazole core compounds as described above.

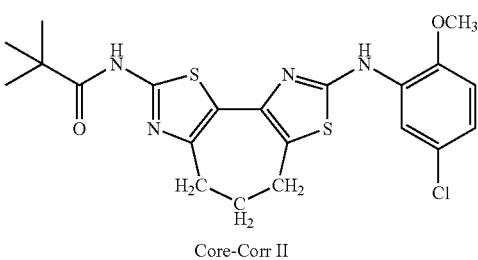

Core-Corr II

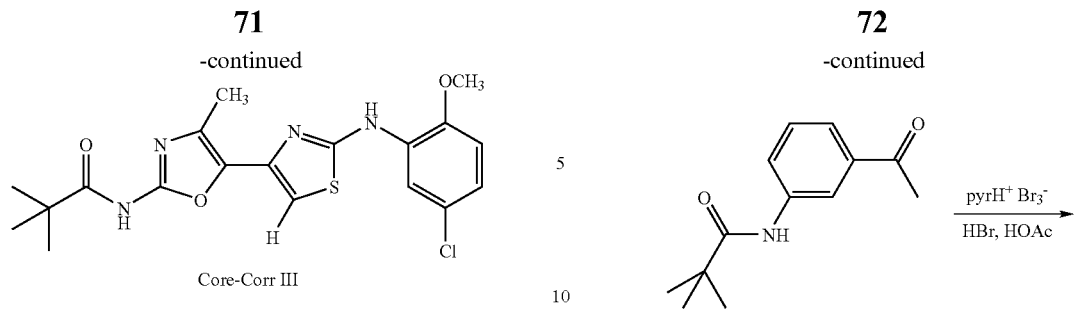
Scheme 6: Synthesis of Library V analogs
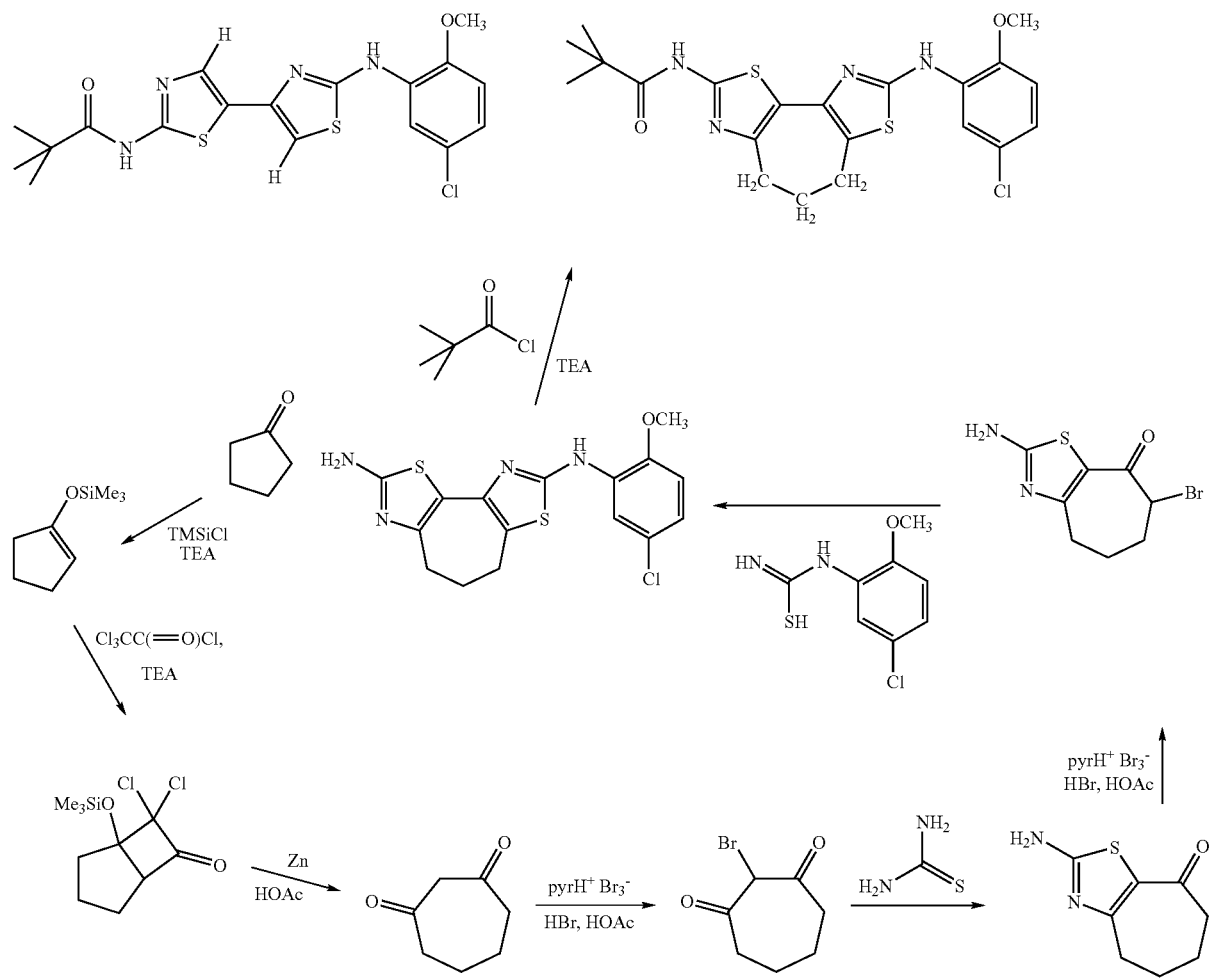
Scheme 7: Synthesis of monothiazole analog Core-Corr VI
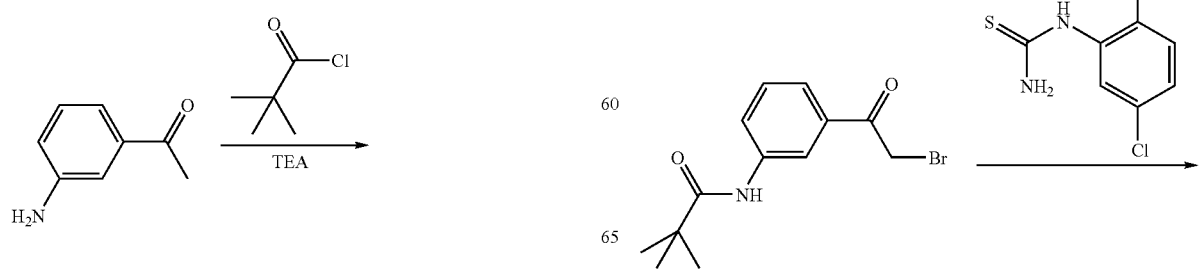

-continued

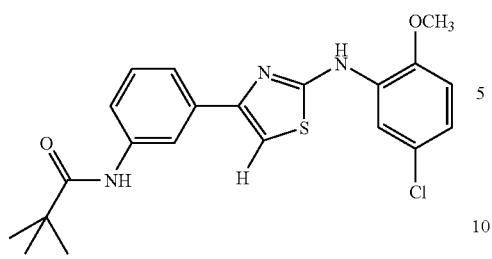

The Core-corr-II bridged bithiazole and additional examples of bridged analogs of interest are illustrated below in Table 4, where R and R' in this context is a substituent for variation, and Ar is an unsubstituted or substituted aryl group for variation.

TABLE 4

Bridged bithiazole analogs

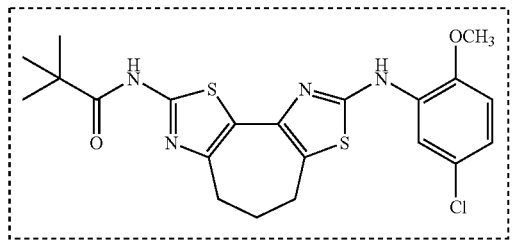 [SMILES: COc1ccc(Cl)cc1Nc1nc2c(s1)CCCc1nc(NC(=O)C(C)(C)C)sc1-2]

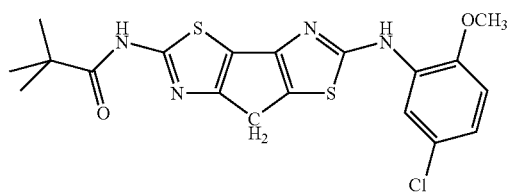 [SMILES: COc1ccc(Cl)cc1Nc1nc2c(s1)Cc1nc(NC(=O)C(C)(C)C)sc1-2]

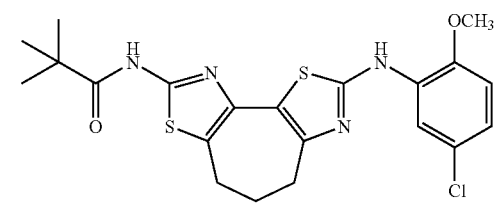 [SMILES: COc1ccc(Cl)cc1Nc1nc2c(s1)-c1nc(NC(=O)C(C)(C)C)sc1CCC2]

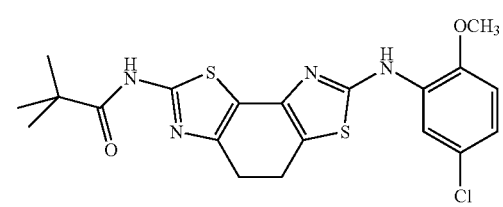 [SMILES: COc1ccc(Cl)cc1Nc1nc2c(s1)CCc1nc(NC(=O)C(C)(C)C)sc1-2]

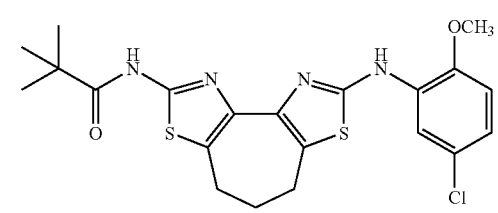 [SMILES: COc1ccc(Cl)cc1Nc1nc2c(s1)CCCc1sc(NC(=O)C(C)(C)C)nc1-2]

TABLE 4-continued

Bridged bithiazole analogs

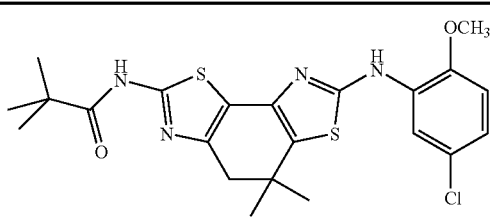

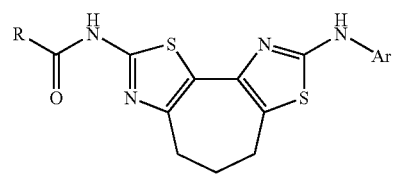

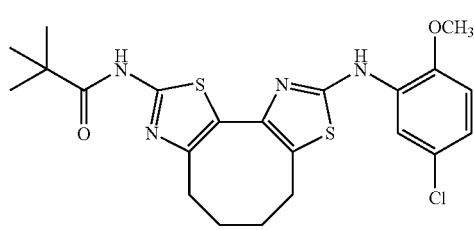 [SMILES: COc1ccc(Cl)cc1Nc1nc2c(s1)CCCCc1nc(NC(=O)C(C)(C)C)sc1-2]

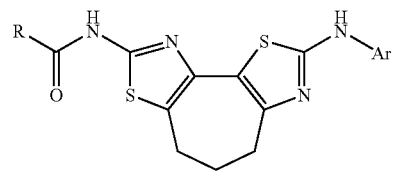

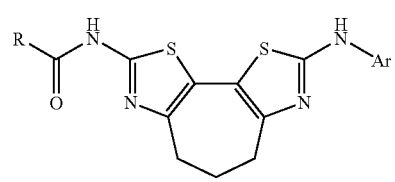

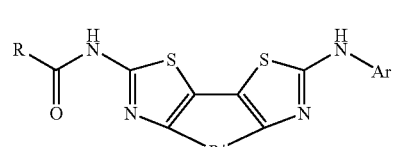

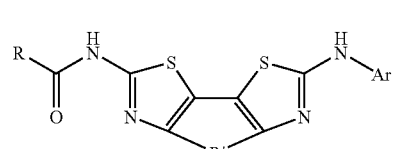

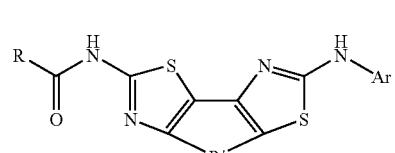

The synthesis schemes for the various exemplary bridged analogs are depicted in Schemes 8-11.

Scheme 8: Synthesis of methyl-bridged bithiazole
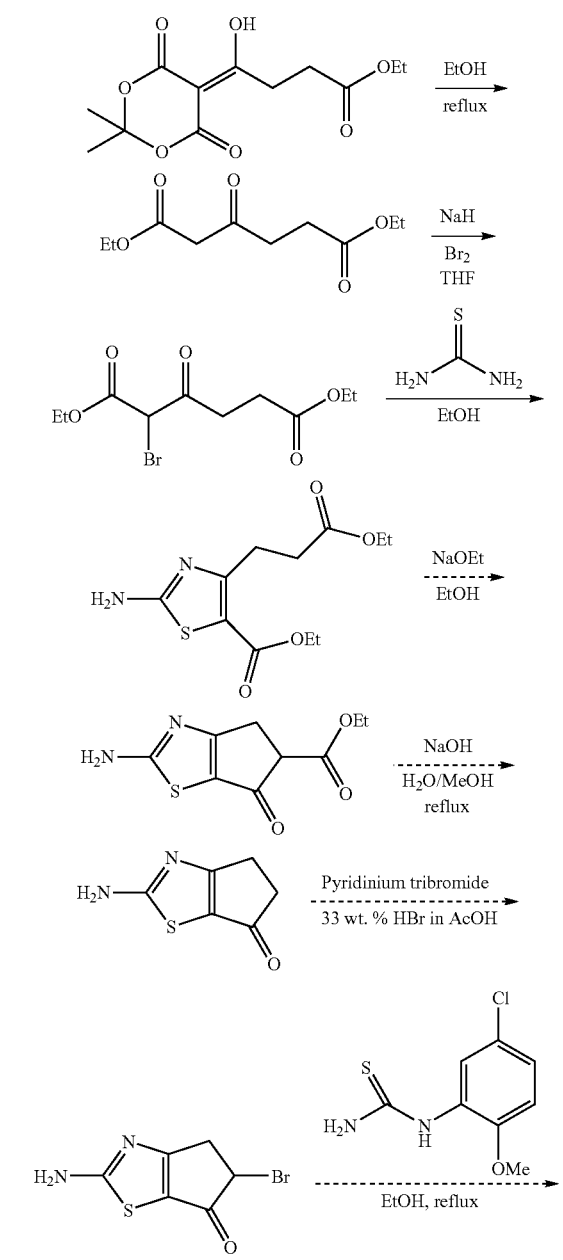
-continued
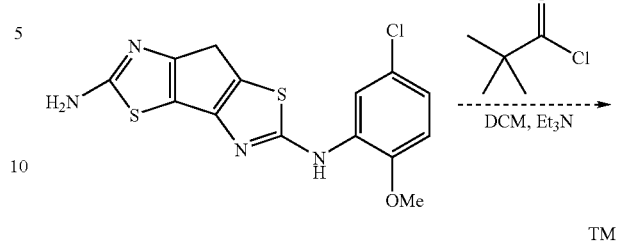
Scheme 9: Synthesis of ethyl-bridged bithiazole
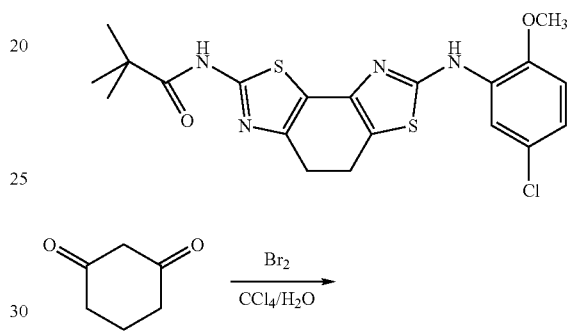
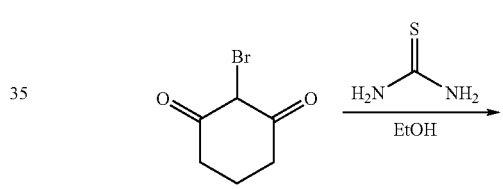
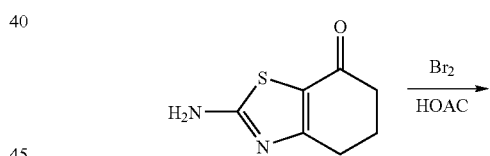
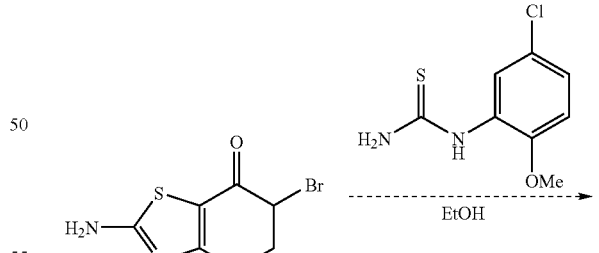
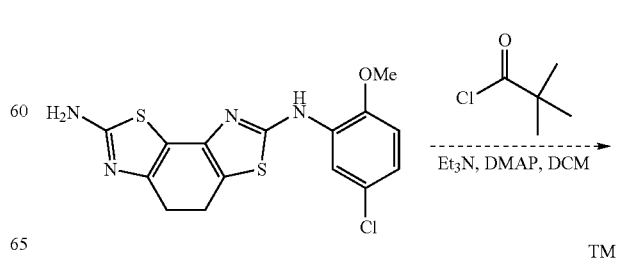

Scheme 10: Synthesis of butyl-bridged bithiazole

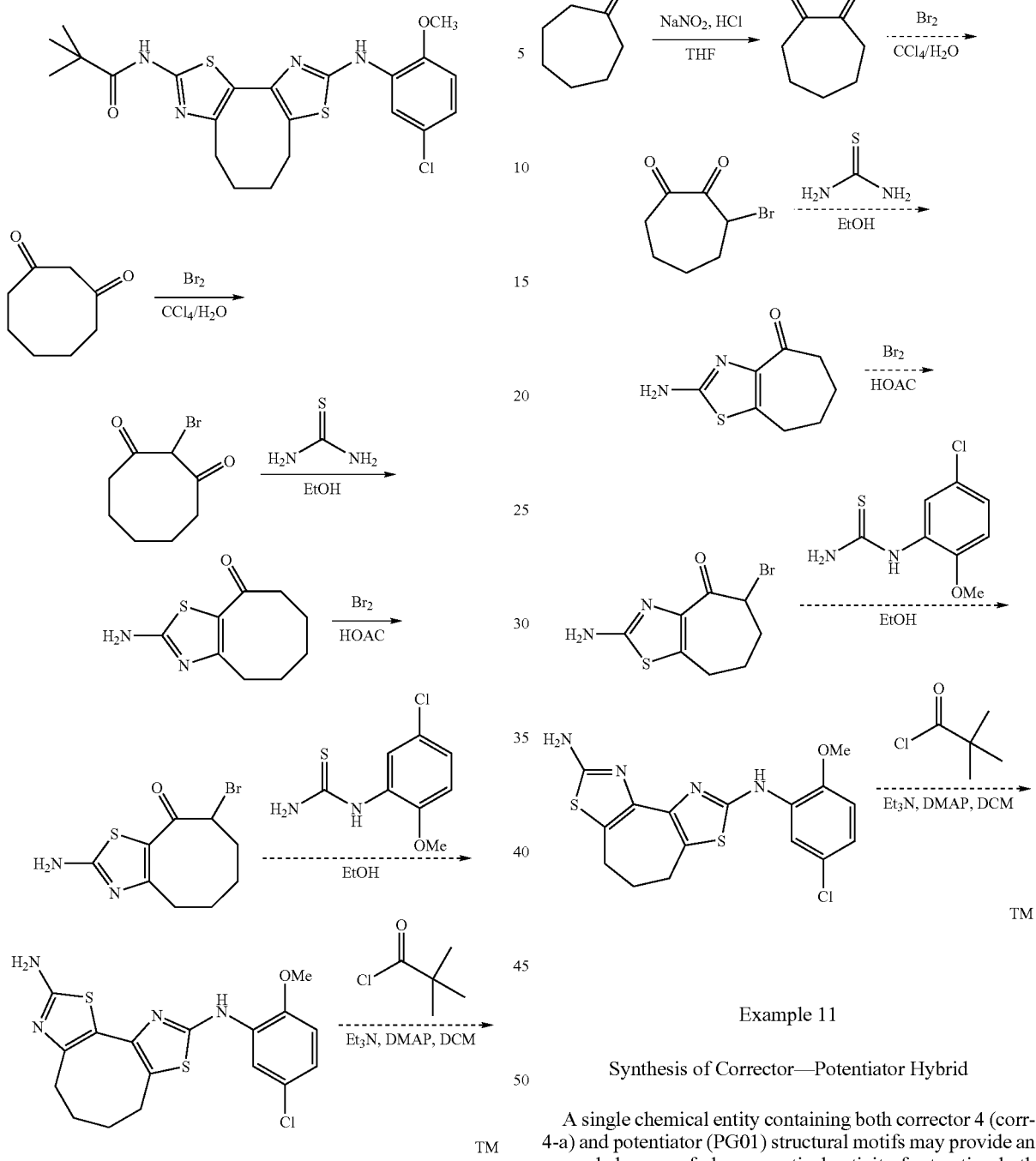

Scheme 11: Synthesis of propyl-bridged inverted bithiazole

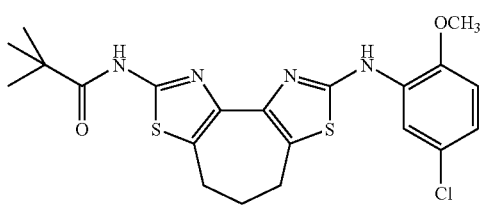

Example 11

Synthesis of Corrector—Potentiator Hybrid

A single chemical entity containing both corrector 4 (corr-4-a) and potentiator (PG01) structural motifs may provide an expanded range of pharmaceutical activity for treating both gating and processing/folding mutants of CFTR. Two designs are YMX and YM1.4 described in above in the section entitled "Hybrid Potentiator-Corrector Compounds."

Construction of hybrid 1 (YM1.4) was carried out as follows. In order to connect the two motifs, the parent corrector and potentiator compounds needed to be slightly modified—but without affecting the core structures bioreactivity. YM1.1 and YM1.2 seemed suitable for this purpose (Scheme 12). Diethylenglycolic acetic acid (YM1.3) was chosen as a linker to tether the two bioreactive cores. Considering the size and hydrophobicity of our target hybrid, an ethylene glycol-based linker was employed to help make the hybrid compound more soluble in aqueous solution.

Scheme 12: Synthesis of Corrector-Potentiator Hybrid

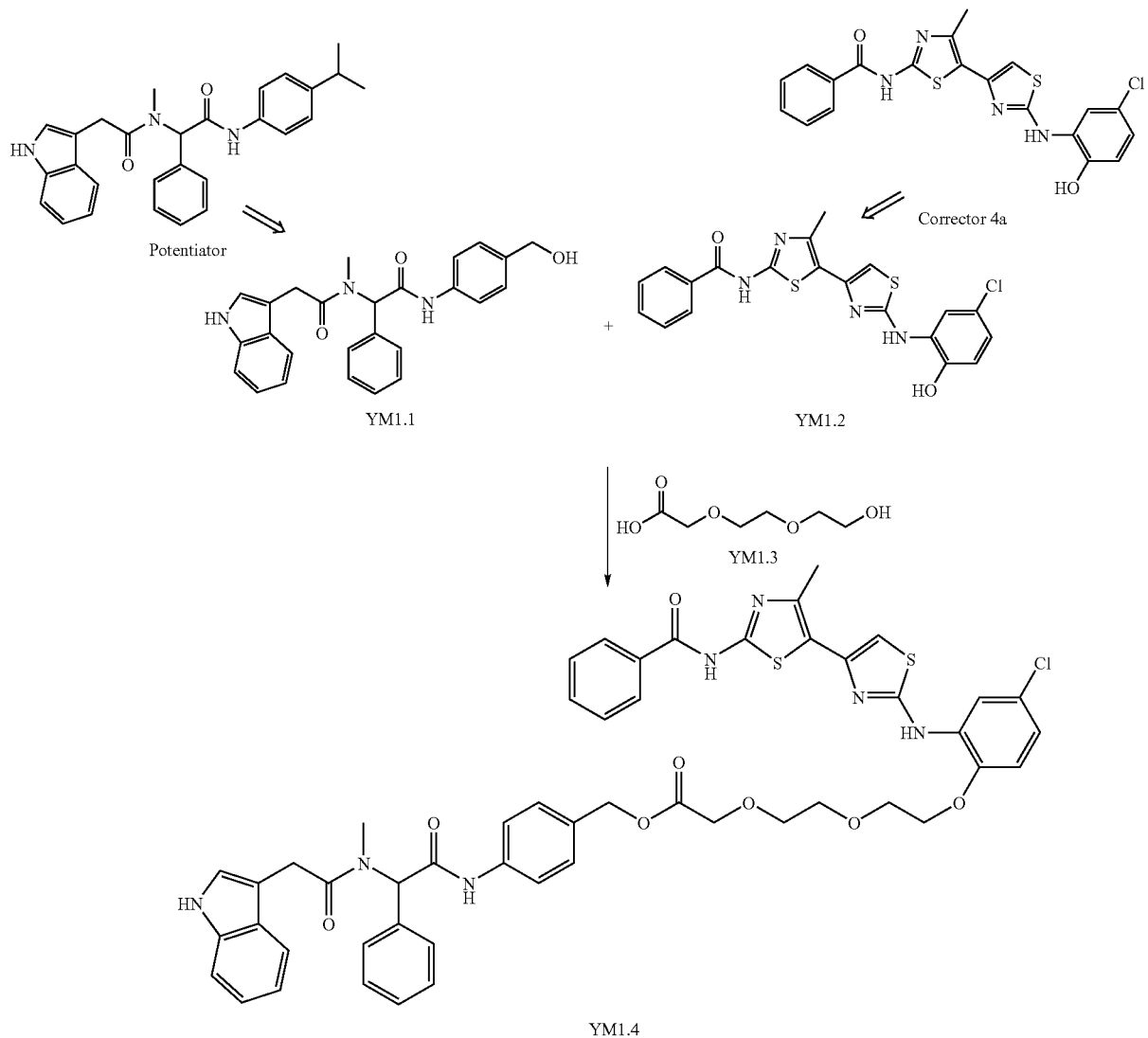

Synthesis of hybrid YM1.4 began by reacting Y1.5 with YM2.1 in ethanol under reflux. This reaction provided the modified corrector fragment YM1.2 in 50% yield (Scheme 13). Connecting YM1.2 with linker YM1.3 using a Mitsunobu coupling was not successful. Upon analysis of the reaction, it was found that linker YM1.3 not only coupled to the phenolic oxygen, but also coupled to the aniline nitrogen resulting in a mixture of YM2.2, YM2.3 and YM2.4, making purification difficult.

Scheme 13: Synthesis of Intermediates and Hybrids YM2.2, YM2.3 and YM2.4

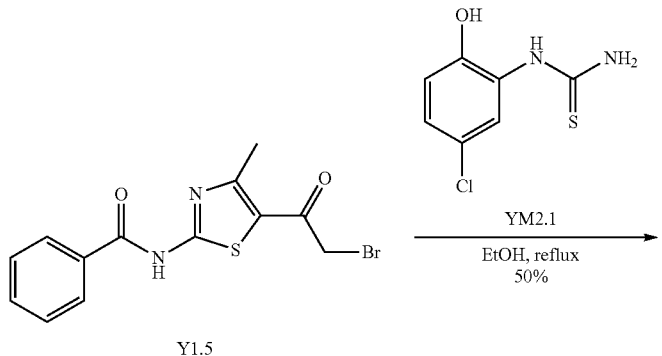

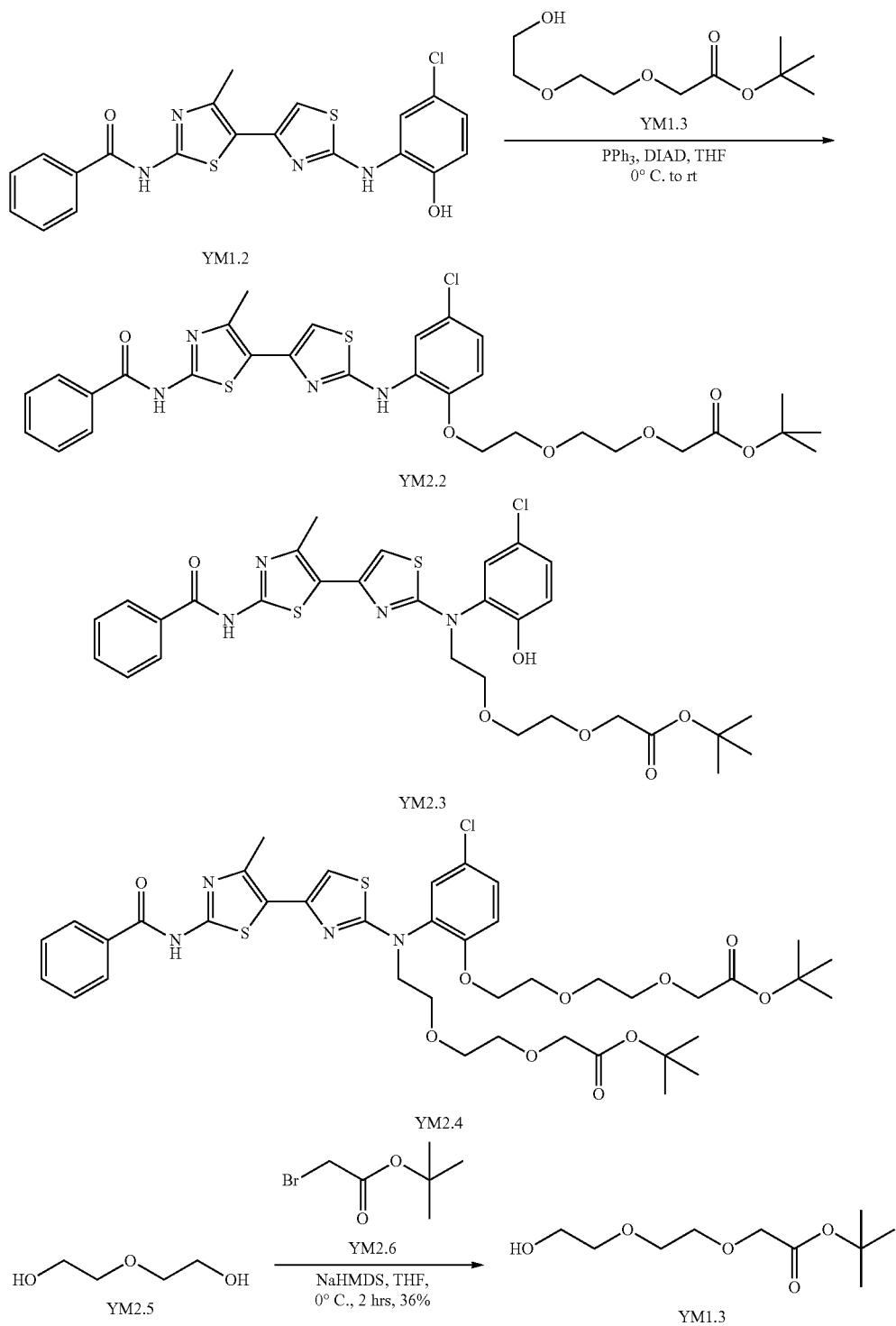

Fortunately, it was determined that thiourea intermediate YM3.5 provides a solution for this problem (Scheme 14). YM3.5 contains the diethylene glycolic acetic acid liker and by experience we knew that reacting YM3.5 with Y1.5 would proceed without problem. Key intermediate YM3.5 was prepared through 4 steps. First, 2-nitro-4-chlorophenol (YM3.1) was coupled with the linker YM1.3 and the nitro group on the resulting product (YM3.2) was then reduced by stannous chloride in ethanol. Treating YM3.3 with thiophosgene gave isothiocyanate YM3.4 and, by passing ammonia gas through a dichloromethane solution of YM3.4, provided the key intermediate YM3.5 in quantitative yield. The cyclization reaction of YM3.5 with Y1.5 followed by deprotection of the tertiary butyl ester of diethylene glycol linker afforded YM3.6.

Scheme 14: Synthesis of YM3.6
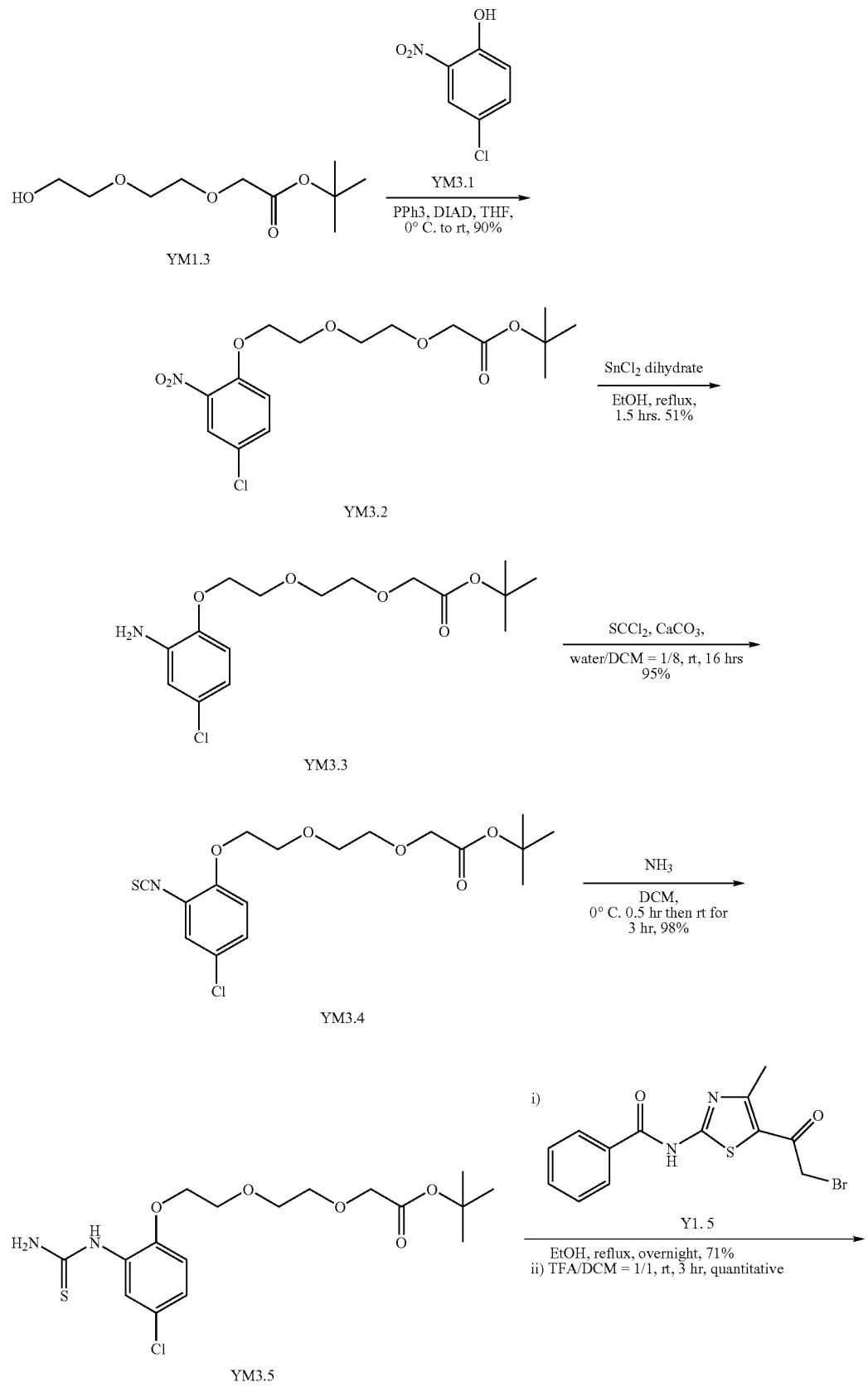

-continued

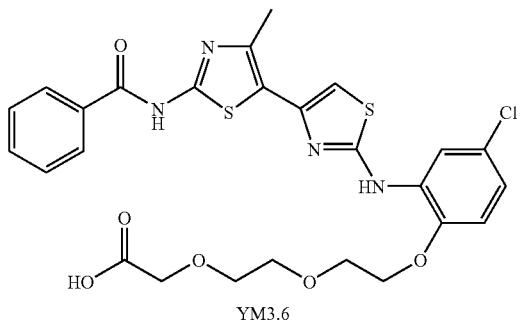 [SMILES: Cc1nc(NC(=O)c2ccccc2)sc1-c1csc(Nc2cc(Cl)ccc2OCCOCCOCC(=O)O)n1]
YM3.6

4-Aminobenzyl alcohol was coupled with Boc-Me-aminophenylglycine M1.1. Boc deprotection of YM4.2 gave amine YM4.3 which was coupled to 3-indole acetic acid M1.4 with EDC/DMAP (Scheme 15) to give the targeted potentiator fragment YM4.4. Finally, acid coupling reaction of YM3.6 with YM4.4 gave hybrid YM1.4 in 11% yield. We assume that this poor yield was presumably due to the poor solubility of YM3.6 in the reaction solvent.

Scheme 15: Synthesis of key YM4.4 and Hybrid YM1.4

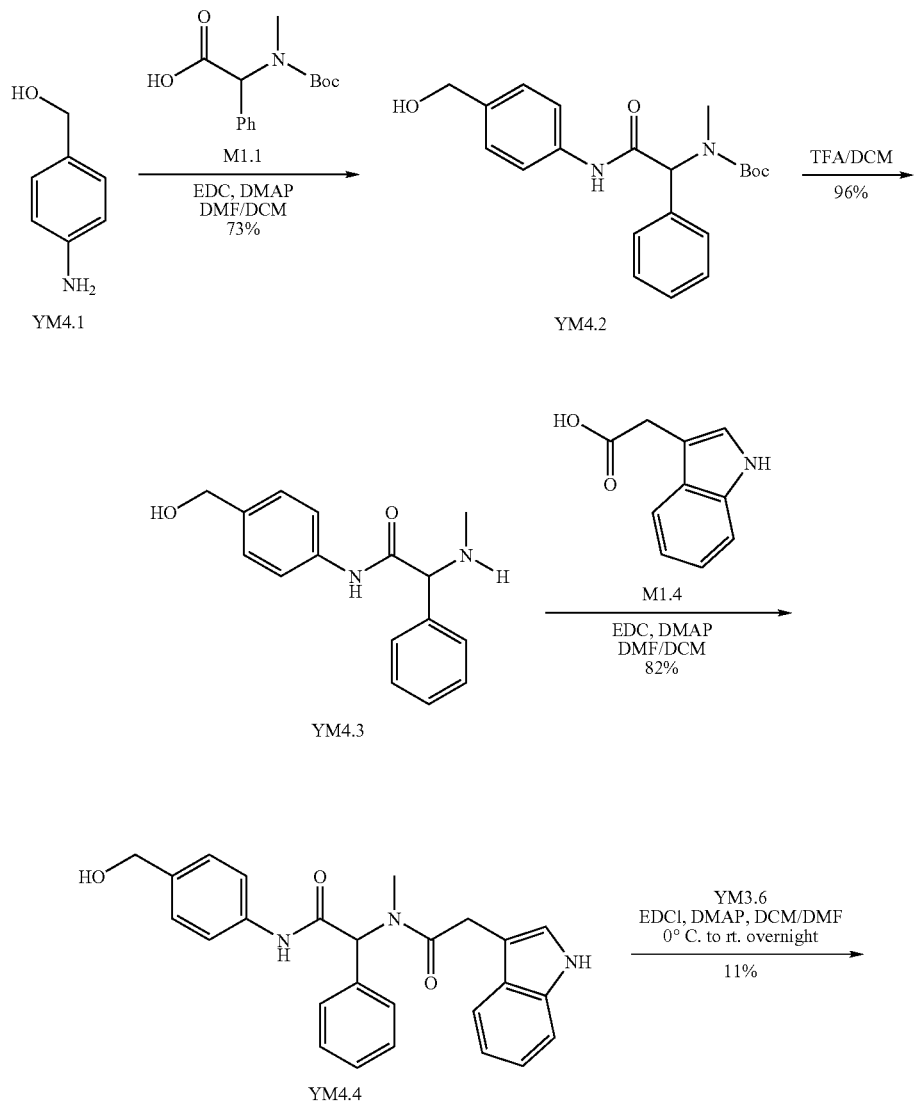

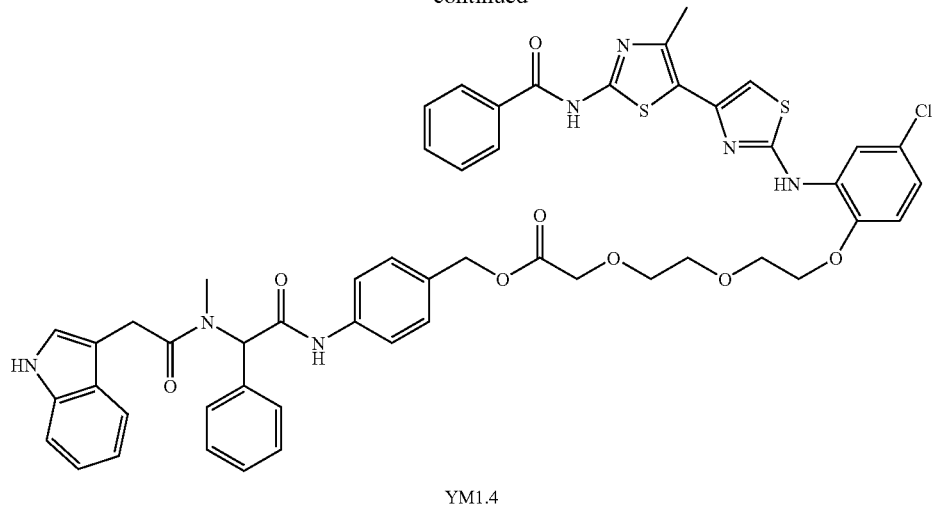

YM1.4

Example 12

Analysis of ΔF308-CFTR Potentiator Activity for Hybrid Analogs

Figure 6:
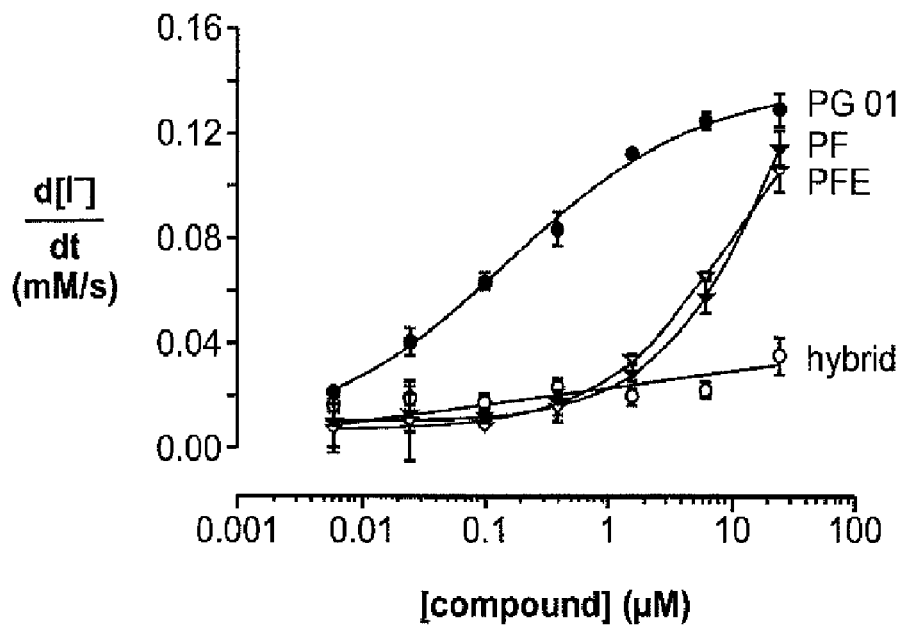
FIG. 6: Dose-response curves for potentiator compounds PG01, PF and PFE relative to a hybrid corrector-potentiator compound YM1.4 in potentiating Δ508-CFTR.
Figure 7:
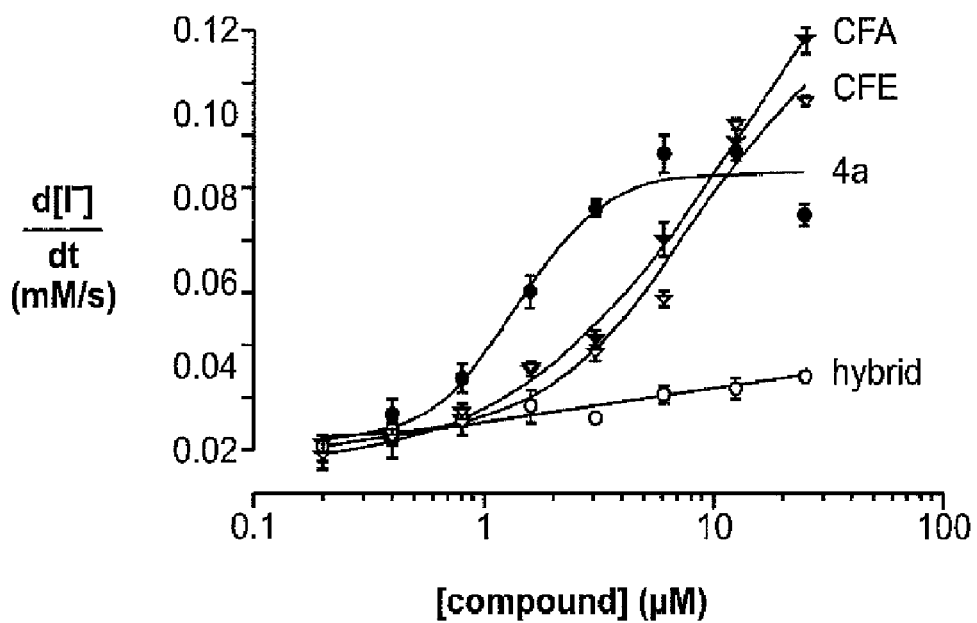
FIG. 7: Dose-response curves for corrector compounds CFA, CFE, and Core 4a relative to a hybrid corrector-potentiator compound YM1.4 in correcting ΔF508-CFTR.

Hybrid compound YM1.4 and all of the key synthetic intermediates were tested for activity against ΔF508-CFTR along with controls, some of the structures of which are shown in Table 5. The results are shown in FIGS. 6 and 7. Hybrid compound YM1.4 was not active as either a potentiator or as a corrector in the in vitro assay. However, it is believed that YM1.4 may function as a prodrug that may be converted in vivo to active potentiator and corrector components upon hydrolysis of the ester linkage. For instance, key intermediate YM3.6 showed excellent activity as a corrector. Also, corrector fragment YM3.6 bearing the linker showed better activity than the corrector fragment YM1.2 itself. This fact is encouraging if the ester moiety of hybrid YM1.4 is cleaved in the metabolic pathway in vivo, as ester bonds are often cleaved by enzymes. Since YM4.4 also showed moderate activity as a potentiator as well, hybrid YM1.4 may exhibit activity in vivo as a prodrug.

TABLE 5

Compound set for corrector-potentiator activity assays

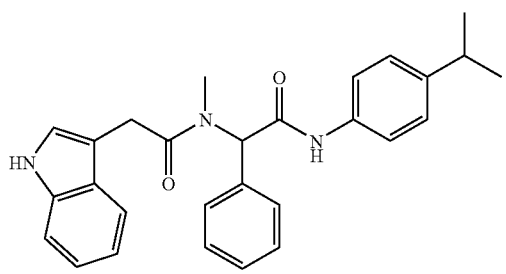

PG01

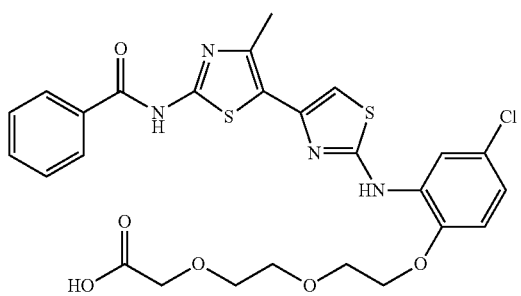

YM3.6 (CFA)

TABLE 5-continued
Compound set for corrector-potentiator activity assays
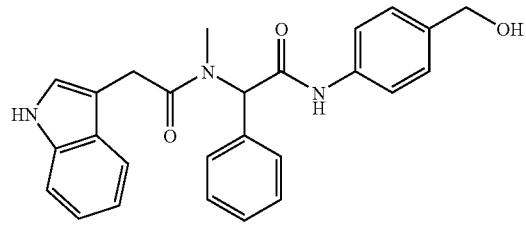
YM4.4 (PF)
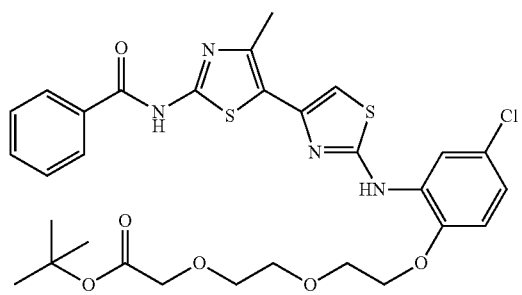
YM2.2 (CFE)
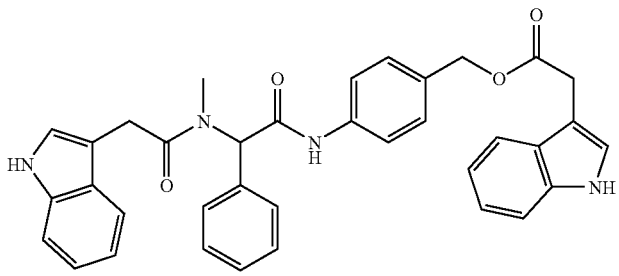
PFE
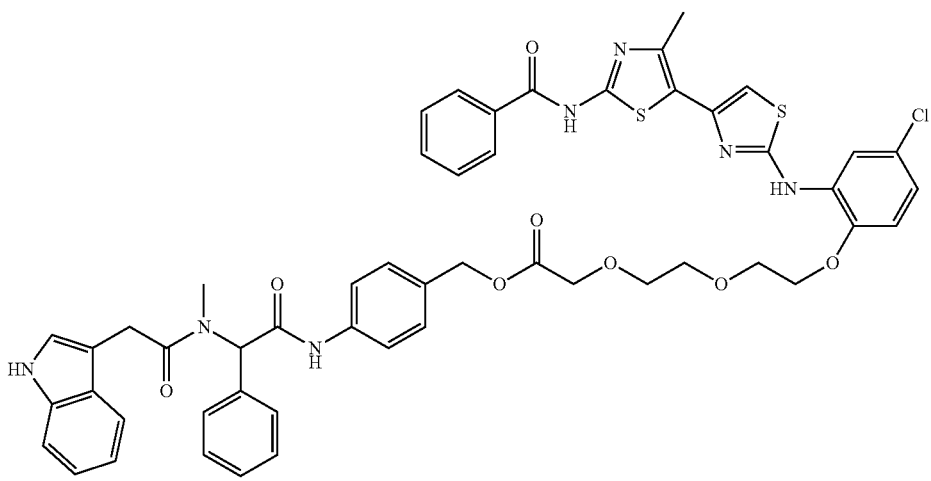
YM1.4 (hybrid)

Example 13

Potent s-cis Bithiazole Correctors of ΔF508 Cystic Fibrosis Transmembrane Conductance Regulator Cellular Processing N-(5-(2-(5-Chloro-2-methoxyphenylamino)thiazol-4-yl)-4-methylthiazol-2-yl)pivalamide 1z is found to correct defective cellular processing of the cystic fibrosis protein ΔF508-CFTR. Eight C4'-C5 C,C-bond-controlling bithiazole analogs of 1z were designed, synthesized, and evaluated to establish that constraining rotation about the bithiazole-tethering has a significant effect on corrector activity. For example, constraining the C4'-05 bithiazole tether in the s-cis conformation [N-(2-(5-chloro-2-methoxyphenylamino)-7,8-dihydro-6H-cyclohepta[1,2-d:3,4-d]bithiazole-2'-yl)pivalamide; 29z] results in improved corrector activity. Heteroatom placement in the bithiazole core is also a factor as evidenced by the loss of corrector activity with s-cis constrained N-(2-(5-chloro-2methoxyphenylamino)-5,6-dihydro-4H-cyclohepta[1,2-d:3,4-d]bithiazole-2'-yl)pivalamide 33z. In addition, computational models were utilized to examine the conformational preferences for select model systems. Following our analysis, the "s-cis locked" cycloheptathiazolothiazole 29z was found to be a potent bithiazole corrector, with an $IC_{50}$ of about 450 nM.

Figure 8:
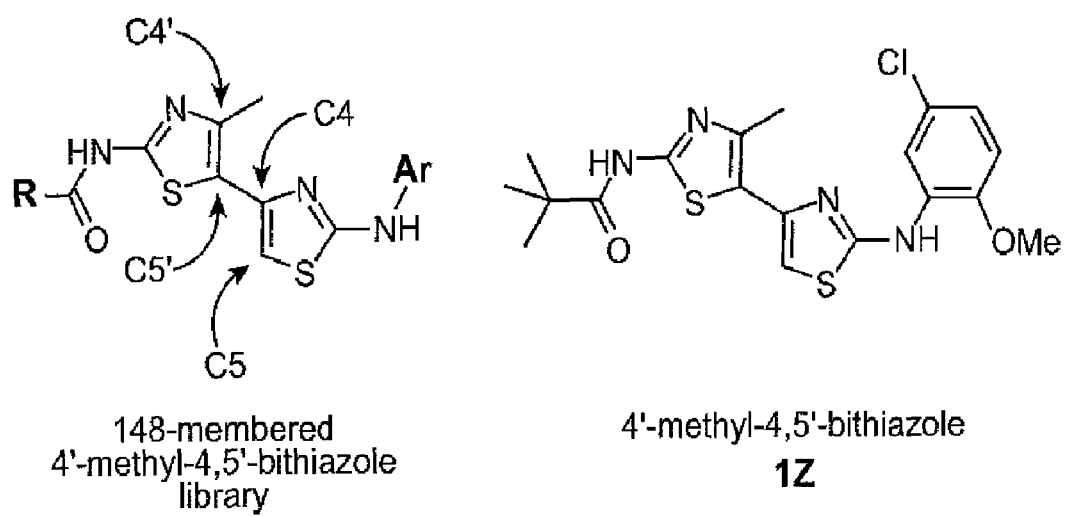
FIG. 8: Examples of small molecule bithiazole correctors of ΔF508-CFTR.

Analyses of the specificity, cellular mechanism, and efficacy in human CF cells of four chemical classes of active compounds identified from the screen established methylbithiazoles as promising for further development. A subsequent synthesis and screening study of about 148 methylbithiazole analogs focused on the peripheral amide and aniline substructures, as shown in FIG. 8, established initial structure activity relationship (SAR) data for this class of correctors with methylbithiazole corrector 1z having corrector efficacy. The example herein explores the bithiazole core structure of 1z to establish certain structural features of the bis-heterocyclic portion of bithiazole ΔF508-CFTR correctors.

Results and Discussion

Figure 9:
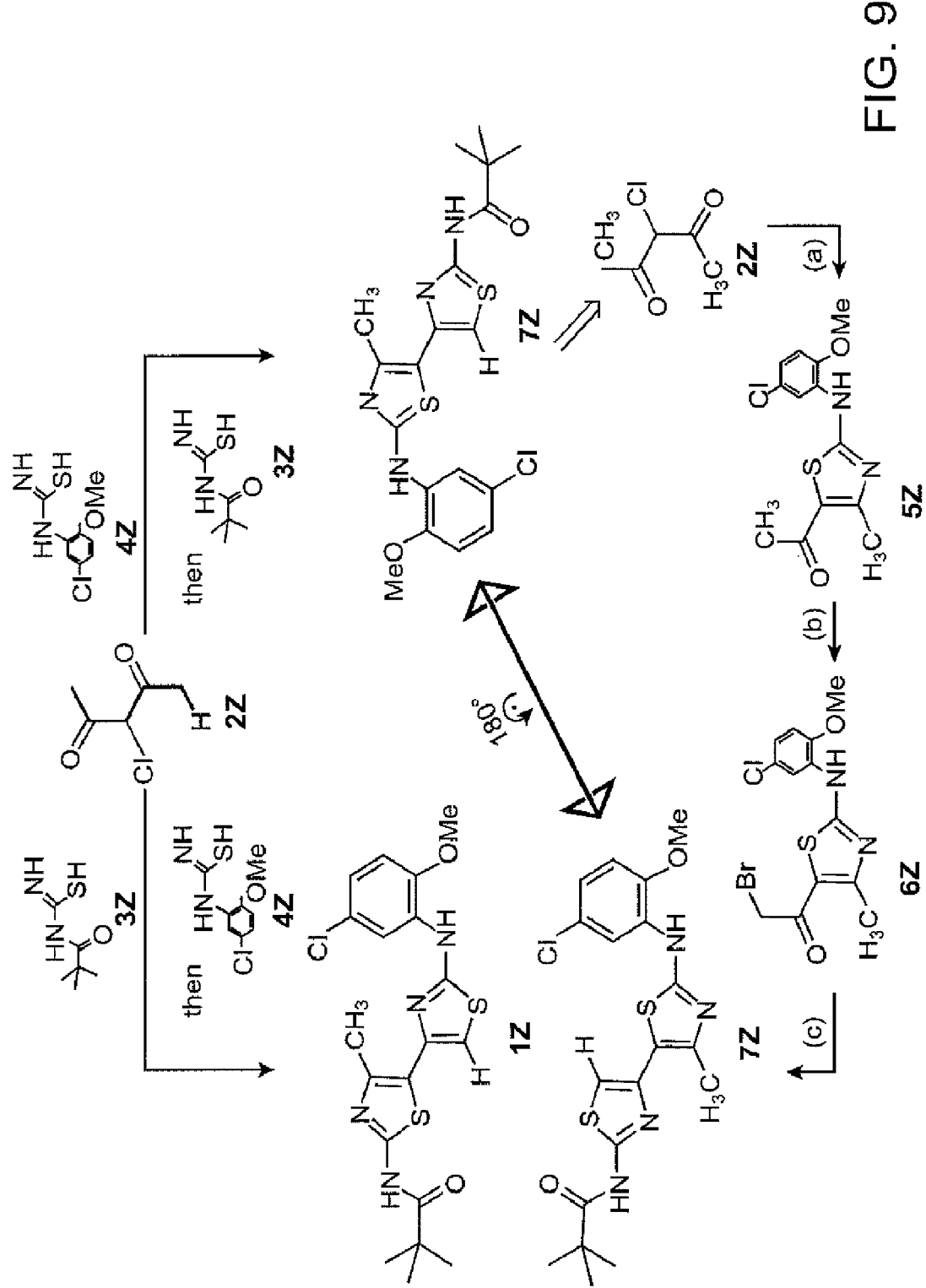
FIG. 9: Synthetic scheme of 7z.

One objective was to determine if the bithiazole substructure of 1z plays a role in ΔF508-CFTR corrector activity or if it simply orchestrates the proper 3-dimensional placement of the flanking pivalamide and 5-chloro-2-methoxyaniline substructures. To accomplish this, the C2 symmetry of 3-chloropentane-2,4-dione (2z) was divergently exploited to prepare, from this one starting material, both 1z and 7z as detailed in FIG. 9. The preparation of corrector 1z was accomplished by condensation of chlorodiketone 2z with —N-pivaloylcarbamimidothioic-acid (3z) to give a 1-(thiazol-5-yl)ethanone intermediate. Bromination alpha to the carbonyl of this thiazole and subsequent condensation with N-(5-chloro-2-methoxyphenyl)carbamimidothioic acid (4z) delivers 1z By transposing the thiazole formation order, analog 7z is obtained from the same starting material (2z) as 1z. That is, condensation of 2z first with 4z followed by a-bromination and subsequent condensation with the equivalent of 3z (e.g., thiourea condensation followed by N-acylation with pivaloyl chloride) delivers transposed bithiazole 7z where the bithiazole core has been inverted relative to the topography set by the appended pivalamide and 5-chloro-2-methoxyaniline substructures.

Figure 10:
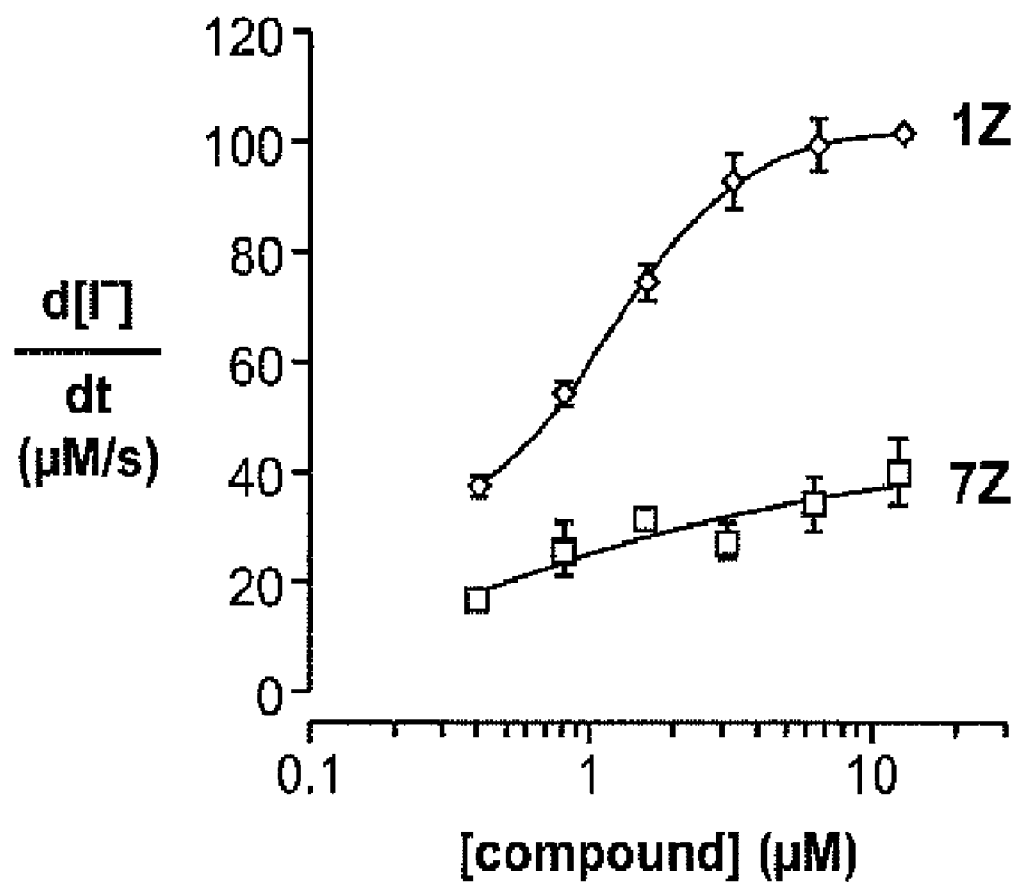
FIG. 10: Concentration-activity profiles of 1z and 7z.

FIG. 10 shows that this bithiazole transposition in 7z results in substantial loss of ΔF508-CFTR corrector activity as assayed in FRT epithelial cells stably coexpressing human ΔF508-CFTR and the high-sensitivity halide-sensing fluorescent protein YFP-H148Q/I152L. Since the conformational biases of 1z and 7z should be nearly identical, this change in corrector activity has certain implications: (i) proper 3-dimensional display of the pivalamide and 5-chloro-2-methoxyaniline substructures is insufficient for corrector activity; (ii) the substituted bithiazole core is a contributor to the activity of 1z; and (iii) while the target of 1z remains substantially unknown, the remarkable activity differences for these two quite similar bithiazoles suggests that the activity of 1z may be the consequence of a specific ΔF508-CFTR binding event.

Figure 11:
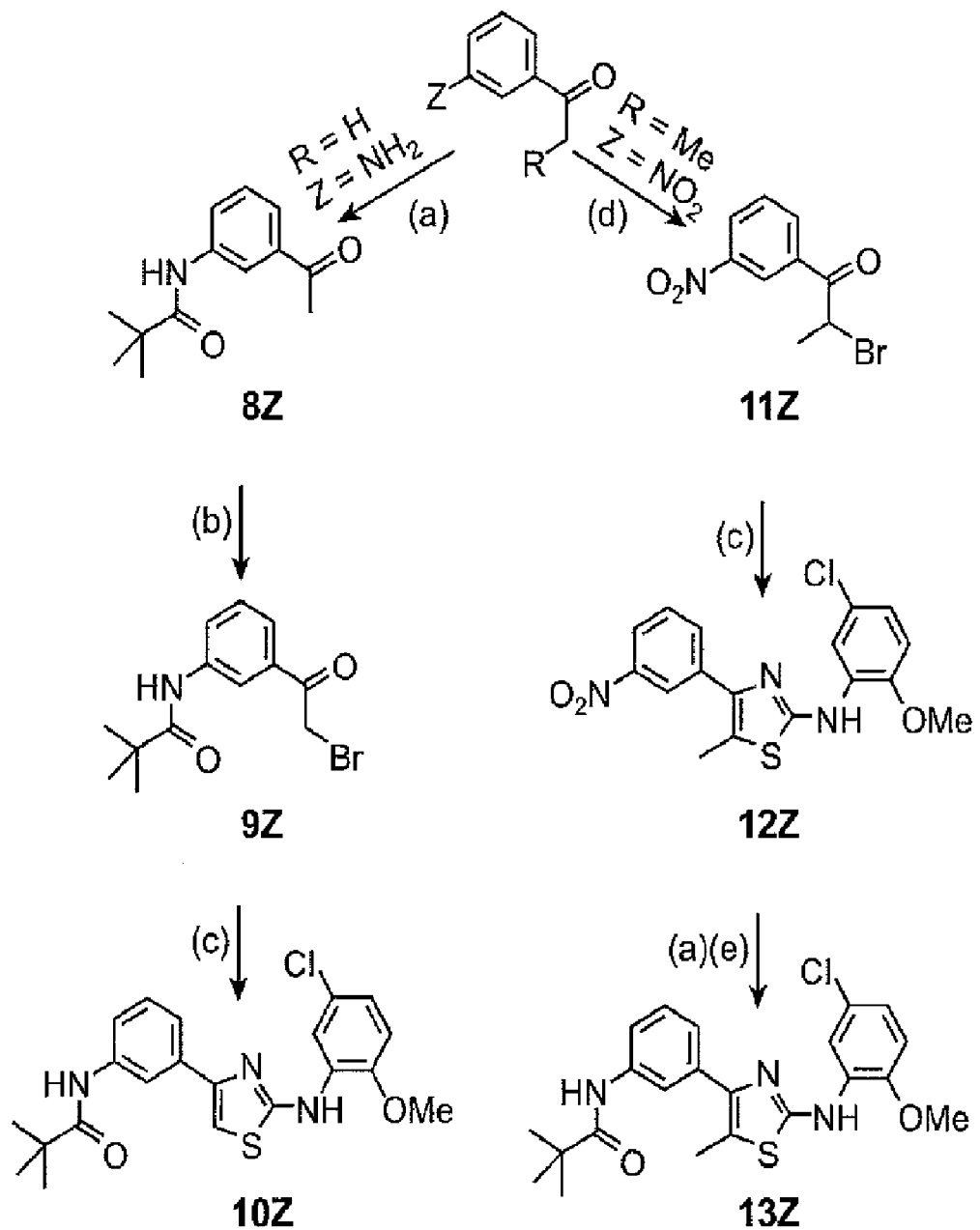
FIG. 11: Synthetic schemes of 10z and 13z.

To initially explore the implications of (ii) above, the next objective was to partially modify the bithiazole core structure by replacing one of the thiazole rings with a phenyl ring. The chemistry to accomplish this objective is detailed in FIG. 11 and starts with 1-(3-aminophenyl)ethanone. N-Acylation of the aniline moiety with pivaloyl chloride was followed by bromination alpha to the carbonyl. Subsequent condensation of this bromoacetophenone with 4z delivered the 4-phenylthiazole analog 10z. Starting with 1-(3-nitrophenyl)propan-1-one, a sequence consisting of bromination, thiazole formation, Sn(II)-mediated nitro reduction and subsequent N-acylation delivers the 5-methylthiazole analog 13z. ΔF508-CFTR assay results for 10z and 13z reveal that each of these 4phenylthiazole compounds do not substantially have ΔF508-CFTR corrector activity.

The substantial lack of corrector activity for 7z, 10z, and 13z is consistent with the bithiazole core being a determinant of the corrector activity of 1z. Bithiazole analogs that would probe structural and conformational features of the central bis-heterocycle were designed. One aspect of the 4'-methyl-4,5'-bithiazole moiety that could greatly affect its activity involves the dihedral angle of the thiazole-tethering C(4)-C(5') bond (see FIG. 8 for the numbering scheme).

Figure 12:
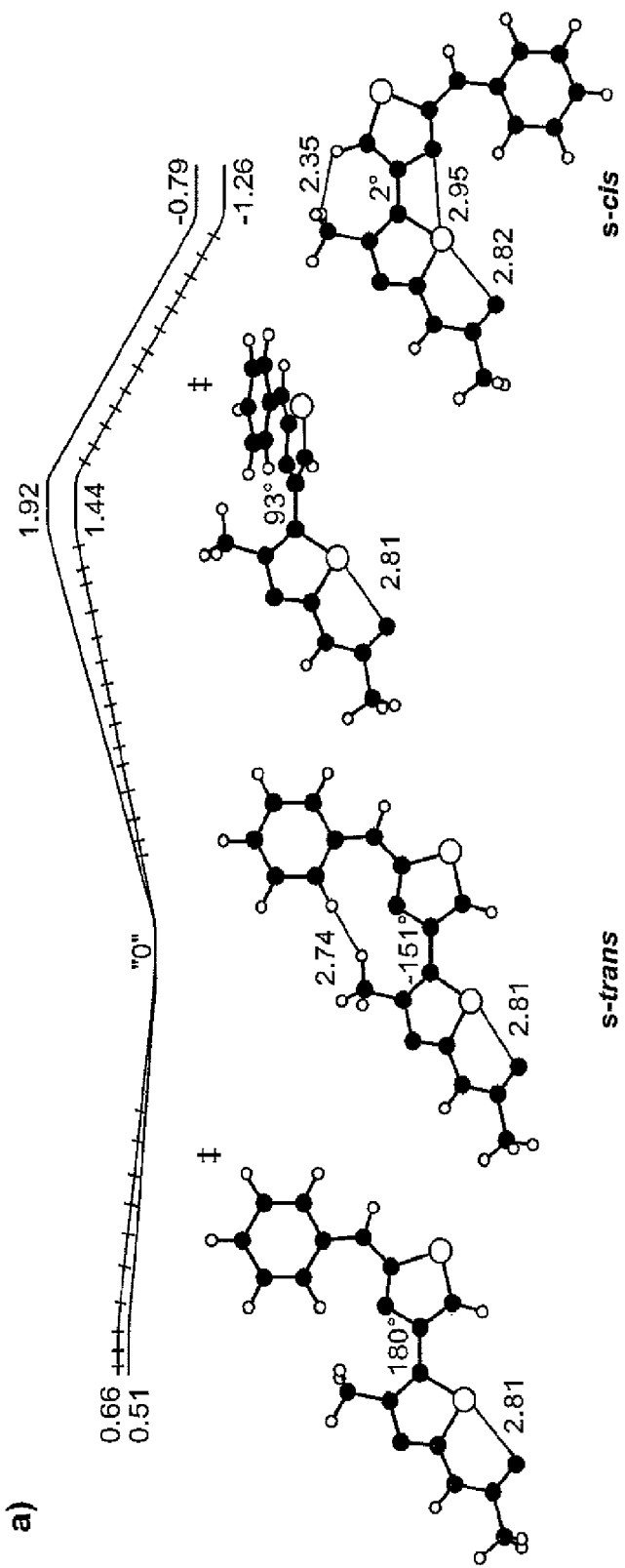
FIG. 12: (a) Structures and associated energies for model of 1z. From left to right, the structures shown are: transition state structure for interconversion of enantiomeric s-trans conformations, one enantiomeric s-trans minimum, the transition state structure for interconversion of the s-trans and s-cis minima, and the s-cis minimum. Selected distances are shown in angstroms; dihedral angles shown are for the central C—C—C—C substructure; energies in kcal/mol relative to the s-trans minimum; gas-phase values in straight line, single point calculations in water in slashed line. (b) Structural consequences of a 180° rotation about the C(4)-C(5') bithiazole bond.
Figure 12:
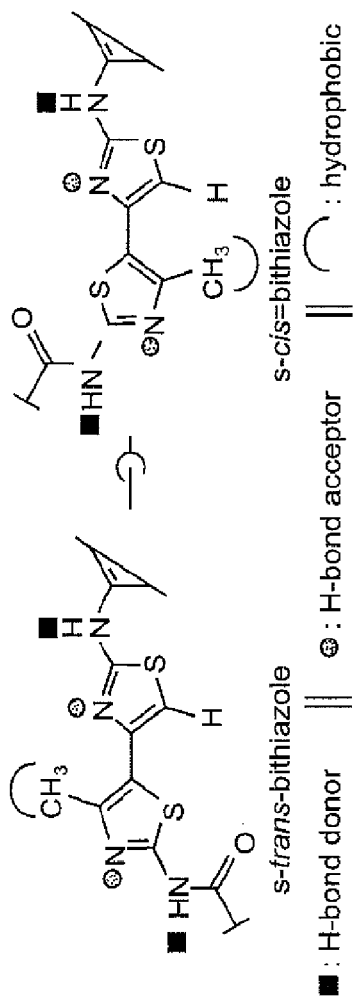

As depicted in FIG. 12a, the 4'-methyl-4,5'-bithiazole system can adopt two approximately planar conformations: a conformation where the C(4')—$CH_3$ substituent is s-trans to the C(5)-H, and a conformation where the C(4')—$CH_3$ substituent is s-cis to the C(5)-H. Interestingly, based on quantum chemical calculations (FIG. 12a), the s-cis conformer is actually slightly lower in energy (by about 1 kcal/mol), despite the potential steric clash between the C(4')—$CH_3$ and the C(5)-H. This appears to be the result of an attractive S . . . N interaction. The preferred conformation of the amide group in 1z (that shown in FIG. 12a) also displays an S . . . X interaction, in this case between a thiazole S and the amide carbonyl O. The s-trans conformer is also twisted from planarity, although planarization of this structure (FIG. 12a, left) is associated with a very small energetic penalty. The barrier for conversion of the s-cis to the s-trans conformation is about 2-3 kcal/mol, so these structures can be expected to interconvert freely in solution. However, as depicted in FIG. 12b, the structural profiles of the s-trans and s-cis bithiazole conformations are quite distinct from one another in how they present bithiazole structural features such as H-bond donors, H-bond acceptors, and the hydrophobic C(4')—CHs.

Figure 13:
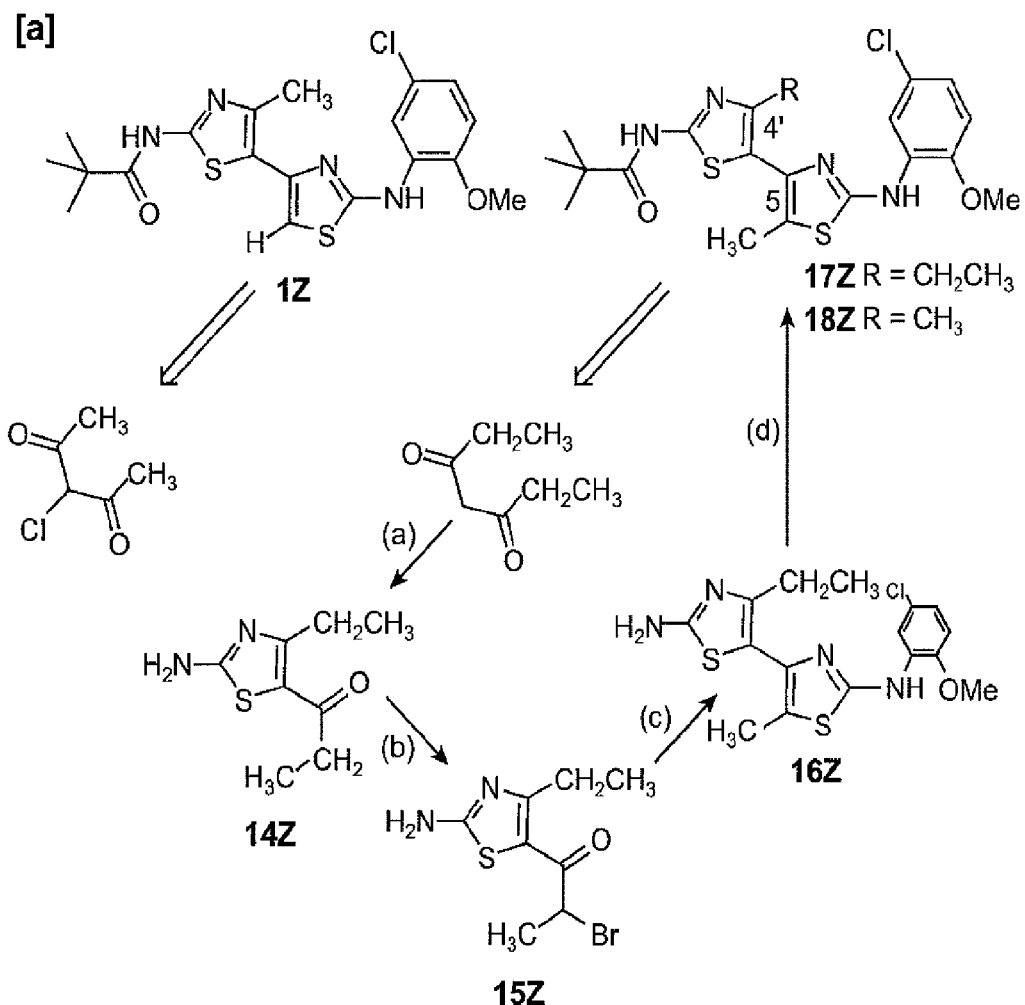
FIG. 13: (a) Synthetic scheme of 17z. (b) Concentration-activity analysis of 1z and 17z.
Figure 13:
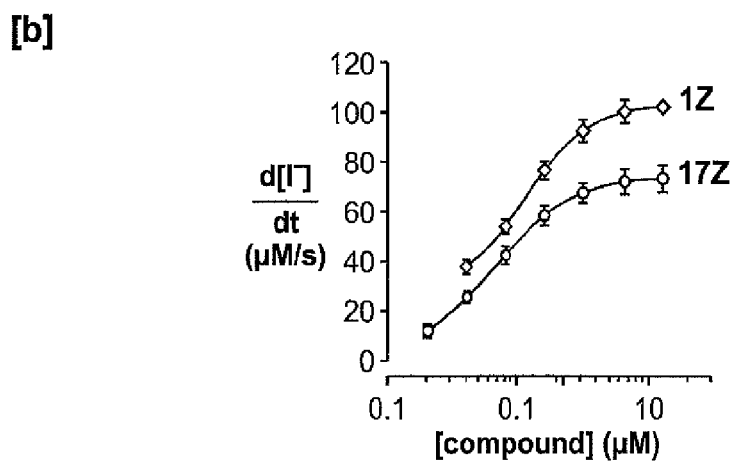
Figure 14:
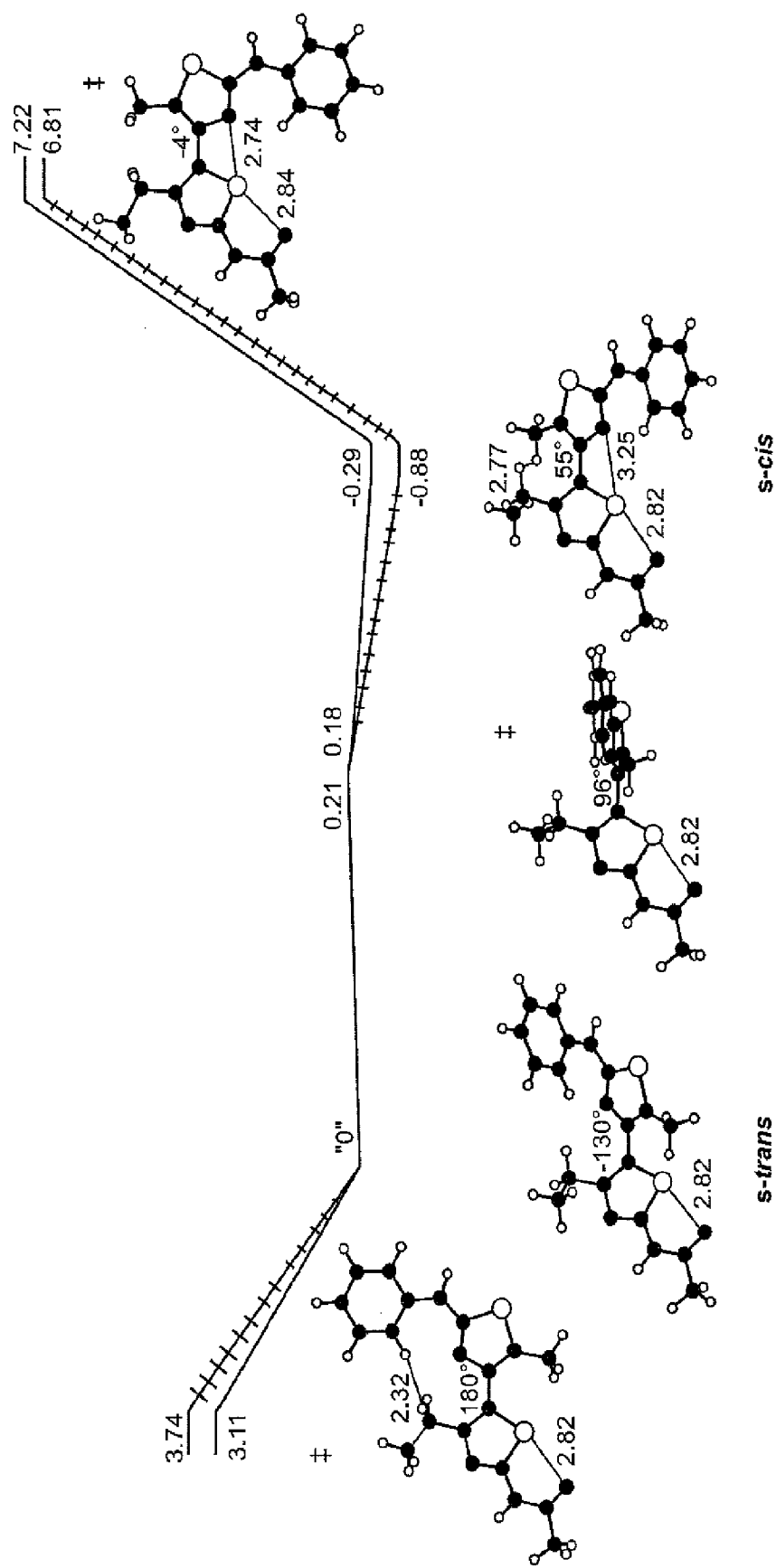
FIG. 14: Structures and associated energies for model of 17z. From left to right, the structures shown are: transition state structure for interconversion of enantiomeric s-trans conformations, one enantiomeric s-trans minimum, the transition state structure for interconversion of the s-trans and s-cis minima, one enantiomeric s-cis minimum, and the transition state structure for interconversion of enantiomeric s-cis conformations. Selected distances are shown in angstroms; dihedral angles shown are for the central C—C—C—C substructure; energies in kcal/mol relative to the s-trans minimum; gas-phase values in straight line, single point calculations in water in slashed line.

It was initially reasoned that increasing the steric bulk of the C(5)-substituent on the bithiazole core would effectively preclude access to the s-cis conformation. The C(4'), C(5) dimethyl analog 18z (FIG. 13a) would have been our preferred target for this study because the presumed hydrophobic methyl pocket requirements of 1z would have been unperturbed. That target preference was, however, offset by retrosynthetic considerations. Just as symmetrical 2z is an ideal precursor to 1z because the first thiazole-forming condensation can occur redundantly on either carbonyl, 4-chloroheptane-3,5-dione is an ideal precursor to 17z—the C(4)-$CH_2CH_3$/C(5)-$CH_3$ analog of 1z. A similar retro-synthetic analysis of the C(4)-CH$_3$/C(5)-CHs analog of 18z points to unsymmetrical 3-chlorohexane-2,4-dione as the starting material, but 18z encounters a vexing carbonyl selectivity issue in the first thiazole-forming condensation reaction. For this reason, bithiazole 17z was selected as an initial probe of the s-trans/s-cis conformation questions. Its synthesis—with the pivalamide and 5-chloro-2-methoxyaniline substructures fixed as in 1z—was accomplished in four steps as outlined in FIG. 13a. Corrector activity assay revealed that 17z, while not as active as 1z, is a better corrector than 7z, 10z and 13z, which supports the notion that the substituted bithiazole core is a critical contributor to the corrector activity of 1z (FIG. 13b). A conformational profile for 17z is shown in FIG. 14. Note that, despite the potential steric clash that was engineered into 17z, the s-cis conformer is again slightly lower in energy than the s-trans conformer. The s-cis minimum is now significantly distorted from planarity (twisted by ~55°), however, presumably representing a compromise between the favorable S . . . N interaction and steric repulsion between the ethyl and methyl groups. The s-trans minimum is also more twisted than it was for 1z. Planarization of either of these structures is associated with a significant energetic penalty (FIG. 14, far left and far right). Thus, if an approximately planar conformation, be it s-trans or s-cis, is required for binding, then the penalty associated with achieving such a conformation (3-7 kcal/mol) may account for the slightly reduced activity of 17z relative to 1z.

Figure 15:
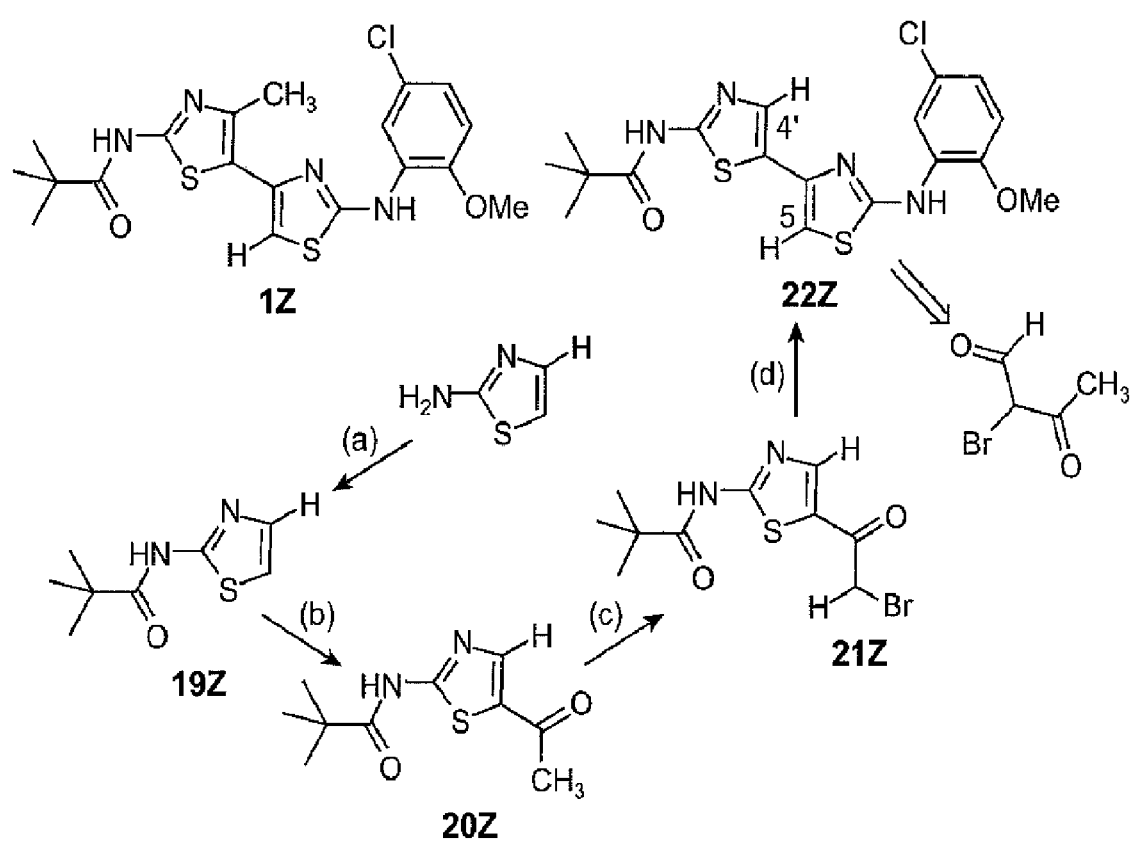
FIG. 15: Synthetic scheme of 22z.

Since 17z is not as active as 1z, bithiazole analog 22z, in which the C(4')—CH$_3$ of 1z is replaced with a C(4')—H to remove this impediment to achieving a planar conformation, was synthesized to determine if such an analog would improve corrector activity. Retrosynthetic analysis of 22z (FIG. 15) does not point back to a symmetric dicarbonyl starting material. Rather, the retrosynthetic precursor in this strategy would be 2-halo-3oxobutanal, which is known as its bromo analog. Indeed, 2-bromo-3-oxobutanal has been employed in the regioselective preparation of imidazole, oxazole, and thiazole heterocycles. However, as an alternate option, a quite different route to 5-substituted-2-aminothiazoles starting from commercial 2-aminothiazole has been reported by Katritzky (Katritzky, A. R.; Laurenzo, K. S.; Relyea, D. I. The preparation and fungicidal activity of a series of thiazolyl- and isothiazolyldiarylcarbinols. Can. J. Chem. 1988, 66, 16171624.). In that work, 2-aminothiazole is protected as its N,N-bis(trimethylsilyl) derivative and subsequently regioselective C(5)-lithiated. This latter route was selected for our work because this strategy could be readily used to introduce various groups at the C(5) position of the 2-aminothiazole ring. The C(4'), C(5)-unsubstituted analog 22z was obtained in five steps from 2-aminothiazole as outlined in FIG. 15.

Figure 16:
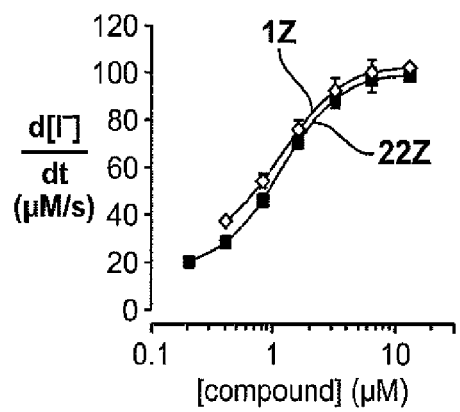
FIG. 16: (a) Concentration-activity profiles of 1z and 22z. (b) Structures and associated energies for model of 22z. From left to right, the structures shown are: s-trans minimum, the transition state structure for interconversion of the s-trans and s-cis minima and the s-cis minimum. Selected distances are shown in angstroms; dihedral angles shown are for the central C—C—C—C substructure; energies in kcal/mol relative to the s-trans minimum; gas-phase values in straight line, single point calculations in water in slashed line.
Figure 16:
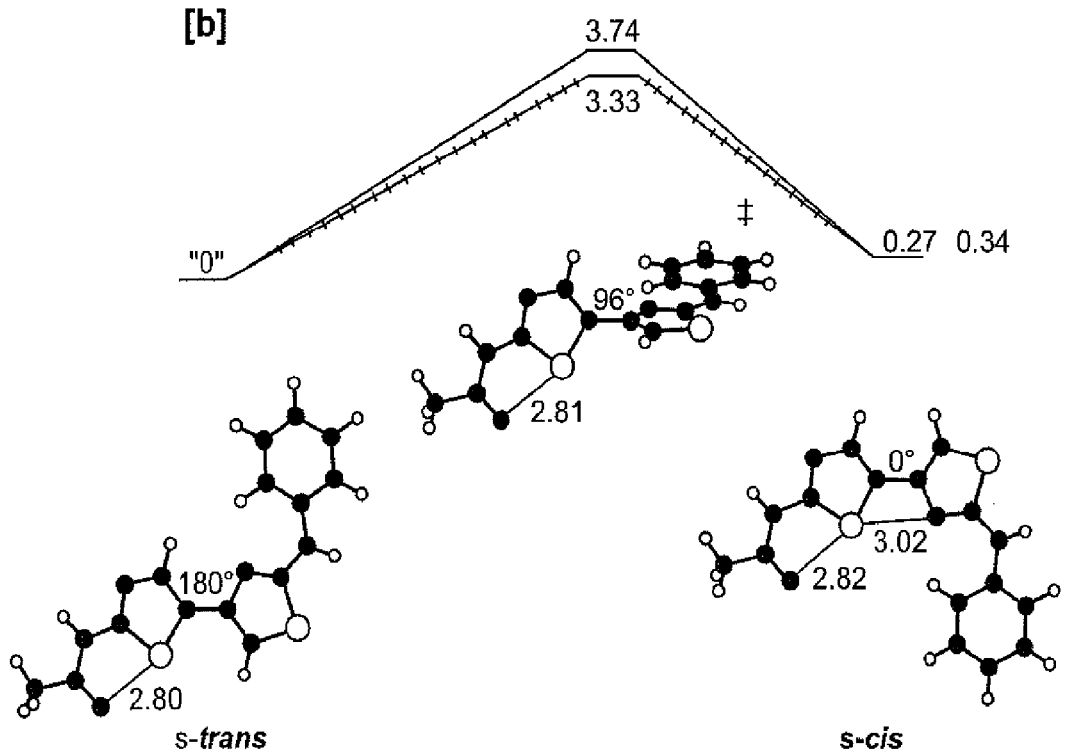

FIG. 16a shows that 22z has a comparable IC$_{50}$ to 1z. The s-trans and s-cis minima for bithiazole 22z are both planar and extremely close in energy (FIG. 16b), providing circumstantial evidence that an approximately planar conformation of 22z can be in an active conformation.

Figure 17:
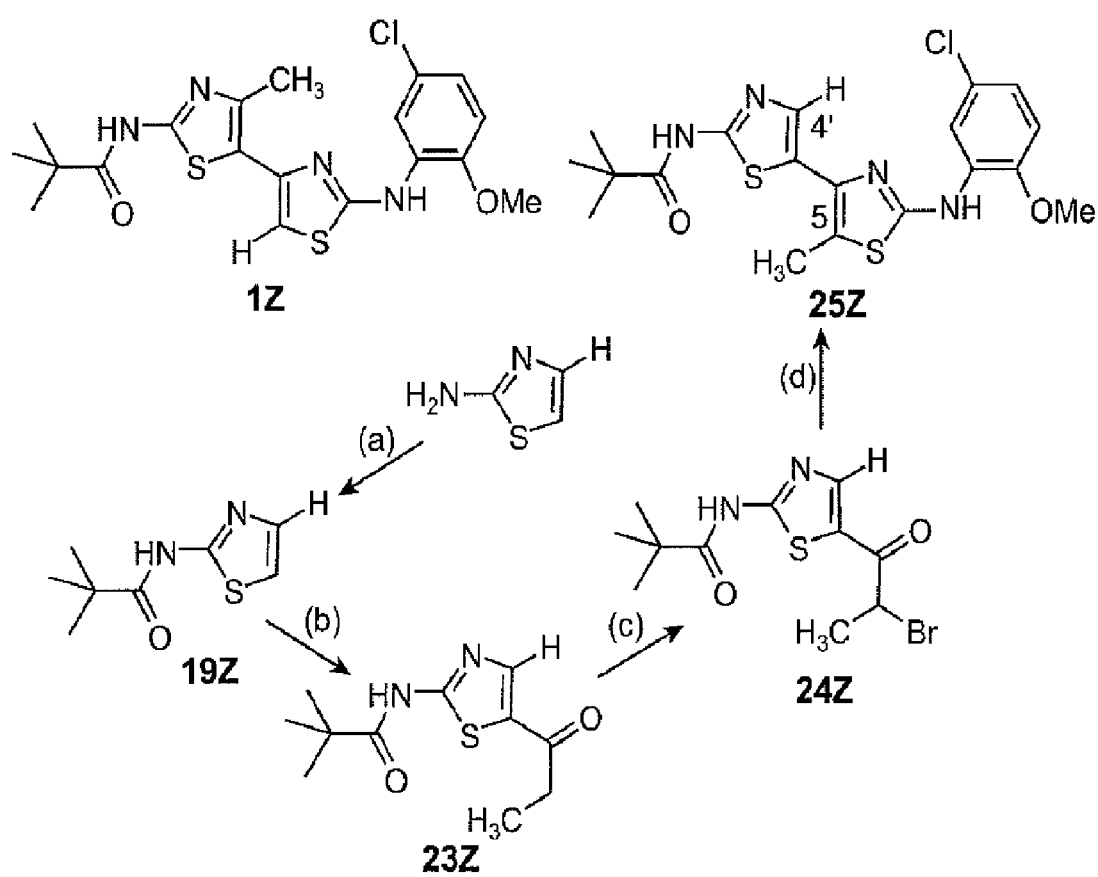
FIG. 17: Synthetic scheme of 25z.

Following from these insights with corrector 22z, bithiazole methyl placement with analog 25z was investigated (FIG. 17). This compound is the C(4')/C(5) methyl-hydrogen interchange analog of 1z. By utilizing a modification of Katritzky's 2aminothiazole protection/C(5)-lithiation strategy employed in FIG. 15 but replacing acetaldehyde with propionaldehyde, the methyl-hydrogen transposed bithiazole 25z was obtained in five steps from 2-aminothiazole.

Figure 18:
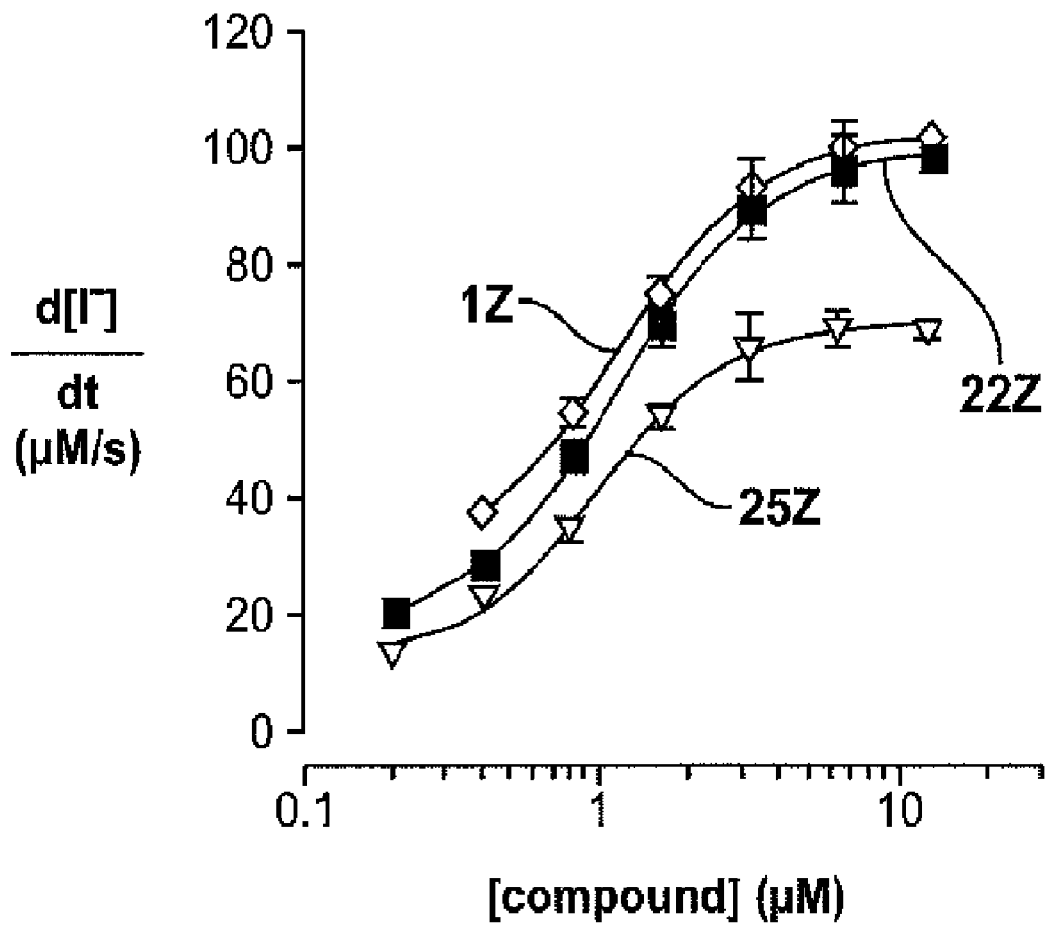
FIG. 18: Concentration-activity profiles of 1z. 22z, and 25z.

FIG. 18 shows the corrector activity data of 25z compared with 1z and 22z. These data support the notion that methyl placement is a factor. Indeed, that 1z is a more effective corrector than 25z suggests that a C(4')—CHs better addresses a hydrophobic binding pocket than does a C(5)-CHs placement.

Figure 19:
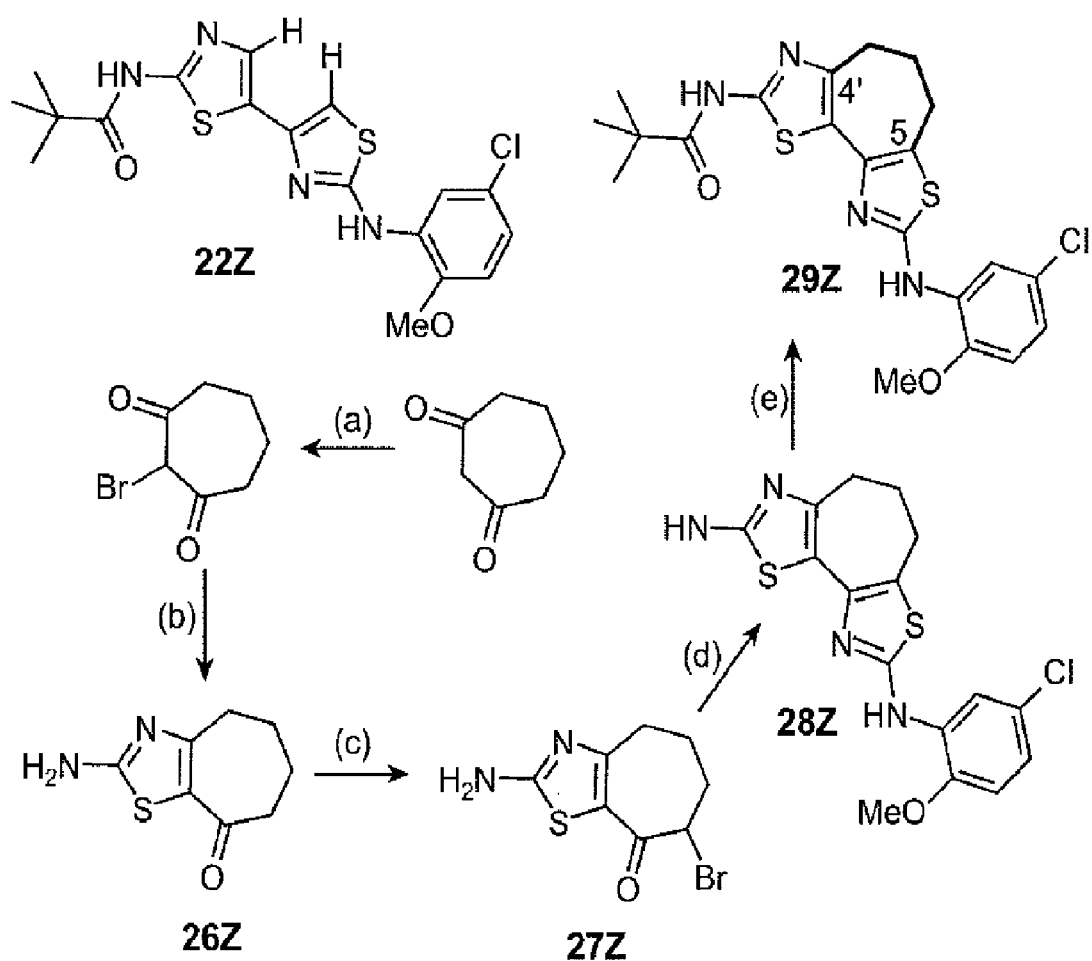
FIG. 19: Synthetic scheme of 29z.
Figure 20:
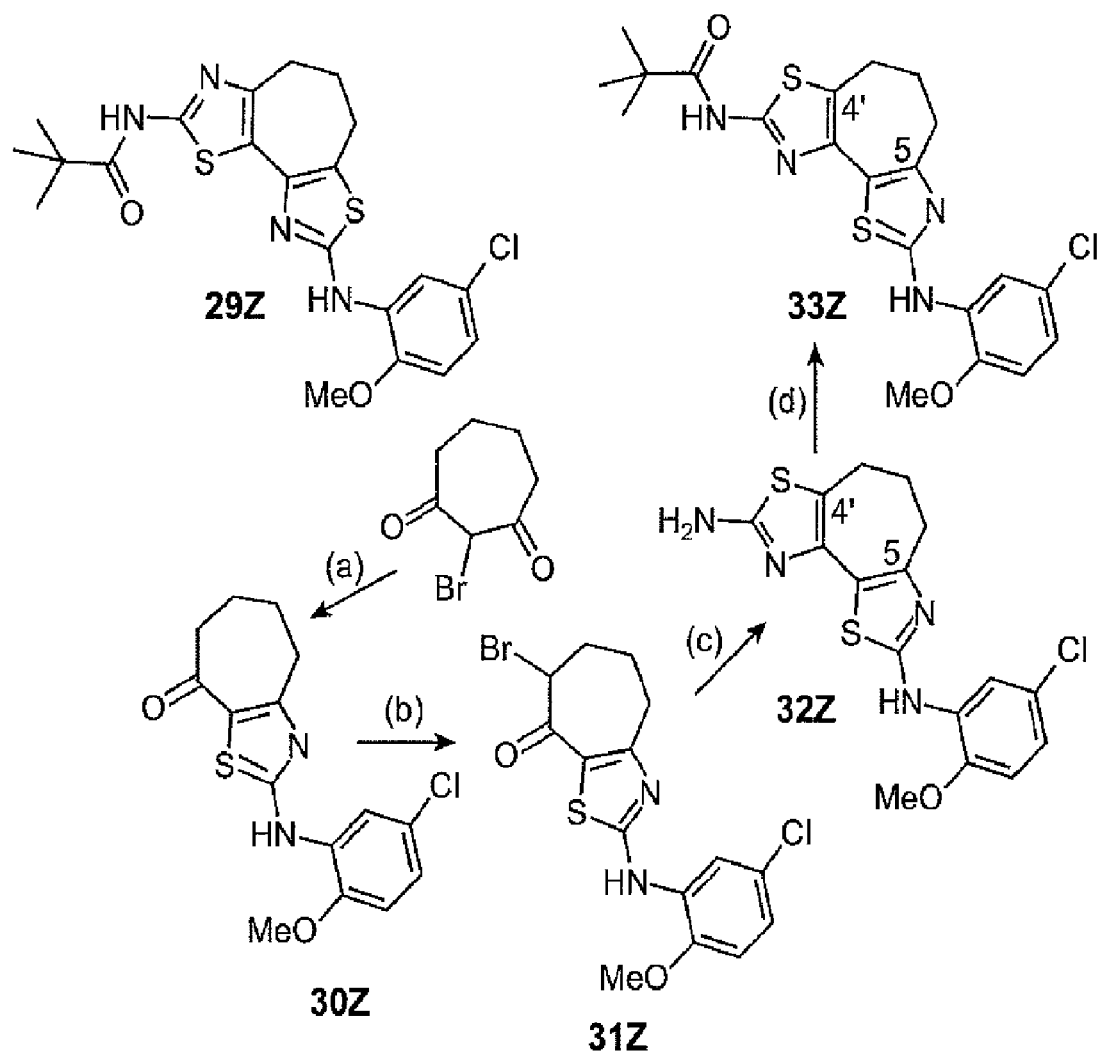
FIG. 20: Synthetic scheme of 33z.

The structure-activity relationships above support the notion that a planar bithiazole conformation is required for bithiazole ΔF508-SFTR corrector activity. While both 22z and 1z accommodate that requirement, neither constrains the bithiazole moiety to be planar nor do they predispose it in either the s-cis or s-trans conformation. To address these issues, the synthesis of conformationally locked analogs was undertaken, beginning with a compound constrained to be s-cis. Of the structural options considered, cycloheptathiazolothiazole 29z appeared to be the best s-cis alternative because (a) the corresponding cyclohexa-analog would be susceptible to aromatization (an event that would reduce solubility) and (b) precursors to the cycloocta-analog would be more difficult to prepare. Our route to 29z starts with cycloheptane-1,3-dione and is outlined in FIG. 19. Cycloheptathiazolothiazole 33z, the N↔S transposed isomer of 29z, was also prepared. The route to 33z is related to that used for the synthesis of 29z except that the 2-(5-chloro-2-methoxyanilino)thiazole heterocycle is now introduced first followed then by the 2-(N-pivalamido)thiazole heterocycle (FIG. 20) by analogy with the strategy outlined in FIG. 9.

Figure 21:
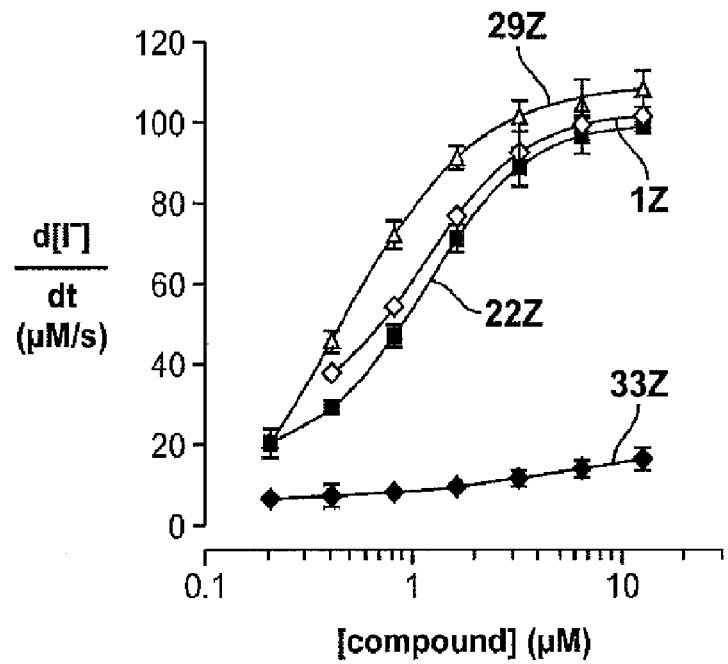
FIG. 21: (a) Concentration-activity profiles of 1z, 22z, 29z, and 33z. (b) Structures and associated energies for model of 29z.
Figure 21:
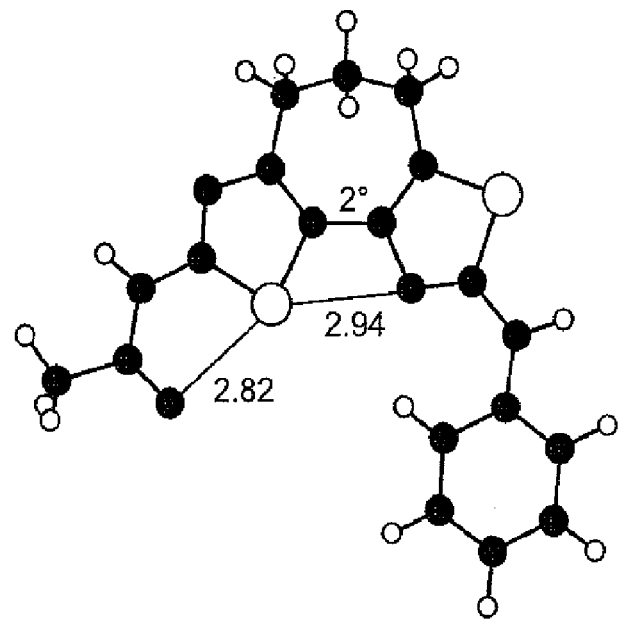

The ΔF508-CFTR corrector activity data for cycloheptathiazolothiazoles 29z and 33z are shown relative to 22z and 1z in FIG. 21a. Given that 29z is an effective corrector and cannot adopt an s-trans conformation, we conclude that an s-cis conformation is required for bithiazole activity. Moreover, the fact that bithiazole 17z is a relatively ineffective ΔF508CFTR corrector supports the contention that an approximately planar s-cis conformation is ideal for maximizing activity. Our calculations indicate that the preferred conformation for 29z involves essentially coplanar thiazole rings (FIG. 21b), although twisting from planarity by up to 25° is associated with a penalty of just over 1 kcal/mol.

Correctors 29z, 22z and 1z can readily adopt a conformation with coplanar thiazole rings and, consequently, each of these has ΔF508-CFTR corrector activity. The fact that s-cis-locked corrector 29z is the most active of these compounds is likely a result of removal of the entropy penalty expected upon binding by the conformationally flexible 1z and 22z by conformational preorganization in 29z.

Bithiazole 33z, the N↔S transposed isomer of 29z, is substantially inactive even though it can place the pivalamide and 5-chloro-2-methoxyaniline substructures in similar orientations relative to the most active compound, corrector 29z. These data are consistent with proper placement of the four bithiazole heteroatoms being an important structural determinant in bithiazole ΔF508-CFTR corrector activity.

Figure 22:
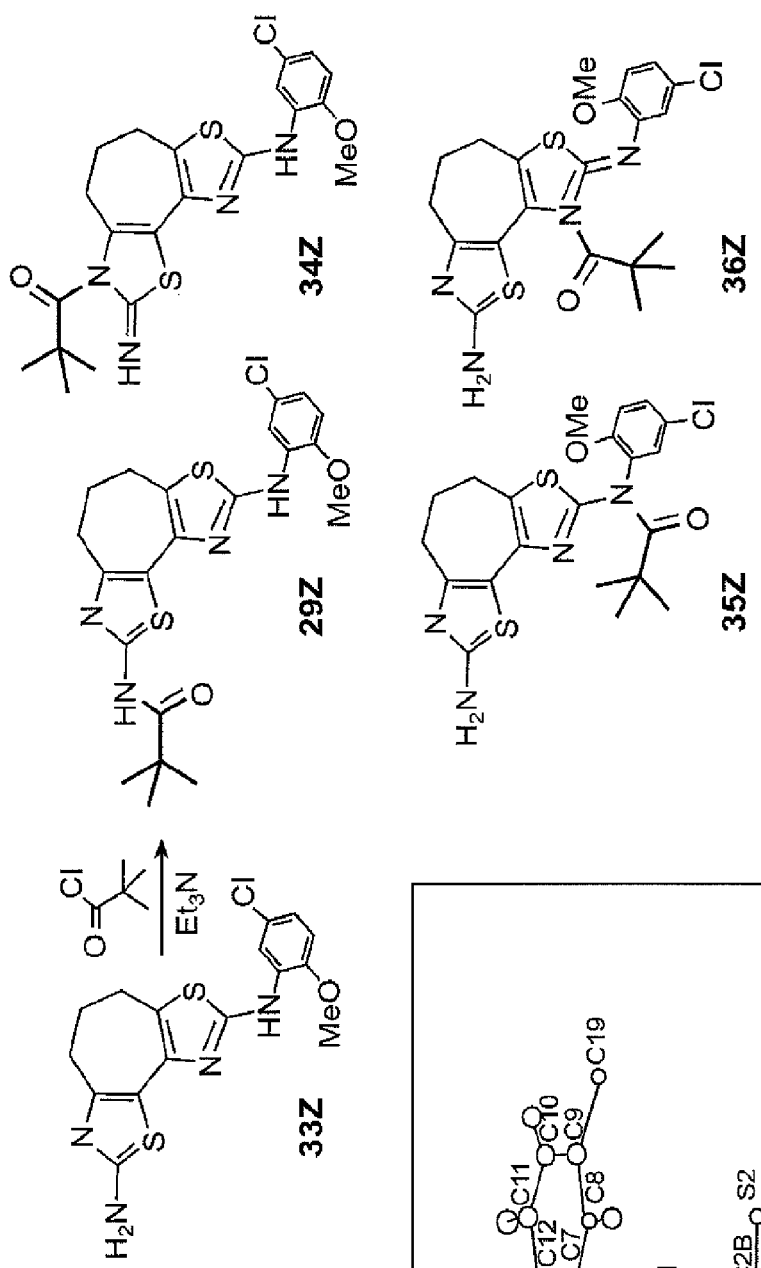
FIG. 22: Chemoselective N-acylation of cycloheptathiazolothiazole heterocycle.
Figure 22:
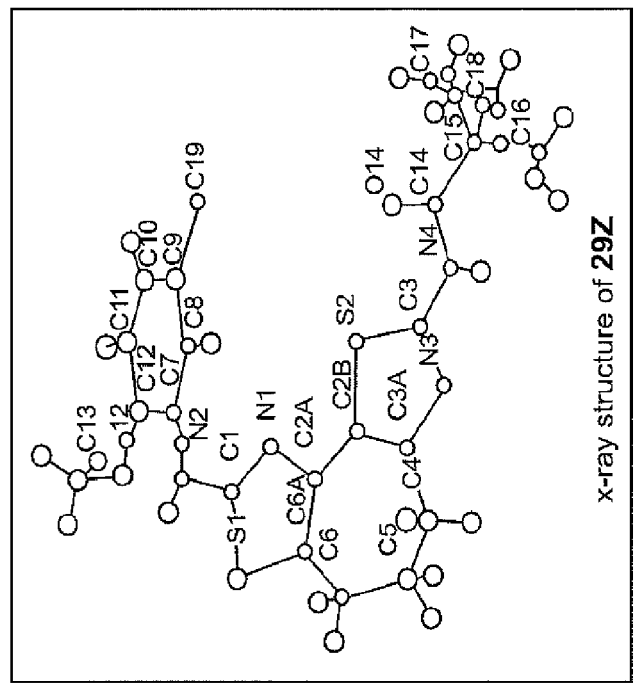

The final question regards the structure of the most potent activator cycloheptathiazolothiazole 29z; specifically, did the N-acylation with pivaloyl chloride occur at the 2-amino position to give 29z or did this N-acylation occur to give one of the potential products 34z-36z (see FIG. 22)? Spectroscopic analysis of this reaction product proved difficult to unambiguously establish which product had been formed. Therefore, X-ray quality crystals were obtained and crystallographic analysis established that the sole product of this reaction was, indeed, 29z.

In conclusion, a systematic analysis of lead bithiazole core ΔF508-CFTR corrector 1z has been reported. Loss of corrector activity with analogs 7z, 10z, and 13z is consistent with the bithiazole substructure playing a central role in the activity of 1z. Conformational analysis of the thiazole-tethering C(4)-C(5') bond suggested that two distinctly different conformations—one where the C(4')—CHs substituent is s-trans to the C(5)-H and another where the C(4')—CHs substituent is s-cis to the C(5)-H—are available to the 4'-methyl-4,5' bithiazole moiety of 1z. Activity data for bithiazole analogs 17z, 22z and 25z, as well as the s cis-locked analog 29z and its transposed counterpart 33z indicate that an approximately planar s-cis bithiazole conformation, with proper placement of the four bithiazole heteroatoms, is likely the active presentation of 1z.

Experimental:

ΔF508-CFTR Corrector Activity Assay.

FRT epithelial cells stably coexpressing human 6 ΔF508-CFTR and the high-sensitivity halide-sensing fluorescent protein YFP7H148Q/I152L were used as described previously. Cells were grown at 37° C. (95% air/85% CO2) for 24 h and then incubated for 16-20 h with 50 μL of medium containing the test compound. At the time of the assay, cells were washed with PBS and then incubated with 10 PBS containing forskolin (20 μM) and genistein (50 μM) for 20 min. Measurements were carried out using FLUOstar fluorescence plate readers (Optima; BMG LABTECH Gmbh), each equipped with 500±10 nm excitation and 535±15 nm emission filters P (Chroma Technology Corp.). Each well was assayed individually for I⁻ influx by recording fluorescence continuously (200 ms per point) for 2 s (baseline) and then for 12 s after rapid (<1 second) addition of 165 μL PBS in which 137 mM Cl⁻ was replaced by I⁻. I⁻ influx rate was computed by fitting the final 11.5 s of the data to an exponential for extrapolation of initial slope and normalizing for background-subtracted initial fluorescence. All experiments contained negative control (DMSO vehicle) and positive control [N-(2-(5-chloro-2-methoxyphenylamino)-4'-methyl-4,5'-bithiazol-2'-yl)benzamide].

1-{2-[(5-Chloro-2-methoxyphenyl)amino]-4-methyl-1,3-thiazol-5-yl}ethanone (5z)

A mixture containing 2z (0.67 g, 5 mmol) and 4 (1.08 g, 5 mmol) in absolute ethanol (25 mL) was refluxed for 24 h. Upon cooling the reaction mixture in an ice bath, the product precipitated and was collected by filtration and washed with cold ethanol to afford 5z as a yellow-brown solid (0.82 g, 55%). $^1$H NMR (600 MHz, DMSO-d6): δ 10.17 (s, 1H), 8.41 (br 26 s, 1H), 7.00-7.03 (m, 2H), 3.82 (s, 3H), 2.50 (s, 3H), 2.37 (s, 3H). $^{13}$C NMR (150 MHz, DMSO-d6): δ 189.5, 165.1, 155.9, 147.4, 130.2, 124.1, 123.3, 122.4, 118.9, 112.4, 56.1, 29.8, 18.5. MS m/z (ESI) 296.99 (M+H)⁺.

2-Bromo-1-{2-[(5-chloro-2-methoxyphenyl)amino]-4-methyl-1,3-thiazol-5-yl}ethanone (6z)

To a solution of 5z (0.15 g, 0.5 mmol) in HBr/HOAc (33% wt HBr in HOAc; 2.5 mL) was added pyridinium tribromide (0.18 g, 0.55 mmol). The reaction mixture was stirred at room temperature for 24 h and poured onto ice-water. The precipitated product was collected by filtration, washed with cold water, and dried to afford 6z (0.19 g, 99%). Rf=0.714 in Hexane:EtOAc:1:1. $^1$H NMR (600 MHz, DMSO-d6): δ 8.38 (d, J=2.4 Hz, 1H), 7.07-7.12 (m, 2H), 4.58 (s, 2H), 3.86 (s, 3H), 2.57 (s, 3H). $^{13}$C NMR (150 MHz, DMSO-d6): δ 183.1, 166.1, 158.1, 147.8, 129.8, 124.1, 123.1, 119.6, 119.4, 112.7, 56.2, 36.0, 18.7. MS m/z (ESI) 376.92 (M+H)⁺.

N-(4-(2-(5-Chloro-2-methoxyphenylamineo)-4-methylthiazole-5-yl)thiazole-2-yl)pivalamide (7z)

An absolute ethanol (8 mL) solution of 6z (0.19 g, 0.5 mmol) and thiourea (0.04 g, 0.5 mmol) was refluxed for 24 h.

Upon completion of reaction, the solvent was removed by evaporation under reduced pressure and the residue was washed with chloroform and dried to give a pale grey solid (0.15 g, 85%) which was used in the next step without purification.

Pivaloyl chloride (0.10 g, 0.85 mmol) was added dropwise to a CH₃CN/THF (1:1::vol:vol; 20 mL) solution of the crude material from above [N²¹-(5-chloro-2-methoxyphenyl)-4'-methyl-4,5'-bithiazole-2,2'-diamine; 0.15 g, 0.43 mmol] and triethylamine (0.09 g, 0.86 mmol) at room temperature. To effect starting material dissolution, the reaction mixture was warmed to reflux for 20 h. The reaction mixture was concentrated under vacuum and the resulting residue was washed with chloroform and filtered. The filtrate was washed with water and dried (Na₂SO₄). Filtration followed by solvent removal under vacuum produced a residue that was subjected to preparative HPLC purification (UV detector: 224 nm; Eluents: H₂O (A), CH₃CN (B); Gradients: 0-1 min: 90% A, 1-13 min: 90%-40% A, 13-18 min: 40%-0% A, 18-21 min: 0% A, 21-21.5 min: 0%-90% A, 21.5-25 min: 90% A). The product 7z was obtained as white needles (0.06 g, 34%). $^1$H NMR (300 MHz, CDCl₃): δ 9.00 (s, 1H), 7.41 (d, J=2.1 Hz, 1H), 7.23-7.27 (m, 2H), 6.93 (s, 1H), 6.90 (s, 1H), 3.89 (s, 3H), 2.55 (s, 3H), 1.34 (s, 9H). $^{13}$C NMR (75 MHz, CDCl₃): δ 176.6, 167.5, 158.4, 151.7, 139.4, 134.4, 128.5, 127.8, 125.8, 123.6, 113.8, 113.3, 109.7, 56.5, 39.5, 27.4, 14.0. HRMS m/z (ESI) calcd. for C₁₉H₂₁ClN₄O₂S₂ (M+H)⁺ 437.0867. Found 437.0867.

N-(3-Acetylphenyl)pivalamide (8z)

To a stirred solution of 3-aminoacetophenone (1.0 g, 7.4 mmol) in chloroform cooled to 0° C. was added triethylamine dropwise (1.44 g, 14.2 mmol). The mixture was stirred for 15 min at this temperature and then pivaloyl chloride (0.83 g, 7.4 mmol) was added dropwise and the mixture was stirred overnight. Water was added and the aqueous layer was extracted with DCM. The collected organic extracts were washed with sat. aq. NaHCO₃ and brine, dried over anhydrous MgSO₄, and filtered. The solvent was evaporated under reduced pressure to afford 8z as a white solid (1.29 g, 80%). Mp 130-133° C. $^1$H NMR (600 MHz, CDCl₃): δ 8.07 (t, J=1.8 Hz, 1H), 7.90-7.88 (m, 1H), 7.76 (br s, 1H), 7.65-7.63 (m, 1H), 7.37 (t, J=1.8 Hz 1H), 2.57 (s, 3H), 1.31 (s, 9H). $^{13}$C NMR (150 MHz, CDCl₃): δ 198.2, 177.2, 138.8, 137.7, 129.3, 124.9, 124.1, 119.7, 39.8, 27.6, 26.8.

N-(3-(2-Bromoacetyl)phenyl)pivalamide (9z)

To a stirred solution of N-(3acetylphenyl)pivalamide 8z (0.30 g, 1.37 mmol) in 33% HBr in HOAc (5 mL) was added pyridinium tribromide (0.48 g, 1.51 mmol) and the mixture was stirred at room temperature for 24 h then poured into ice-cold water. The organic layer was extracted with DCM, washed with sat. aq. NaHCO₃ and brine, dried over anhydrous MgSO₄, and filtered. Evaporation of the solvent afforded 9z (0.32 g, 78%) which was used in the next step without further purification. $^1$H NMR (600 MHz, CDCl₃): δ 8.08 (t, J=1.8 Hz, 1H), 7.94 (br s, 1H), 7.82 (dt, J=8.4, 1.2 Hz, 1H), 7.60 (dd, J=7.2 Hz, 1.2 Hz, 1H), 7.32 (t, J=7.8 Hz, 1H), 4.30 (s, 2H), 1.27 (s, 9H). $^{13}$C NMR (150 MHz, CDCl₃): δ 191.2, 177.3, 139.0, 134.4, 129.3, 125.8, 124.4, 120.4, 39.7, 31.4, 27.5. MS m/z (ESI) 298.06 [M+H]⁺, 300.02 [(M+2)+H]⁺.

N-(3-(2-(5-Chloro-2-methoxyphenylamino)thiazol-4-yl)phenyl)pivalamide (10z)

A mixture of 9z (0.32 g, 1.06 mmol) and 4z (0.23 g, 1.06 mmol) in ethanol was refluxed for 48 h. The solvent was evaporated and the residue was purified by preparative HPLC to afford 10Z as a white-grey solid (0.32 g, 73%). Mp 137-138° C. $^1$H NMR (300 MHz, CDCl$_3$): δ 7.99 (s, 1H), 7.82 (m, 1H), 7.67 (s, 1H), 7.48 (d, J=2.4 Hz, 1H), 7.42 (m, 1H), 7.25 (m, 1H), 6.93 (d, J=8.7 Hz, 1H), 6.73 (s, 1H), 3.89 (s, 3H), 1.34 (s, 9H). $^{13}$C NMR (75 MHz, CDCl$_3$): δ 177.4, 169.6, 151.2, 142.8, 139.3, 129.2, 128.2 127.7, 126.0, 123.4, 2×121.3, 117.7, 113.2, 100.2, 56.3, 39.9, 27.6. HRMS m/z (ESI) calcd. for C$_{21}$H$_{22}$ClN$_3$O$_2$S (M+H)$^+$ 416.1194. Found 416.1193.

2-Bromo-1-(3-nitrophenyl)propan-1-one (11z)

To a stirred solution of 1-(3-nitrophenyl)propan-1-one (1.41 g, 7.90 mmol) in acetic acid (20 mL) was added bromine dropwise (1.27 g, 7.93 mmol) and the mixture was stirred at room temperature for 24 h. The mixture was poured into ice-cold water and the organic layer was extracted with DCM. The organic extract was washed with sat. aq. NaHCO$_3$ and brine, dried over anhydrous MgSO$_4$, and filtered. Evaporation of the solvent under reduced pressure afforded 11z as a white solid which was used in the next step without further purification (1.78 g, 87%). $^1$H NMR matches literature data.

N-(5-Chloro-2-methoxyphenyl)-5-methyl-4-(3-nitrophenyl)thiazol-2-amine (12z)

A mixture of 11z (0.50 g, 1.94 mmol) and 4z (0.42 g, 1.94 mmol) in ethanol was refluxed for 24 h. The mixture was cooled to room temperature and the precipitate was collected by filtration to afford 12z as a yellow solid (0.57 g, 78%). Mp decomposition at 185° C. $^1$H NMR (300 MHz, DMSO-d6): δ 8.64 (m, 1H), 8.50 (m, 1H), 8.15 (m, 2H), 7.73 (m, 1H), 6.96 (m, 2H), 4.84 (br s, 1H), 3.87 (s, 3H), 2.48 (s, 3H). $^{13}$C NMR (150 MHz, DMSO-d6): δ 159.4, 148.0, 146.4, 141.9, 136.4, 131.2, 124.3, 120.5, 133.6 130.0, 122.1, 121.6, 120.4, 116.9, 111.8, 56.0, 11.9. MS m/z (ESI) 376.06 [M+H]$^+$.

N-(3-(2-(5-Chloro-2-methoxyphenylamino)-5-methylthiazol-4-yl)phenyl)-pivalamide (13z)

A mixture of 12z (0.25 g, 0.66 mmol) and SnCl$_2$.2H$_2$O (1.35 g, 6.0 mmol) in methanol was refluxed for 48 h. Evaporation of the solvent under reduced pressure afforded 4-(3aminophenyl)-N-(5-chloro-2-methoxyphenyl)-5-methylthiazol-2-amine as a solid which was dissolved in chloroform and cooled in an ice bath to 0° C. Triethylamine (93 μL, 0.66 mmol) was added and the mixture was stirred for 15 min at the same temperature. Pivaloyl chloride (0.08 g, 0.66 mmol) was then added dropwise at 0° C. and the mixture was stirred overnight at which point the mixture was poured onto ice-cold water and the aqueous layer was extracted with DCM. The collected organic extract was washed with sat. aq. NaHCO$_3$ and brine, dried over anhydrous MgSO$_4$, and filtered. Evaporation of the solvent under reduced pressure afforded 13z as a yellowish white solid (0.21 g, 75%). Mp decomposition at 195° C. $^1$H NMR (300 MHz, CDCl$_3$): δ 7.83 (s, 1H), 7.76 (s, 1H), 7.45 (m, 1H), 7.38 (d, J=2.40 Hz, 1H), 7.33 (s, 1H), 7.27 (m, 1H), 6.93 (d, J=9.0 Hz, 1H), 3.89 (s, 3H), 2.42 (s, 3H), 1.33 (s, 9H). $^{13}$C NMR (150 MHz, CDCl$_3$): δ 177.4, 168.4, 151.5, 139.1, 129.9, 127.8, 125.9, 124.3, 123.6, 121.3, 120.3, 118.5, 114.5, 113.3, 111.4, 111.0, 56.4, 39.9, 27.7, 12.5. HRMS m/z (ESI) calcd. for C$_{22}$H$_{24}$ClN$_3$O$_2$S (M+H)$^+$ 430.1351. Found 430.1345.

1-(2-Amino-4-ethylthiazol-5-yl)propan-1-one (14z)

An absolute ethanol solution of bromine (453 μL, 8.82 mmol) was added dropwise at room temperature to an abs. ethanol solution of 3,5-heptanedione (1.13 g, 8.82 mmol). The resulting reaction mixture was refluxed overnight at which point the ethanol was evaporated in vacuo and the residue was triturated with a small quantity of DCM. The DCM was evaporated to dryness under reduced pressure and the residue was treated with cold acetone. The resulting brown solid was collected by filtration and rinsed with cold acetone to afford 14z as a white powder (1.3 g, 80%). Mp decomposition at 133° C. $^1$H NMR matches literature data.

1-(2-Amino-4-ethylthiazol-5-yl)-2-bromopropan-1-one (15z)

Compound 14z (0.53 g, 1.99 mmol; HBr form) in acetic acid (2 mL) was treated dropwise with bromine (103 μL, 1.99 mmol), and the reaction mixture was stirred at room temperature for 3 h. The white precipitate was collected by filtration and washed with cold acetone to yield 15z as a white powder (0.59 g, 86%). Mp decomposition at 122° C. $^1$H NMR (600 MHz, DMSO-d6): δ 4.99 (q, J=6 Hz, 1H), 2.88 (q, J=6 Hz, 2H), 1.69 (d, J=6 Hz, 3H), 1.16 (t, J=6 Hz, 3H). $^{13}$C NMR (150 MHz, DMSO-d6): δ 185.5, 170.7, 115.5×2, 47.6, 47.5, 24.0, 20.8, 13.5. MS m/z (ESI) 263.00 [M+H]$^+$, 264.96 [(M+2)+H]$^+$.

4-(2-Amino-4-ethylthiazol-5-yl)-N-(5-chloro-2-methoxyphenyl)-5-methylthiazol-2-amine (16z)

Compound 15z (0.56 g, 1.64 mmol) was dissolved in absolute ethanol (15 mL) and 4z (0.36 g, 1.64 mmol) was added at room temperature. The resulting suspension was stirred at reflux for 2 h. After removal of ethanol in vacuo, the solid was collected by filtration and washed with cold ethanol to yield 16z as a yellow powder (0.75 g, 99%). Mp decomposition at 133° C. $^1$H NMR (600 MHz, CDCl$_3$): δ 8.96 (br s, 2H), 7.79 (d, J=2.4 Hz, 1H), 7.01 (dd, J=8.4 Hz, 2.4 Hz, 1H), 6.82 (d, J=8.4 Hz, 1H), 3.87 (s, 3H), 2.66 (q, J=7.6 Hz, 2H), 2.29 (s, 3H), 1.33 (t, J=7.6 Hz, 3H). $^{13}$C NMR (150 MHz, DMSO-d6): δ 169.6, 162.5, 148.0, 140.2, 128.8, 126.1, 124.5, 123.2, 119.1, 112.1, 56.5, 21.2, 18.6, 13.1. MS m/z (ESI) 380.97 [M+H].

N-(5-(2-(5-Chloro-2-methoxyphenylamino)-5-methylthiazol-4-yl)-4-ethylthiazol-2-yl)pivalamide (17z)

To a suspension of 16z (0.50 g, 1.1 mmol) in DCM (55 mL) was added TEA (395 μL, 2.84 mmol). Pivaloyl chloride (174 μL, 1.42 mmol) was then added to the suspension in one portion and the reaction mixture was stirred at room temperature for 10 min at which time TLC indicated reaction completion. The reaction mixture was washed with cold water and extracted with DCM (2×). The organic layer was dried over anhydrous sodium sulfate and filtered and DCM was removed in vacuo. The resulting solid was purified by silica gel column chromatography (hexane:ethyl acetate=4:1 eluent) to yield 17z as a light orange powder (0.34 g, 66%). Mp decomposition at 192° C. $^1$H NMR (400 MHz, CDCl$_3$): δ 7.72 (d, J=2.8 Hz, 1H), 7.13 (dd, J=8.8 Hz, 2.8 Hz, 1H), 6.88 (d, J=8.8 Hz, 1H), 3.90 (s, 3H), 2.79 (q, J=7.6 Hz, 2H), 2.30 (s, 3H), 1.39 (s, 9H), 1.34 (t, J=7.6 Hz, 3H). $^{13}$C NMR (100 MHz, CDCl$_3$): δ 178.6, 164.6, 164.2, 163.8, 162.2, 149.1, 144.9, 128.9, 125.5, 120.5, 113.8, 112.3, 104.9, 56.3, 40.1, 26.7, 21.4, 13.5, 12.2. HRMS m/z (ESI) calcd. for C$_{21}$H$_{25}$ClN$_4$O$_2$S$_2$ (M+H)$^+$ 465.1180. Found 465.1181.

N-(5-Acetylthiazol-2-yl)pivalamide (20z)

Freshly distilled diisopropylamine (5.98 mL, 42.70 mmol) was dissolved in dry THF (30 mL) and cooled to −78° C.

under nitrogen. This solution was treated dropwise with 2.5 M n-BuLi in hexane (17.1 mL, 42.70 mmol) and stirred for 30 min. A solution of 19z (3.58 g, 19.41 mmol) in anhydrous THF (20 mL) was then added dropwise to this LDA solution and stirred for 30 min at −78° C. at which time acetaldehyde (3.59 mL, 64.05 mmol) was added dropwise. The resulting mixture was stirred overnight as it warmed to ambient temperature. The reaction was quenched by dropwise addition of water, diluted with DCM (3× the THF volume), washed with water and dried over anhydrous sodium sulfate and filtered. After removal of solvents, the resulting crude material was used in the next step without purification.

This crude material (0.80 g, 3.50 mmol) was dissolved in CHCl3 (35 mL), manganese dioxide (9 g, 104 mmol) was added, and the resulting mixture was stirred at room temperature overnight. Filtration of the reaction mixture through a pad of celite and chloroform removal gave crude product which was purified by silica gel column chromatography (hexane:ethyl acetate=4:1 eluent) to yield 20z as a white powder (0.42 g, 53%). $^1$H NMR (300 MHz, CDCl$_3$): δ 10.0 (br s, 1H), 7.98 (s, 1H), 2.48 (s, 3H), 1.29 (s, 9H).

N-(5-(2-Bromoacetyl)thiazol-2-yl)pivalamide (21z)

Compound 20z (0.26 g, 1.15 mmol) was dissolved in 33% HBr in HOAc (100 mL), pyridinium tribromide (0.37 g, 1.15 mmol) was added, and the reaction was stirred at room temperature overnight. The reaction mixture was poured onto ice water and the solid was collected by filtration to yield 21z which was in the next step without purification (0.34 g, 97%). $^1$H NMR (400 MHz, CDCl$_3$): δ 8.12 (s, 1H), 4.27 (s, 2H), 1.36 (s, 9H).

N-(2-(5-Chloro-2-methoxyphenylamino)-4,5'-bithiazol-2'-yl)pivalamide (22z)

A suspension of 21z (0.73 g, 2.3 mmol) and N-(5-chloro-2-methoxyphenyl)thiourea (0.73 g, 2.53 mmol) in EtOH (25 mL) was refluxed for 30 min. Upon cooling, the product was collected by filtration and washed with cold ethanol to yield 22z as a pale yellow solid (0.40 g, 84%). Mp decomposition at 216° C. $^1$H NMR (600 MHz, DMSO-d6): δ 11.86 (br s, 1H) 9.93 (br s, 1H), 8.64 (d, J=2.4 Hz, 1H), 7.83 (s, 1H), 7.18 (s, 1H), 7.02 (d, J=8.4 Hz, 1H), 6.98 (dd, J=8.4 Hz, 2.4 Hz, 1H), 3.86 (s, 3H), 1.25 (s, 9H). $^{13}$C NMR (150 MHz, DMSO-d6): δ 176.7, 162.1, 158.9, 146.6, 140.2, 136.4, 130.5, 124.7, 124.2, 121.3, 117.3, 112.1, 91.0, 56.1, 38.8, 26.6. HRMS m/z (ESI) calcd. for C18H19ClN4O2S2 (M+H)$^+$ 423.0711. Found 423.0713.

N-(5-Propionylthiazol-2-yl)pivalamide (23z)

Following the protocol outlined for 20z gave 23z as an off white powder (0.78 g, 52%).

Mp decomposition at 126° C. $^1$H NMR (400 MHz, CDCl$_3$), δ 9.23 (br s, 1H), 8.03 (s, 1H), 2.88 (q, J=8 Hz, 2H), 1.34 (s, 9H), 1.23 (t, J=8 Hz, 3H). MS (ESI) m/z 241.07 [M+1]$^+$.

N-(5-(2-Bromopropanoyl)thiazol-2-yl)pivalamide (24z)

Following the protocol outlined for 21z gave 24z (0.73 g, 71%) as an off white powder. Mp decomposition at 192° C. $^1$H NMR (400 MHz, CDCl$_3$): δ 8.25 (s, 1H), 5.02 (q, J=6.8 Hz, 1H), 1.87 (d, J=6.8 Hz, 3H), 1.35 (s, 9H). MS m/z (ESI) 319.04 [M+H]$^+$, 321.00 [(M+2)+H]$^+$.

N-(2-(5-Chloro-2-methoxyphenylamino)-5-methyl-4,5'-bithiazol-2'-yl)pivalamide (25z)

Following the protocol outlined for 22z gave 25z. Mp decomposition at 221° C. $^1$H NMR (600 MHz, DMSO-d6): δ 11.79 (br s, 1H), 9.73 (br s, 1H), 8.57 (d, J=3 Hz, 1H), 7.67 (s, 1H), 7.01 (d, J=8.4 Hz, 1H), 6.96 (dd, J=8.4 Hz, 3 Hz, 1H), 3.86 (s, 3H), 2.43 (s, 3H), 1.26 (s, 9H). $^{13}$C NMR (150 MHz, DMSO-d6): δ 176.5, 159.6, 157.9, 146.5, 136.7, 134.0, 131.2, 126.4, 124.3, 120.6, 117.0, 116.9, 112.0, 56.1, 38.8, 26.6, 11.7. HRMS m/z (ESI) calcd. for C19H21ClN4O2S2 (M+H)$^+$ 437.0867. Found 437.0868.

2-Amino-6,7-dihydro-4H-cyclohepta[d]thiazol-8(5H)-one (26z)

Following the procedure reported by Ragan (Ragan, J. A.; Makowski, T. W.; Am Ende, D. J.; Clifford, P. J.; Young, G. R.; Conrad, A. K.; Eisenbeis, S. A. A Practical Synthesis of 1,3-cycloheptanedione. Org. Process Res. Dev. 1998, 2, 379-381) afforded cycloheptane-1,3-dione as clear and colorless oil. IR cm$^{-1}$: 2949, 2870, 1716, 1696; (Lit. 1716, 1693); b.p. 70° C. at 0.3 mmHg; $^1$H NMR matched literature data.

To a 0° C. biphasic mixture of cycloheptane-1,3-dione (5.7 g, 45.17 mmol) in CCl4/DI water (1:1; 150 mL) was added (dropwise) Br$_2$ (2.55 mL, 49.7 mmol) in CCl4 (75 mL). The mixture was stirred at 0° C. for 1 h, extracted with DCM, and the organic layer was collected. DCM was removed under reduced pressure at room temperature to afford 2bromocycloheptane-1,3-diones which was used to the next step without further purification.

To a solution of 2-bromocycloheptane-1,3-dione (45.17 mmol) in abs. EtOH (100 mL) was added thiourea (3.61 g, 47.43 mmol). The reaction mixture was stirred at room temperature overnight at which point the EtOH was removed under reduced pressure and the resulting dark orange residue was triturated with DCM. The residue was recrystallized from EtOH to afford 26z as an off white solid (6 g, 50% overall crude yield from cycloheptane-1,3-dione). $^1$H NMR (300 MHz, DMSO-d6): δ 8.87 (br s, 2H), 2.87 (t, J=6 Hz, 2H), 2.64 (t, J=6 Hz, 2H), 1.89-1.85 (m, 2H), 1.81-1.77 (m, 2H);

2-Amino-7-bromo-6,7-dihydro-4H-cyclohepta[d]thiazol-8(5H)-one (27z)

Compound 26z (1.96 g, 7.45 mmol; HBr salt form) in glacial acetic acid (70 mL) was treated dropwise with Br$_2$ (421 uL, 8.2 mmol). The reaction mixture was stirred at room temperature for 30 min. The crude product was collected by filtration, washed with cold acetone, and dried to yield 27z which was used in the next step without purification (1.98 g, 78%). $^1$H NMR (600 MHz, 2 DMSO-d6): δ 8.71 (br s, 2H), 5.11 (dd, J=6.9 Hz, 3.3 Hz, 1H), 3.08-2.90 (m, 2H), 2.473 2.39 (m, 1H), 2.28-2.20 (m, 1H), 2.14 (dd, J=10.1 Hz, 2.3 Hz, 1H), 1.98-1.90 (m, 1H). MS (ESI) m/z [M+H]$^+$ 260.92; [(M+2)+H]$^+$ 262.88. 5 6

N$^2$-(5-chloro-2-methoxyphenyl)-7,8-dihydro-6H-cyclohepta[1,2-d:3,4-d]bithiazole 2,2'-diamine (28z)

An absolute ethanol (50 mL) suspension of 27z (1.73 g, 6.64 mmol) and 4z (2.11 g, 7.3 mmol) was heated at reflux overnight. EtOH was removed under reduced pressure and the residue was recrystallized from EtOH to yield 28z (2.1 g, 84%). $^1$H NMR (400 MHz, DMSO-d6): δ 9.81 (s, 1H), 9.19 (s, 2H), 8.44 (d, J=2.4 Hz, 1H), 7.00 (d, J=8.411 Hz, 1H), 6.92 (dd, J=8.4 Hz, 2.4 Hz, 1H), 3.83 (s, 3H), 2.91-2.87 (m, 4H), 1.98 (m, 2H). $^{13}$C NMR (100 MHz, DMSO-d6): δ 167.6, 160.8, 147.0, 135.5, 131.7, 124.9, 122.0, 121.3, 13 117.2, 114.5, 112.6, 56.7, 28.9, 25.9, 21.9, 19.2. MS (ESI) m/z 378.88 [M+1]⁺.

N-(2-(5-Chloro-2-methoxyphenylamino)-7,8-dihydro-6H-cyclohepta[1,2-d:3,4-d']bithiazole-2'-yl)pivalamide (29z)

Compound 28z (1.73 g, 3.75 mmol) and dry DCM (40 mL) under $N_2$ was treated sequentially with TEA (1.32 mL, 9.38 mmol) and 2,2-dimethylpropionyl chloride (598 µL, 4.86 mmol). The suspension became light brown within 2 min and DCM was removed in vacuo at room temperature. The residue was purified by flash chromatographic column (hexane: ethyl acetate=4:1 eluent) to afford 29z (1.46 g. 84%) with 99.0% purity. Mp decomposition at 197° C.
¹H NMR (400 MHz, DMSO-d6): δ 11.60 (s, 1H), 9.65 (s, 1H), 8.58 (d, J=0.8 Hz, 1H), 6.99-6.92 (m, 2H), 3.84 (s, 3H), 3.01 (t, J=4 Hz, 2H), 1.91 (t, J=4 Hz, 2H), 1.99 (m, 2H), 1.21 (s, 9H). ¹³C NMR (100 MHz, DMSO-d6): δ 176.9, 160.1, 156.2, 146.9, 146.8, 138.1, 132.0, 125.0, 121.8, 120.9, 120.7, 117.2, 112.4, 56.7, 33.0, 27.3, 26.8, 23.0. HRMS m/z (ESI) calcd. for $C_{21}H_{23}ClN_4O_2S_2$ (M+H)⁺ 463.1024. Found 463.1019.

2-(5-Chloro-2-methoxyphenylamino)-4,5,6,7-tetrahydrocyclohepta[d]thiazol-8-one (30z)

Following the procedure described for 26z by condensing 5-chloro-2-methoxyphenylthiourea gave 30z (light brown solid; 26% for two steps). ¹H NMR (600 MHz, DMSO-d6): δ 7.81 (d, J=2.4 Hz, 1H), 7.75 (dd, J=9 Hz, 2.4 Hz, 1H), 7.42 (d, J=9 Hz, 1H), 3.83 (s, 3H), 2.84-2.75 (m, 2H), 2.58-2.52 (m, 1H), 2.33-2.28 (m, 1H), 1.90-1.74 (m, 4H). ¹³C NMR (150 MHz, DMSO-d6): δ 194.4, 169.8, 154.5, 148.9, 134.1, 130.2, 125.7, 122.6, 121.7, 116.3, 57.6, 42.9, 30.5, 24.4, 21.5.

7-Bromo-2-(5-chloro-2-methoxyphenylamino)-4,5,6,7-tetrahydrocyclohepta[d]thiazol8-one P (31z)

Followed the procedure described for 27z gave 31z (white powder; 70% yield). MS (ESI) m/z [M+H]⁺ 400.87; [(M+2)+H]⁺ 402.90.

N²-(5-Chloro-2-methoxyphenyl)-5,6-dihydro-4H-cyclohepta[1,2-d:3,4-d]'bithiazole-2,2'-diamine (32z)

Following the procedure outlined for 28z by condensing with thiourea afforded 32z as a white powder (32%). ¹H NMR (600 MHz, DMSO-d6): δ 9.48 (br s, 1H), 7.89-7.84 (m, 2H), 7.81 (d, J=2.4 Hz, 1H), 7.72 (dd, J=9 Hz, 2.4 Hz, 1H), 7.40 (d, J=9 Hz, 1H), 3.84 (s, 3H), 2.81-2.73 (m, 2H), 2.47-2.42 (m, 1H), 2.28-2.23 (m, 1H), 1.93-1.88 (m, 2H). ¹³C NMR (150 MHz, DMSO-d6): δ 166.7, 165.9, 154.0, 134.4, 134.0, 133.0, 129.6, 124.9, 121.7, 119.4, 115.4, 113.8, 56.8, 28.2, 25.3, 21.6. MS (ESI) m/z 379.01 [M+1]⁺.

N-(2-(5-Chloro-2-methoxyphenylamino)-5,6-dihydro-4H-cyclohepta[1,2-d:3,4-d']bithiazole-2'-yl)pivalamide (33z)

Following the procedure outlined for 29z gave 33z as a yellow powder (36%). ¹H NMR (600 MHz, DMSO-d6): δ 7.64 (d, J=2.4 Hz, 1H), 7.62 (dd, J=7.2 Hz, 2.4 Hz, 1H), 7.35 (d, J=7.2 Hz, 1H), 7.05 (br s, 2H), 3.82 (s, 3H), 2.87-2.85 (m, 2H), 2.68-2.64 (m, 1H), 2.48-2.44 (m, 1H), 2.02-1.96 (m, 2H), 1.02 (s, 9H). ¹³C NMR (150 MHz, DMSO-d6): δ 187.3, 167.0, 165.8, 154.3, 137.4, 133.1, 131.1, 130.3, 127.3, 124.4, 118.5, 115.4, 114.7, 57.0, 40.7, 29.0, 28.3, 26.5, 22.8. HRMS m/z (ESI) calcd. for $C_{21}H_{23}ClN_4O_2S_2$ (M+H)⁺ 463.1024. Found 463.1039.

Computational Methods

Model systems of 1z, 17z, 22z, and 29z with the t-butyl group replaced by a methyl group and the methoxy and chloro groups on the aniline replaced by hydrogens were utilized. Preliminary calculations suggested that the presence of the methoxy and chloro functional groups does not significantly affect the relative energies of the two aniline conformers. In all cases, the lowest energy aniline and amide conformers (which are also consistent with the crystal structure of 29z) were utilized.

All calculations were performed with the GAUSSIAN03 software suite. Geometries were optimized without symmetry constraints using the B3LYP/6-31+G(d,p) method. (a) Becke, A. D. Density-functional thermochemistry. III. The role of exact exchange. J. Chem. Phys. 1993, 98, 5648-5652. (b) Becke, A. D. A new mixing of Hartree-Fock and local-density-functional theories. J. Chem. Phys. 1993, 98, 1372-1377. (c) Lee, C.; Yang, W.; Parr, R. G. Development of the Colle-Salvetti correlation-energy formula into a functional of the electron density. Phys. Rev. B 1988, 37, 785-789. (d) Stephens, P. J.; Devlin, F. J.; Chabalowski, C. F.; Frisch, M. J. Ab initio calculation of vibrational absorption and circular dichroism spectra using density functional force fields. J. Phys. Chem. 1994, 98, 11623-11627) All stationary points were characterized as either minima or transition state structures via frequency calculations, and the reported energies include unscaled zero-point energy (ZPE) corrections. Single point calculations in water were completed utilizing the CPCM solvation model and UAKS radii. Structural diagrams were produced using Ball & Stick version 4.0.

That which is claimed is:
1. A composition comprising a compound of formula (III):

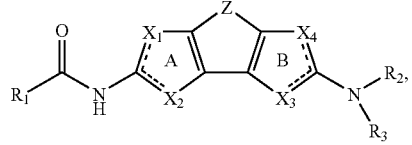

(III)

or the salts, solvates, hydrates, and prodrug forms thereof, and stereoisomers thereof,
wherein:
A and B are aromatic rings each independently selected from thiazole and oxazole, with $X_1$, $X_2$, $X_3$ and $X_4$ being heteroatoms selected from N, O and S, with each dotted line connecting $X_1$ to $X_2$ within ring A and $X_3$ to $X_4$ within ring B being a single or double bond provided that when one bond is a double bond then the other bond is a single bond;
$R_1$ is a substituted or unsubstituted group selected from aliphatic and aryl;
$R_2$ is a substituted or unsubstituted aryl;
$R_3$ is hydrogen or substituted or unsubstituted aliphatic; and
wherein Z is a bridge comprising a heteroatom or a substituted or unsubstituted lower aliphatic chain.
2. The composition of claim 1, wherein $R_1$ is an aliphatic selected from a substituted or unsubstituted alkyl and a substituted or unsubstituted alkenyl.
3. The composition of claim 1, wherein $R_2$ is an aryl consisting of a group selected from phenyl and [2,4,6]triazine.
4. The composition of claim 1, wherein said compound is conjugated to a second molecule.
5. The composition of claim 4, wherein said second molecule is a mutant-CFTR potentiator compound.

6. The composition of claim 1, wherein aromatic rings A and B comprise a bithiazole.

7. The composition of claim 1, wherein the compound is selected from the group consisting of:

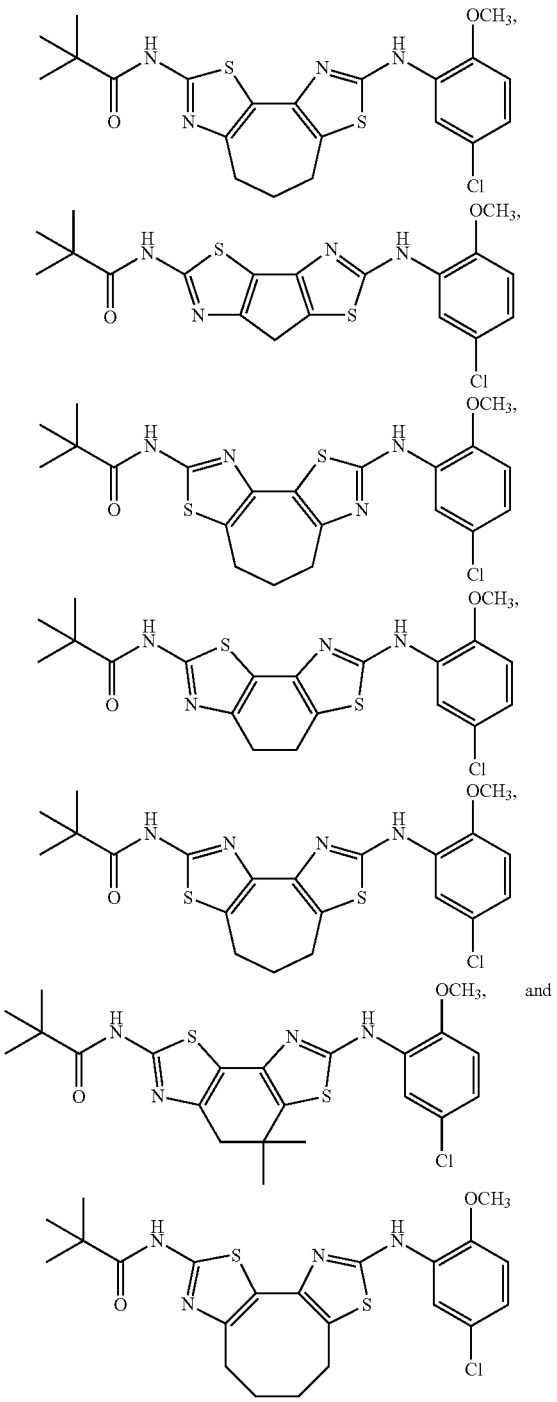

or salts, solvates, hydrates, and prodrug forms thereof, and stereoisomers thereof.

8. The composition of claim 1, wherein Z is selected from methyl, ethyl, propyl, isopropyl, butyl and isobutyl.

9. The composition of claim 1, wherein the compound is therapeutically effective increasing CFTR-mediated ion permeability of a cell producing a mutant-CFTR, and said composition is a pharmaceutical composition that comprises a therapeutically effective amount of said compound to treat cystic fibrosis.

10. A pharmaceutical composition comprising an effective amount of a mutant-CFTR corrector compound having the formula:

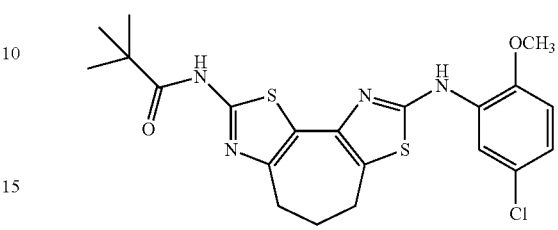

or pharmaceutically acceptable salts, solvates, hydrates, and prodrug forms thereof, and stereoisomers thereof.

11. A method of treating a subject having a condition associated with mutant-CFTR, said method comprising administering to the subject a therapeutically effective amount of a pharmaceutical composition of claim 9 wherein said condition is cystic fibrosis.

12. A method of increasing ion permeability of a cell producing a mutant-CFTR protein, said method comprising:
contacting said cell with an effective amount of a pharmaceutical composition of claim 9, said contacting being effective to increase CFTR-mediated ion permeability of said cell to treat cystic fibrosis.

13. The method of claim 12, wherein the mutant-CFTR is ΔF508-CFTR.

14. A composition comprising a compound of the formula selected from the group consisting of:

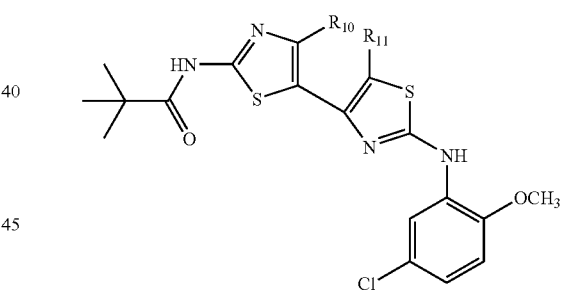

wherein $R_{10}$ and $R_{11}$ are combined to form a ring of six to eight carbons; and

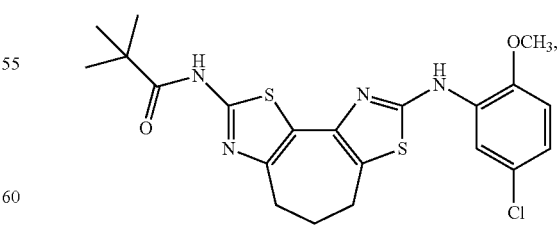

or salt, solvate, hydrate, or prodrug form thereof, or stereoisomers thereof.

* * * * *